US011739125B2

(12) United States Patent
Kramps et al.

(10) Patent No.: US 11,739,125 B2

(45) **Date of Patent: *Aug. 29, 2023**

(54) RESPIRATORY SYNCYTIAL VIRUS (RSV) VACCINE

(71) Applicant: CureVac SE, Tübingen (DE)

(72) Inventors: Thomas Kramps, Tübingen (DE); Margit Schnee, Constance (DE); Daniel Voss, Tübingen (DE); Benjamin Petsch, Tübingen (DE)

(73) Assignee: Cure Vac SE, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/316,834

(22) Filed: May 11, 2021

(65) Prior Publication Data

US 2021/0261627 A1 Aug. 26, 2021

Related U.S. Application Data

(63) Continuation of application No. 16/168,747, filed on Oct. 23, 2018, now Pat. No. 11,034,729, which is a continuation of application No. 15/488,815, filed on Apr. 17, 2017, now Pat. No. 10,150,797, which is a continuation of application No. 15/048,439, filed on Feb. 19, 2016, now Pat. No. 9,688,729, which is a continuation of application No. PCT/EP2014/002301, filed on Aug. 21, 2014.

(30) Foreign Application Priority Data

Aug. 21, 2013 (WO) ................ PCT/EP2013/002518

(51) Int. Cl.

| | |
|---|---|
| ***C07K 14/005*** | (2006.01) |
| ***A61K 39/12*** | (2006.01) |
| ***C12N 7/00*** | (2006.01) |
| ***A61K 39/155*** | (2006.01) |
| ***C07K 16/10*** | (2006.01) |
| *A61K 39/00* | (2006.01) |
| *A61K 48/00* | (2006.01) |

(52) U.S. Cl.

CPC ............ *C07K 14/005* (2013.01); *A61K 39/12* (2013.01); *A61K 39/155* (2013.01); *C07K 16/1027* (2013.01); *C12N 7/00* (2013.01); *A61K 48/00* (2013.01); *A61K 2039/505* (2013.01); *A61K 2039/53* (2013.01); *A61K 2039/6031* (2013.01); *C07K 2317/24* (2013.01); *C12N 2760/18534* (2013.01)

(58) Field of Classification Search

None

See application file for complete search history.

(56) References Cited

U.S. PATENT DOCUMENTS

| | | | |
|---|---|---|---|
| 3,906,092 | A | 9/1975 | Hilleman et al. |
| 4,373,071 | A | 2/1983 | Itakura |
| 4,401,796 | A | 8/1983 | Itakura |
| 4,415,732 | A | 11/1983 | Caruthers et al. |
| 4,578,399 | A | 3/1986 | Schorlemmer et al. |
| 5,516,652 | A | 5/1996 | Abramovitz et al. |
| 5,663,153 | A | 9/1997 | Hutcherson et al. |
| 5,663,163 | A | 9/1997 | Takaya et al. |
| 5,844,075 | A | 12/1998 | Kawakami et al. |
| 5,965,720 | A | 10/1999 | Gryaznov et al. |
| 6,096,307 | A | 8/2000 | Braswell et al. |
| 6,218,371 | B1 | 4/2001 | Krieg et al. |
| 6,239,116 | B1 | 5/2001 | Krieg et al. |
| 6,322,967 | B1 | 11/2001 | Parkin |
| 6,406,705 | B1 | 6/2002 | Davis et al. |
| 6,498,148 | B1 | 12/2002 | Raz |
| 6,514,948 | B1 | 2/2003 | Raz et al. |
| 6,552,006 | B2 | 4/2003 | Raz et al. |
| 6,589,940 | B1 | 7/2003 | Raz et al. |
| 6,610,661 | B1 | 8/2003 | Carson et al. |

(Continued)

FOREIGN PATENT DOCUMENTS

| | | |
|---|---|---|
| AU | 776268 | 12/2000 |
| DE | 102004035227 | 2/2002 |

(Continued)

OTHER PUBLICATIONS

Tarnette et al. (Journal of Virology, 2007, p. 1-10 and accession No. EF566942).*

Accession No. EF566942, 2007, p. 1-2.*

"Cell-penetrating peptide," Wikipedia, located at http://en.wikipedia.org/wiki/Cell-penetrating_peptide, downloaded Dec. 11, 2012.

"DOC/Alum Complex," Violin: Vaccine investigation and online information network, located at http://www.violinet.org/vaxjo/vaxjo_detail.php?c_vaxjo_id-49, downloaded on Aug. 28, 2012.

(Continued)

*Primary Examiner* — Agnieszka Boesen

(74) *Attorney, Agent, or Firm* — Parker Highlander PLLC

(57) ABSTRACT

The present invention relates to an mRNA sequence, comprising a coding region, encoding at least one antigenic peptide or protein of RSV infections Respiratory syncytial virus (RSV) or a fragment, variant or derivative thereof. Additionally the present invention relates to a composition comprising a plurality of mRNA sequences comprising a coding region, encoding at least one antigenic peptide or protein of RSV infections Respiratory syncytial virus (RSV) or a fragment, variant or derivative thereof. Furthermore it also discloses the use of the mRNA sequence or the composition comprising a plurality of mRNA sequences for the preparation of a pharmaceutical composition, especially a vaccine, e.g. for use in the prophylaxis or treatment of RSV infections Respiratory syncytial virus (RSV) infections. The present invention further describes a method of treatment or prophylaxis of RSV infections using the mRNA sequence.

15 Claims, 23 Drawing Sheets

Specification includes a Sequence Listing.

(56) References Cited

U.S. PATENT DOCUMENTS 6,689,757 B1 2/2004 Jacob et al.
6,716,434 B1 4/2004 Ansley et al.
7,001,890 B1 2/2006 Wagner et al.
7,208,478 B2 4/2007 Carson et al.
7,407,944 B2 8/2008 Agrawal et al.
7,470,674 B2 12/2008 Agrawal et al.
7,517,862 B2 4/2009 Agrawal et al.
7,709,007 B2 * 5/2010 Murphy .................. A61P 31/12 435/5
8,206,990 B2 6/2012 Ritt et al.
8,217,016 B2 7/2012 Hoerr et al.
8,383,340 B2 2/2013 Ketterer et al.
8,460,941 B2 6/2013 Ritt et al.
8,703,906 B2 4/2014 Baumhof et al.
8,771,728 B2 7/2014 Huang et al.
8,852,472 B2 10/2014 Keil et al.
8,968,746 B2 3/2015 Baumhof et al.
8,969,543 B2 3/2015 Jeong et al.
9,155,788 B2 10/2015 Hoerr et al.
9,226,959 B2 1/2016 Kramps et al.
9,234,013 B2 1/2016 Thess et al.
9,314,535 B2 4/2016 Baumhof et al.
9,352,028 B2 5/2016 Barner et al.
9,402,887 B2 8/2016 Probst et al.
9,421,255 B2 8/2016 Baumhof et al.
9,433,669 B2 9/2016 Hoerr et al.
9,433,670 B2 9/2016 Hoerr et al.
9,439,956 B2 9/2016 Hoerr et al.
9,447,431 B2 9/2016 Thess et al.
9,463,228 B2 10/2016 Hoerr et al.
9,572,874 B2 2/2017 Fotin-Mleczek et al.
9,616,084 B2 4/2017 Mutzke
9,623,095 B2 4/2017 Kallen et al.
9,629,812 B2 4/2017 Medarova et al.
9,655,955 B2 5/2017 Hoerr et al.
9,669,089 B2 6/2017 Thess et al.
9,683,233 B2 6/2017 Thess
9,687,262 B2 6/2017 Rousseau et al.
9,688,729 B2 * 6/2017 Kramps ............... A61K 39/155
9,737,595 B2 8/2017 Lorenz et al.
9,839,697 B2 12/2017 Thess et al.
9,890,391 B2 2/2018 Thess et al.
9,907,862 B2 3/2018 Baumhof et al.
9,974,845 B2 5/2018 Fotin-Mleczek et al.
10,010,592 B2 7/2018 Thess et al.
10,017,826 B2 7/2018 von der Mülbe et al.
10,047,375 B2 8/2018 Thess
10,080,809 B2 9/2018 Thess
10,111,967 B2 10/2018 Fotin-Mleczek et al.
10,111,968 B2 10/2018 Thess et al.
10,117,920 B2 11/2018 Fotin-Mleczek et al.
10,150,797 B2 * 12/2018 Kramps ............... A61K 39/155
10,166,283 B2 1/2019 Thess et al.
10,172,935 B2 1/2019 Kallen et al.
10,188,748 B2 1/2019 von der Mülbe et al.
10,232,024 B2 3/2019 Thess et al.
10,293,058 B2 5/2019 Fotin-Mleczek et al.
10,293,060 B2 5/2019 Baumhof
10,307,472 B2 6/2019 Fotin-Mleczek et al.
10,369,216 B2 8/2019 Fotin-Mleczek et al.
10,434,154 B2 10/2019 Probst et al.
10,434,158 B2 10/2019 Fotin-Mleczek et al.
10,441,653 B2 10/2019 Hoerr et al.
10,501,768 B2 12/2019 Eber et al.
10,517,827 B2 12/2019 Eber et al.
10,568,958 B2 2/2020 Baumhof et al.
10,568,972 B2 2/2020 von der Mülbe et al.
10,588,959 B2 3/2020 Kallen et al.
10,596,252 B2 3/2020 Kallen et al.
10,610,605 B2 4/2020 Thess et al.
10,648,017 B2 5/2020 Wochner
10,653,768 B2 5/2020 Mutzke et al.
10,653,799 B2 5/2020 Thess et al.
10,682,406 B2 6/2020 Thess et al.
10,682,426 B2 6/2020 Schnee et al.
10,711,315 B2 7/2020 von der Mülbe et al.
10,729,654 B2 8/2020 Eber et al.
10,729,761 B2 8/2020 Kallen et al.
10,738,306 B2 8/2020 Thess
10,751,424 B2 8/2020 Baumhof et al.
10,760,070 B2 9/2020 Funkner et al.
10,780,054 B2 9/2020 Ketterer et al.
10,799,577 B2 10/2020 Thess et al.
10,799,602 B2 10/2020 Baumhof
10,837,039 B2 11/2020 Wochner et al.
10,869,935 B2 12/2020 Fotin-Mleczek et al.
10,898,584 B2 1/2021 Schlake et al.
10,898,589 B2 1/2021 Thess et al.
10,912,826 B2 2/2021 Thess et al.
10,918,740 B2 2/2021 Fotin-Mleczek et al.
10,988,754 B2 4/2021 Fotin-Mleczek et al.
11,034,729 B2 * 6/2021 Kramps .................. A61P 31/14
11,078,247 B2 8/2021 Fotin-Mleczek et al.
11,110,156 B2 9/2021 Thess et al.
11,110,157 B2 9/2021 Fotin-Mleczek et al.
11,110,166 B2 9/2021 Fotin-Mleczek et al.
11,135,312 B2 10/2021 von der Mülbe et al.
11,141,474 B2 10/2021 Rauch et al.
11,141,476 B2 10/2021 Rauch
11,149,278 B2 10/2021 Thess et al.
11,179,337 B2 11/2021 Eber et al.
11,225,682 B2 1/2022 Reichert et al.
11,241,493 B2 2/2022 Rauch et al.
11,248,223 B2 2/2022 Yazdan Panah et al.
11,254,951 B2 2/2022 Thess
11,266,735 B2 3/2022 Kallen et al.
11,268,157 B2 3/2022 von der Mülbe et al.
11,274,293 B2 3/2022 Funkner et al.
2003/0133942 A1 7/2003 Segal
2003/0225016 A1 12/2003 Fearon et al.
2004/0006010 A1 1/2004 Carson et al.
2004/0006034 A1 1/2004 Raz et al.
2004/0019007 A1 1/2004 Monahan et al.
2004/0047869 A1 3/2004 Garcon et al.
2004/0052763 A1 3/2004 Mond et al.
2005/0032730 A1 2/2005 Von der Mulbe et al.
2005/0037494 A1 2/2005 Hecker et al.
2005/0059624 A1 3/2005 Hoerr et al.
2005/0130918 A1 6/2005 Agrawal et al.
2005/0215501 A1 9/2005 Lipford et al.
2005/0250723 A1 11/2005 Hoerr et al.
2006/0142227 A1 6/2006 Lamensdorf et al.
2006/0172966 A1 8/2006 Lipford et al.
2006/0188490 A1 8/2006 Hoerr et al.
2006/0188990 A1 8/2006 Kretschmer et al.
2006/0251623 A1 11/2006 Bachmann et al.
2007/0280929 A1 12/2007 Hoerr et al.
2008/0025944 A1 1/2008 Hoerr et al.
2008/0145375 A1 6/2008 Bembridge et al.
2008/0153166 A1 6/2008 Huang et al.
2008/0171711 A1 7/2008 Hoerr et al.
2008/0248067 A1 10/2008 Frazer et al.
2008/0267873 A1 10/2008 Hoerr et al.
2009/0081157 A1 3/2009 Kornbluth et al.
2009/0111765 A1 4/2009 Harmann et al.
2009/0123467 A1 5/2009 Bedi et al.
2009/0324584 A1 12/2009 Hoerr et al.
2010/0047261 A1 2/2010 Hoerr et al.
2010/0048883 A1 2/2010 Ketterer et al.
2010/0062967 A1 3/2010 Keil et al.
2010/0184953 A1 7/2010 Huang et al.
2010/0189729 A1 7/2010 Hoerr et al.
2010/0203076 A1 8/2010 Fotin-Mleczek et al.
2010/0239608 A1 9/2010 von der Mülbe et al.
2010/0291156 A1 11/2010 Barner et al.
2010/0303851 A1 12/2010 Hoerr et al.
2010/0305196 A1 12/2010 Probst et al.
2011/0053829 A1 3/2011 Baumhof et al.
2011/0077287 A1 3/2011 von der Mülbe et al.
2011/0243897 A1 10/2011 Seymour et al.
2011/0250225 A1 10/2011 Fotin-Mleczek et al.
2011/0269950 A1 11/2011 von der Mülbe et al.
2011/0311472 A1 12/2011 Hoerr et al.
2012/0009221 A1 1/2012 Hoerr et al.

(56) References Cited

U.S. PATENT DOCUMENTS

| | | | |
|---|---|---|---|
| 2012/0021043 | A1 | 1/2012 | Kramps et al. |
| 2012/0058153 | A1 | 3/2012 | Ilyinskii et al. |
| 2012/0213818 | A1 | 8/2012 | Hoerr et al. |
| 2012/0219573 | A1 | 8/2012 | Baumhof et al. |
| 2012/0258046 | A1 | 10/2012 | Mutzke |
| 2012/0258104 | A1 | 10/2012 | Echeverri et al. |
| 2013/0121998 | A1 | 5/2013 | Hoerr et al. |
| 2013/0129754 | A1 | 5/2013 | Thess et al. |
| 2013/0142818 | A1 | 6/2013 | Baumhof et al. |
| 2013/0195867 | A1 | 8/2013 | Hoerr et al. |
| 2013/0202645 | A1 | 8/2013 | Barner et al. |
| 2013/0251742 | A1 | 9/2013 | Probst et al. |
| 2013/0259879 | A1 | 10/2013 | Baumhof et al. |
| 2013/0273001 | A1 | 10/2013 | Hoerr et al. |
| 2013/0280283 | A1 | 10/2013 | Lorenz et al. |
| 2013/0281382 | A1 | 10/2013 | Huang et al. |
| 2013/0295043 | A1 | 11/2013 | Kallen et al. |
| 2013/0336998 | A1 | 12/2013 | Kallen et al. |
| 2014/0037660 | A1 | 2/2014 | Fotin-Mleczek |
| 2014/0241996 | A1 | 8/2014 | Medarova et al. |
| 2014/0294877 | A1 | 10/2014 | Baumhof |
| 2015/0037326 | A1 | 2/2015 | Butler-Ransohoff et al. |
| 2015/0050302 | A1 | 2/2015 | Thess |
| 2015/0057340 | A1 | 2/2015 | Thess et al. |
| 2015/0093413 | A1 | 4/2015 | Thess et al. |
| 2015/0118183 | A1 | 4/2015 | Baumhof |
| 2015/0118264 | A1 | 4/2015 | Baumhof et al. |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0258214 | A1 | 9/2015 | Baumhof et al. |
| 2015/0306249 | A1 | 10/2015 | Baumhof et al. |
| 2015/0320847 | A1 | 11/2015 | Thess et al. |
| 2016/0130345 | A1 | 5/2016 | Fotin-Mleczek et al. |
| 2016/0166668 | A1 | 6/2016 | Kallen et al. |
| 2016/0166678 | A1 | 6/2016 | Kallen et al. |
| 2016/0166710 | A1 | 6/2016 | Baumhof |
| 2016/0166711 | A1 | 6/2016 | Schnee et al. |
| 2016/0168207 | A1 | 6/2016 | Kramps et al. |
| 2016/0168227 | A1 | 6/2016 | Kallen et al. |
| 2016/0235864 | A1 | 8/2016 | Schlake et al. |
| 2016/0304883 | A1 | 10/2016 | Grund et al. |
| 2016/0304938 | A1 | 10/2016 | Wochner |
| 2016/0317679 | A1 | 11/2016 | Baumhof et al. |
| 2016/0326575 | A1 | 11/2016 | Von der Mulbe et al. |
| 2016/0331844 | A1 | 11/2016 | Fotin-Mleczek et al. |
| 2017/0014496 | A1 | 1/2017 | Fotin-Mleczek et al. |
| 2017/0028059 | A1 | 2/2017 | Baumhof et al. |
| 2017/0029847 | A1 | 2/2017 | Thess |
| 2017/0114378 | A1 | 4/2017 | Wochner et al. |
| 2017/0182150 | A1 | 6/2017 | Kallen et al. |
| 2017/0239372 | A1 | 8/2017 | Baumhof et al. |
| 2017/0252430 | A1 | 9/2017 | Fotin-Mleczek et al. |
| 2017/0326225 | A1 | 11/2017 | Rauch et al. |
| 2018/0044687 | A1 | 2/2018 | Thess et al. |
| 2018/0125952 | A1 | 5/2018 | Fotin-Mleczek et al. |
| 2018/0126003 | A1 | 5/2018 | Hoerr |
| 2018/0126005 | A1 | 5/2018 | Fotin-Mleczek et al. |
| 2018/0142275 | A1 | 5/2018 | Roos et al. |
| 2018/0147146 | A1 | 5/2018 | Eber et al. |
| 2018/0148727 | A1 | 5/2018 | Grund et al. |
| 2018/0201967 | A1 | 7/2018 | Eber et al. |
| 2018/0208957 | A1 | 7/2018 | Roos et al. |
| 2018/0214537 | A1 | 8/2018 | Mutzke et al. |
| 2018/0237786 | A1 | 8/2018 | Schlake et al. |
| 2018/0237817 | A1 | 8/2018 | Roos et al. |
| 2018/0243219 | A1 | 8/2018 | Ketterer et al. |
| 2018/0296663 | A1 | 10/2018 | Hipp et al. |
| 2018/0298372 | A1 | 10/2018 | Funkner et al. |
| 2018/0312545 | A1 | 11/2018 | Baumhof et al. |
| 2018/0371392 | A1 | 12/2018 | Mayer et al. |
| 2019/0010485 | A1 | 1/2019 | Yazdan Panah et al. |
| 2019/0017100 | A1 | 1/2019 | Wochner et al. |
| 2019/0024096 | A1 | 1/2019 | Schmid et al. |
| 2019/0040378 | A1 | 2/2019 | Fotin-Mleczek et al. |
| 2019/0049414 | A1 | 2/2019 | Wochner et al. |
| 2019/0083602 | A1 | 3/2019 | Roos et al. |
| 2019/0100784 | A1 | 4/2019 | Eber et al. |
| 2019/0125857 | A1 | 5/2019 | Rauch et al. |
| 2019/0133950 | A1 | 5/2019 | Eber et al. |
| 2019/0160164 | A1 | 5/2019 | Rauch et al. |
| 2019/0177714 | A1 | 6/2019 | Kunze et al. |
| 2019/0185859 | A1 | 6/2019 | Fotin-Mleczek et al. |
| 2019/0194760 | A1 | 6/2019 | Koch et al. |
| 2019/0225971 | A1 | 7/2019 | Williams |
| 2019/0241633 | A1 | 8/2019 | Fotin-Mleczek et al. |
| 2019/0249219 | A1 | 8/2019 | Reichert et al. |
| 2019/0336608 | A1 | 11/2019 | Baumhof et al. |
| 2019/0336611 | A1 | 11/2019 | Baumhof et al. |
| 2019/0343933 | A1 | 11/2019 | Horscroft et al. |
| 2019/0343942 | A1 | 11/2019 | Fotin-Mleczek et al. |
| 2019/0351044 | A1 | 11/2019 | Jasny et al. |
| 2019/0351047 | A1 | 11/2019 | Jasny et al. |
| 2019/0351048 | A1 | 11/2019 | Rauch |
| 2019/0381180 | A1 | 12/2019 | Baumhof et al. |
| 2020/0023076 | A1 | 1/2020 | Fotin-Mleczek et al. |
| 2020/0085852 | A1 | 3/2020 | Fotin-Mleczek |
| 2020/0085944 | A1 | 3/2020 | Heidenreich et al. |
| 2020/0149026 | A1 | 5/2020 | Horscroft et al. |
| 2020/0163878 | A1 | 5/2020 | Baumhof et al. |
| 2020/0179526 | A1 | 6/2020 | Baumhof et al. |
| 2020/0318097 | A1 | 10/2020 | Funkner et al. |
| 2020/0392572 | A1 | 12/2020 | Yazdan Panah et al. |
| 2021/0030864 | A1 | 2/2021 | Petsch et al. |
| 2021/0069315 | A1 | 3/2021 | Baumhof et al. |
| 2021/0162037 | A1 | 6/2021 | Jasny et al. |
| 2021/0170017 | A1 | 6/2021 | Lutz et al. |
| 2021/0180106 | A1 | 6/2021 | Wochner et al. |
| 2021/0205434 | A1 | 7/2021 | Petsch et al. |
| 2021/0260178 | A1 | 8/2021 | Jasny et al. |
| 2021/0261897 | A1 | 8/2021 | Yazdan Panah et al. |
| 2021/0361761 | A1 | 11/2021 | Lutz et al. |
| 2021/0403925 | A1 | 12/2021 | Chevessier-Tünnesen et al. |
| 2022/0040281 | A1 | 2/2022 | Schwendt et al. |
| 2022/0073962 | A1 | 3/2022 | Schwenger et al. |

FOREIGN PATENT DOCUMENTS

| | | |
|---|---|---|
| DE | 10148886 | 4/2003 |
| DE | 69819150 | 7/2004 |
| DE | 102006007433 | 8/2007 |
| EP | 0347501 | 12/1989 |
| EP | 0772619 | 5/1997 |
| EP | 0839912 | 5/1998 |
| EP | 1063232 | 3/2001 |
| EP | 1083232 | 3/2001 |
| EP | 1167379 | 1/2002 |
| EP | 1374894 | 1/2004 |
| EP | 1393745 | 3/2004 |
| EP | 1564291 | 8/2005 |
| EP | 1905844 | 2/2008 |
| JP | 2005-521749 | 7/2005 |
| JP | 2008-507271 | 3/2008 |
| JP | 2008-542500 | 11/2008 |
| KR | 10-1003622 | 9/2003 |
| KR | 10-1051785 | 1/2005 |
| KR | 10-1032853 | 4/2005 |
| RU | 2407749 C2 | 12/2007 |
| RU | 2010135630 A1 | 3/2012 |
| WO | WO 1991/005560 | 5/1991 |
| WO | WO 1994/017093 | 8/1994 |
| WO | WO 1994/017792 | 8/1994 |
| WO | WO 1998/019710 | 5/1998 |
| WO | WO 1998/047913 | 10/1998 |
| WO | WO 1999/053961 | 10/1999 |
| WO | WO 2000/075304 | 12/2000 |
| WO | WO 2001/004135 | 1/2001 |
| WO | WO 2001/054720 | 8/2001 |
| WO | WO 2001/075164 | 10/2001 |
| WO | WO 2001/093902 | 12/2001 |
| WO | WO 2001/097843 | 12/2001 |
| WO | WO 2002/000594 | 1/2002 |
| WO | WO 2002/000694 | 1/2002 |
| WO | WO 2002/078614 | 10/2002 |

(56) References Cited

FOREIGN PATENT DOCUMENTS

WO WO 2002/085434 10/2002
WO WO 2002/098443 12/2002
WO WO 2003/000227 1/2003
WO WO 2003/028656 4/2003
WO WO 2003/057822 7/2003
WO WO 2003/059381 7/2003
WO WO 2003/066649 8/2003
WO WO 2003/068942 8/2003
WO WO 2003/086280 10/2003
WO WO 2004/004743 1/2004
WO WO 2004/058159 7/2004
WO WO 2004/064782 8/2004
WO WO 2004/092329 10/2004
WO WO 2005/001022 1/2005
WO WO 2005/030259 4/2005
WO WO 2005/035549 4/2005
WO WO 2005/039501 5/2005
WO WO 2005/062947 7/2005
WO WO 2005/097993 10/2005
WO WO 2006/015789 2/2006
WO WO 2006/022712 3/2006
WO WO 2006/029223 3/2006
WO WO 2006/046978 5/2006
WO WO 2006/050280 5/2006
WO WO 2006/069782 7/2006
WO WO 2006/080946 8/2006
WO WO 2006/116458 11/2006
WO WO 2007/008300 1/2007
WO WO 2007/031319 3/2007
WO WO 2007/031322 3/2007
WO WO 2007/042554 4/2007
WO WO 2007/051303 5/2007
WO WO 2007/062107 5/2007
WO WO 2007/069068 6/2007
WO WO 2007/124755 11/2007
WO WO 2008/014979 2/2008
WO WO 2008/022046 2/2008
WO WO 2009/030254 3/2009
WO WO 2009/030481 3/2009
WO WO 2009/046739 4/2009
WO WO 2009/053700 4/2009
WO WO 2009/086640 7/2009
WO WO 2009/095226 8/2009
WO WO 2009/127230 10/2009
WO WO 2009/144230 12/2009
WO WO 2010/027827 3/2010
WO WO 2010/037408 4/2010
WO WO 2010/037539 4/2010
WO WO 2010/088927 8/2010
WO WO 2011/011631 1/2011
WO WO 2011/026641 3/2011
WO WO 2011/069528 6/2011
WO WO 2011/069587 6/2011
WO WO 2011/144358 11/2011
WO WO 2012/013326 2/2012
WO WO 2012/019630 2/2012
WO WO 2012/019780 2/2012
WO WO 2012/037078 3/2012
WO WO 2012/089338 7/2012
WO WO 2012/113413 8/2012
WO WO 2012/113513 8/2012
WO WO 2012/116714 9/2012
WO WO 2012/116715 9/2012
WO WO 2012/116810 9/2012
WO WO 2012/116811 9/2012
WO WO 2013/113325 8/2013
WO WO 2013/113326 8/2013
WO WO 2013/113501 8/2013
WO WO 2013/113502 8/2013
WO WO 2013/113736 8/2013
WO WO 2013/120626 8/2013
WO WO 2013/120627 8/2013
WO WO 2013/120628 8/2013
WO WO 2013/120629 8/2013
WO WO 2013/143698 10/2013
WO WO 2013/143699 10/2013
WO WO 2013/143700 10/2013
WO WO 2013/174409 11/2013
WO WO 2014/127917 8/2014
WO WO 2015/024664 2/2015
WO WO 2015/024665 2/2015
WO WO 2015/024666 2/2015
WO WO 2015/024667 2/2015
WO WO 2015/024668 2/2015
WO WO 2015/024669 2/2015
WO WO 2015/101414 7/2015
WO WO 2015/149944 10/2015
WO WO 2016/091391 6/2016
WO WO 2016/097065 6/2016
WO WO 2016/107877 7/2016
WO WO 2016/170176 10/2016

OTHER PUBLICATIONS

"QS21," Wikipedia, located at http://en.wikipedia.org/wiki/QS21, downloaded on Dec. 11, 2012.

"Ribi vaccine adjuvant," Violin: Vaccine investigation and online information network, located at http://www.violinet.org/vaxjo/vaxjo_detail.php?c_vaxjo_id=21, downloaded on Dec. 17, 2012.

"SPT (Antigen Formulation)," Violin: Vaccine investigation and online information network, located at http://www.violinet.org/vaxjo/vaxjo_detail.php?c_vaxjo_id=72, downloaded on Aug. 21, 2012.

"Virus-like particle," Wikipedia, located at http://en.wikipedia.org/wiki/virus-like_particle, downloaded on Sep. 3, 2012.

Adams et al., "Preparation and hybridization properties of oligonucleotides containing 1-alpha-D-arabinofuranosylthymine", *Nucleic Acids Res*., 19(13):3647-51, 1991.

Agrawal, "Antisense oligonucleotides: towards clinical trials", *Trends Biotechnol*., 14(10):376-387, 1996.

Anderson et al., "Strategic priorities for respiratory syncytial virus (RSV) vaccine development," *Vaccine*, 31S:B209-B215, 2013.

Andreu et al., "Formation of disulfide bonds in synethetic peptides and proteins," Chapter 7, *Methods in Molecular Biology*, vol. 35, Peptide Synthesis Protocols, Pennington and Dunn, 1994.

Ara et al., "Zymosan enhances the immune response to DNA vaccine for human immunodeficiency virus type-1 through the activation of complement system", *Immunology*, 103(1):98-105, 2001.

Bauer et al., "The impact of intragenic CpG content on gene expression," *Nucleic Acids Research*, 38(12):3891-3908, 2010.

Bayard et al., "Antiviral activity in L1210 cells of liposome-encapsulated (2'-5')oligo(adenylate)analogues", *Eur J Biochem*., 151(2):319-326, 1985.

Berzofsky et al., "Progress on new vaccine strategies against chronic viral infections", *J Clin Invest*., 114(4):450-62, 2004.

Bettinger T. et al., "Peptide-mediated RNA delivery: a novel approach for enhanced transfection of primary and Post-mitotic cells," *Nucleic Acids Research*, vol. 29, No. 18, pp. 3882-3891, 2001.

Blaxter et al., "The *Brugia malayi* genome project: expressed sequence tags and gene discovery", *Transactions of the Royal Society of Tropical Medicine and Hygiene*, 96(1):1-17, 2002.

Bocchia et al., "Antitumor vaccination: where we stand", *Heamatologica*, 85(11):1172-1206, 2000.

Bolhassani A. et al., "Improvement of different vaccine delivery systems for cancer therapy," *Molecular Cancer*, vol. 10, No. 1, p. 3, Jan. 7, 2011.

Bot A. et al., "Enhanced protection against influenza virus of mice immunized as newborns with a mixture of plasmids expressing hemagglutinin and nucleoprotein," *Vaccine*, 16, No. 17, pp. 1675-1682, Oct. 1, 1998.

Bot A. et al., "Genetic immunization of neonates, Microbes and Infection, Institut Pasteur," vol. 4, No. 4, pp. 511-520, Apr. 2002.

Bot A. et al., "Induction of humoral and cellular immunity against influenza virus by immunization of newborn mice with a plasmid bearing a hemagglutinin gene," *International Immunology*,vol. 9, No. 11, pp. 1641-1650, Dec. 31, 1997.

Brito et al., "Non-viral eNOS gene delivery and transfection with stents for the treatment of restenosis," *BioMedical Engineering OnLine*, 9:56, 2010.

(56) References Cited

OTHER PUBLICATIONS

Burke R.S. et al., "Extracellular barriers to in Vivo PEI and PEGylated PEI polyplex-mediated gene delivery to the liver," *Bioconjug Chem*. Mar. 2008;19(3):693-704. Epub Feb. 23, 2008.
Buteau et al., "Challenges in the development of effective peptide vaccines for cancer", *Mayo Clin Proc*., 77:339-349, 2002.
Cancer.net, "What are Cancer Vaccines?" Jun. 2018, 4 pages (Year: 2018).
CAPLUS accession No. 190686-49-8; *Brugia malayi* strain TRS Labs conie RRAMCA1537 EST; *Chemical Abstracts Services*; Database CAPLUS; Jun. 2009.
Carralot J-P. et al., "Polarization of immunity induced by direct injection of naked sequence-stabilized mRNA vaccines," *CMLS Cellular and Molecular Life Sciences*, vo. 61, No. 18, pp. 2418-2424, Sep. 1, 2004.
Casciato et al., Manual of Clinical Oncology, 6th Edition, Lippincott Williams & Wilkins, 2009.
Cooper et al., "CPG 7909 adjuvant improves hepatitis B virus vaccine seroprotection in antiretroviral-treated HIV-infected adults," *AIDS*, 19:1473-1479, 2005.
Danhier et al., "PLGA-based nanoparticles: An overview of biomedical applications," *Journal of Controlled Release*, 161:505-522, 2012.
Declaration of Regina Heidenreich Under 37 C.F.R. §1.132, regarding Lipford et al., submitted in U.S. Appl. No. 14/375,215, executed Jun. 1, 2018.
Declaration of Regina Heidenreich Under 37 C.F.R. §1.132, regarding Heidenreich et al., submitted in U.S. Appl. No. 14/375,215, executed Jun. 1, 2018.
Deshayes S. et al., "Cell-penetrating peptides: tools for intracellular delivery of therapeutics," *Cell Mol Life Sci*., 62(16):1839-49. Review. 2005.
Diebold et al., "Innate antiviral responses by means of TLR7-mediated recognition of single-stranded RNA", *Science*, 1529-1531, 2004.
Dmitriev, "Bactenecin 7 peptide fragment as a tool for intracellular delivery of a phosphorescent oxygen sensor," *FEBS Journal*, 277:4651-4661, 2010.
Dohmen et al., "Nanoparticle-based programmed drug and nucleic acid delivery—an option for nanomedicine," J. Vascular Res., 48/s1:67, Abstract IS45, 2011.
EBI Database accession No. BP836659; *Arabidopsis thaliana* clone RAFL22-17-C17 EST; Database EMBL; Jan. 2005.
EBI Database accession No. CZ193289; PST12107-MICB1 *Mus musculus* genomic clone PST12107-NR; Database EMBL; Feb. 2005.
EBI Database accession No. DN868844; NEIBank analysis of Dog lens; Wistow, G., Database EMBL; Apr. 2005.
Eliyahu et al., "Polymers for DNA delivery," *Molecules*, 10:34-64, 2005.
EMBL accession No. AA430815; Brugia malayi strain TRS Labs clone RRAMCA1537 EST; Database EMBL; May 1997.
Fajac I. et al., "Histidylated polylysine as a synthetic vector for gene transfer into immortalized cystic fibrosis airway surface and airway gland serous cells," *J Gene Med*. 2(5):368-78. Sep.-Oct., 2000.
Feroze-Merzoug et al., "Molecular profiling in prostate cancer", *Cancer and Metastasis Reviews*, 20:165-171, 2001.
Fire et al., "Potent and specific genetic interferences by double-stranded RNA in *Caenorhabditis elegans*", 391:806-811, 1998.
Foerg C. et al., "On the biomedical promise of cell penetrating peptides: limits versus prospects," *J Pharm Sci*., 97(1):144-62, 2008.
Fotin-Mleczek et al., "Highly potent mRNA based cancer vaccines represent an attractive platform for combination therapies supporting an improved therapeutic effect," *The Journal of Gene Medicine*, 14(6):428-439, 2012.
Fotin-Mleczek et al., "Messenger RNA-based vaccines with dual activity induce balanced TLR-7 dependent adaptive immune responses and provide antitumor activity", *Journal of Immunotheraphy*, 34(1):1-15, 2011.
Fox, "Squalene emulsions for parenteral vaccine and drug delivery," *Molecules*, 14:3286-3312, 2009.
Fujita T et al., "Calcium enhanced delivery of tetraarginine-PEG-lipid-coated DNA/protamine complexes," *International Journal of Pharmaceutics*, vol. 368, No. 1-2, pp. 186-192, Feb. 23, 2009.
Galbraith et al., "Complement activation and hemodynamic changes following intravenous administration of phosphorothioate oligonucleotides in the monkey", *Antisense Research and Development*, 4:201-206, 1994.
Gao X et al., Nonviral gene delivery: what we know and what is next, *AAPS J*. 23;9(1):E92-104. Review. Mar. 2007.
Garinot et al., "PEGylated PLGA-based nanoparticles targeting M cells for oral vaccination," *Journal of controlled release*, vol. 120, No. 3, pp. 195-204, Jul. 17, 2007.
GenBank Accession No. JK489756.1, GI; 346421249, publicly available Sep. 2011.
Gerogieva et al., "Comparative study on the changes in photosynthetic activity of the homoiochlorophyllous desiccation-tolerant *Haberlea rhodopensis* and desiccation-sensitive spinach leaves during desiccation and rehydration", *Photosynthesis Research*, 65:191-203, 2005.
Giel-Peitraszuk M. et al., "Database Biosis," DB Acc. No. Prev199800116011, 1997.
Gravekamp et al., "Cancer vaccines in old age," *Experimental Gerontology*, vol. 42, No. 5, pp. 441-450, Apr. 14, 2007.
Gryaznov, "Oligonucleotide N3'-P5' phosphoramidates as potential therapeutic agents", *Biochimica et Biophysica Acta*, 1489:131-140, 1999.
Hamidi M. et al., "Pharmacokinetic consequences of pegylation," *Drug Deliv*.; 13(6) pp. 399-409, 2006.
Hamm et al., "Immunostimulatory RNA is a potent inducer of antigen-specific cytotoxic and humoral immune response in vivo," *International Immunology*, 19(3):297-304, 2007.
Hardy et al., "Synergistic effects of gene delivery—co-formulation of small disulfide-linked dendritic polycations with Lipofectamine 2000", *Organic and Biomolecular Chemistry*, 7(4):789-793, 2009.
Hashimoto et al., "Neutralizing epitopes of RSV and palivizumab resistance in Japan", *Fukushima J. Med. Sci*., 63(3):127-134, 2017.
Hausch et al., "A novel carboxy-functionalized photocleavable dinucleotide analog for the selection to RNA catalysts", *Tetrahedron Letters*, 39(34):6157-6158, 1998.
Hause et al., "Sequence variability of the respiratory syncytial virus (RSV) fusion gene among contemporary and historical genotypes of RSV/A and RSV/B", *PLoS One*, 12(4):e0175792, 2017.
Heffernan et al., "Disulfide-crosslinke plyion micelles for delivery of protein therapeutics", *Annals of Biomedical Engineering*, 37(10):1993-2002, 2009.
Heidenreich et al., "A novel RNA-based adjuvant combines strong immunostimulatory capacities with a favorable safety profile," *Int. J. Cancer*, 137(2):372-384, 2015.
Heidenreich et al., "Chemically modified RNA: approaches and applications", *The FASEB Journal*, 7(1):90-6, 1993.
Heidenreich et al., "RNAdjuvant, a novel highly potent RNA-based adjuvant supports induction of balanced immune response (TH1 and TH2) and anti-tumor activity," *J. lmmunotherapy*, Meeting Info: 26th Annual Scientific Meeting of Society of lmmunotherapy of Cancer, Abstract only, 34(9):663-664, 2011.
Heil et al., "Species-specific recognition of single-stranded RNA via Toll-like receptor 7 and 8", *Science*, vol. 303, pp. 1526-1529, 2004.
Herbert et al., "Lipid modification of GRN163, an N3'-P5' thiophosphoramidate oligonucleotide enhances the potency telomerase inhibition", *Oncogene*, 24:5262-5268, 2005.
Herbert et al., *The Dictionary of Immunology*, Academic Press: San Diego, 4th ed. 1995. Print.
Heyman, "The immune complex: possible ways of regulating the antibody response", *Immunology Today*, 11(9):310-313, 1990.
Higgins et al., "Advances in RSV vaccine research and development—A global agenda," *Vaccine*, 34(26):2870-2875, 2016.
Hoerr et al., "In vivo application of RNA leads to induction of specific cytotoxic T lymphocytes and antibodies", *Eur J Immunol*., 30(1):1-7, 2000.
Huang et al., "Recent development of therapeutics for chronic HCV infection", *Antiviral Res*., 71:351-362, 2006.

(56) References Cited

OTHER PUBLICATIONS

Huget et al., "Adjuvant and suppressor activity of the polycation protamine hydrochloride in the primary immune response of mice", *Z Immunitatsforsch Immunobiol.*, 152(3):190-9, 1976. (English Abstract).

Hwang et al., "A brain-targeted rabies virus glycoprotein-disulfide linked PEI nanocarrier for delivery of neurogenic microRNA," *Biomaterials*, 32:4968-4975, 2011.

Janssens et al., "Role of toll-like receptors in pathogen recognition", *Clinical Microbiology Reviews*, 16(4):637-646, 2003.

Jones et al, "Sendai virus-based RSV vaccine protects African green monkeys from RSV infection," *Vaccine*, 30(5):959-968, 2012.

Kallen et al., "A novel, disruptive vaccination technology," *Human Vaccines & Immunotherapeutics*, 9(10):2263-2276, 2013.

Kilk, "Cell-penetrating peptides and bioactive cargoes. Strategies and mechanisms," *Department of Neurochemistry and Neurotoxicology, Stockholm University*, Doctoral dissertation, 2004.

Kim et al., "Bioreducible polymers for gene delivery," *React Funct Polym*, 71(3):344-349, 2011.

Kim et al., "VeGF siRNA delivery system using arginine-grafted bioreducible poly(disulfide amine)", *Molecular Pharmaceutics*, 6(3):718-726, 2009.

Knop et al., "Poly(ethylene glycol) in drug delivery: pros and cons as well as potential alternatives," *Angew. Chem. Int. Ed.*, 49:6288-6308, 2010.

Kovarik J. et al., "Optimization of vaccine responses in early life: the role of delivery systems and immunomodulators," *Immunology and Cell Biology*, vol. 76, No. 3, pp. 222-236, Jun. 1998.

Koziel et al., "Hepatitis C virus (HCV)-specific cytotoxic T lymphocytes recognize epitopes in the core and envelope proteins of HCV", *J Virol.*, 67(12):7522-32, 1993.

Kwiatkowski et al., "The 9-(4-Octadecyloxyphenylxanthen)-9-yl-Group. A new Acid-labile Hydroxyl Protective Group and Its Application in the Preparative Reverse-phase Chromatographic Separation of Oligoribonucleotides", *Acta Chemica Scandinavica*, 38b:657-671, 1984.

Kwok KY et al., "Formulation of highly soluble poly(ethylene glycol)-peptide DNA condensates," *J Pharm Sci.*;88(10):996-1003, Oct. 1999.

Lo et al., "An endosomolytic Tat peptide produced by incorporation of histidine and cysteine residues as a nonviral vector for DNA transfection", *Biomaterials*, 29(15):2408-2414, 2008.

Lochmann et al., "Drug delivery of oligonucleotides by peptides," *European Journal of Pharmaceutics and Biopharmaceutics*; vol. 58, No. 2, pp. 237-251, 2004.

Martin M.E. et al., "Peptide-guided gene delivery," *AAPS J.* 9;9(1):E18-29. Review. Feb. 2007.

Mateo et al., "An HLA-A2 poly epitope vaccine for melanoma immunotheraphy", *J Immunol.*, 163:4058-4063, 1999.

Matray and Gryaznov., "Synthesis and properties of RNA analogs-oligoribonucleotide N3'-P5' phosphoramidates", *Nucleic Acids Research*, 27(20):3976-85, 1999.

Mattner et al., "Vaccination with poly-L-arginine as immunostimulant for peptide vaccines: induction of potent and long-lasting T-cell responses against cancer antigens," *Cancer Research*, 62(5):1477-1480, 2002.

McKenzie et al., "A potent new class of reductively activated peptide gene delivery agents", *Journal of Biological Chemistry*, 275(14):9970-9977, 2000.

McKenzie et al., "Low molecular weight disulfide cross-linking peptides as nonviral gene discovery carriers", *Bioconjugate Chemistry*, 11(6):901-909, 2000.

McLellan et al., "Structure and Function of Respiratory Syncytial Virus Surface Glycoproteins", *Curr. Top. Microbiol. Immunol.*, 372:83-104, 2014.

Melief et al., "Immunotherapy of established (pre)malignant disease by synthetic long peptide vaccines," Nature Reviews Cancer, 8:351-360, 2008.

Milich et al., "The hepatitis B virus core and e antigens elicit different Th cell subsets: antigen structure can affect Th cell phenotype", *J Virol.*, 71(3):2192-201, 1997.

Minks et al., "Structural requirements of double-stranded RNA for the activation of 2',5'-oligo(A)polymerase and protein kinase of interferon-treated HeLa cells", *The Journal of Biological Chemistry*, 254(20):10180-10183, 1979.

Miyata et al., "Block catiomer polyplexes with regulated densities of charge and disulfide cross-linking directed to enhance gene expression", *Journal of the American Chemical Society*, 126(8):2355-2361, 2004.

Mocellin et al., "Part I: Vaccines for solid tumours," The Lancet/ Oncology, 5:681-689, 2004.

Nakamura Y et al., "Octaarginine-modified multifunctional envelope-type nano device for siRNA," *J Control Release*. Jun. 22, 2007, 119(3):360-7. Epub Mar. 23, 2007.

National Cancer Institute, Fact Sheet, Cancer Vaccines, Jun. 21, 2011, 9 pages (Year: 2011).

Neu Met al., "Recent advances in rational gene transfer vector design based on poly( ethylene imine) and its derivatives," *J Gene Med.*, 7(8):992-1009, Aug. 2005.

Nicholson et al., "Accurate in vitro cleavage by RNase III of phosphorothioate-substituted RNA processing signals in bacteriophage T7 early mRNA", *Nucleic Acids Res.*, 16(4):1577-91, 1988.

Office Communication issued in corresponding Japanese Application No. 2019-180689, dated Oct. 6, 2020. English translation appended.

Office Communication issued in U.S. Appl. No. 13/824,449, dated Jan. 29, 2016.

Office Communication issued in U.S. Appl. No. 13/824,449, dated May 8, 2015.

Office Communication issued in U.S. Appl. No. 13/824,449, dated Sep. 17, 2014.

Office Communication issued in U.S. Appl. No. 14/375,215, dated Feb. 4, 2016.

Office Communication issued in U.S. Appl. No. 14/375,215, dated Jan. 16, 2018.

Office Communication issued in U.S. Appl. No. 14/375,215, dated Jul. 9, 2015.

Office Communication issued in U.S. Appl. No. 14/375,215, dated May 30, 2019.

Office Communication issued in U.S. Appl. No. 14/375,215, dated Nov. 17, 2016.

Office Communication issued in U.S. Appl. No. 14/375,215, dated Oct. 5, 2018.

Office Communication issued in U.S. Appl. No. 15/048,439, dated Feb. 22, 2017.

Office Communication issued in U.S. Appl. No. 15/206,036, dated Mar. 23, 2017.

Office Communication issued in U.S. Appl. No. 15/206,036, dated Nov. 22, 2017.

Office Communication issued in U.S. Appl. No. 15/206,036, dated Sep. 11, 2018.

Office Communication issued in U.S. Appl. No. 15/206,036, dated Jun. 25, 2019.

Office Communication issued in U.S. Appl. No. 15/300,682, dated Jan. 29, 2018.

Office Communication issued in U.S. Appl. No. 15/300,682, dated May 25, 2018.

Office Communication issued in U.S. Appl. No. 15/300,682, dated Jan. 7, 2019.

Office Communication issued in U.S. Appl. No. 15/300,682, dated Mar. 20, 2019.

Office Communication issued in U.S. Appl. No. 15/488,815, dated Jan. 9, 2018.

Office Communication issued in U.S. Appl. No. 15/488,815, dated Jul. 25, 2018.

Office Communication issued in U.S. Appl. No. 16/168,747, dated Apr. 30, 2020.

Office Communication issued in U.S. Appl. No. 16/168,747, dated Feb. 11, 2021.

Office Communication issued in U.S. Appl. No. 16/445,134, dated Oct. 1, 2020.

(56) References Cited

OTHER PUBLICATIONS

Office Communication issued in U.S. Appl. No. 16/445,134, dated May 13, 2021.
Office Communication issued in U.S. Appl. No. 16/555,881, dated Mar. 5, 2020.
Office Communication issued in U.S. Appl. No. 16/555,881, dated Aug. 6, 2020.
Office Communication issued in U.S. Appl. No. 16/555,881, dated Jun. 24, 2021.
Oomens et al., "The cytoplasmic tail of the human respiratory syncytial virus F protein plays critical roles in cellular localization of the F protein and infectious progeny production," *Journal of Virology*, 80(21):10465-10477, 2006.
Oupicky D. et al., "Importance of lateral and steric stabilization of polyelectrolyte gene delivery vectors for extended systemic circulation," *Mol Ther.*, 5(4):463-72, Apr. 2002.
Oupicky D. et al., "Laterally stabilized complexes of DNA with linear reducible polycations: strategy for triggered intracellular activation of DNA delivery vectors," *J Am Chem. Soc.*, 124(1):8-9, Soc., Jan. 9, 2002.
Parker A.L. et al., "Enhanced gene transfer activity of peptide-targeted gene-delivery vectors," *J Drug Target.*, 13(1):39-51, Jan. 2005.
Parkinson et al., "A transcriptomic analysis of the phylum Nematoda", *Nature Genetics*, 36(12):1259-1267, 2004.
PCT International Search Report and Written Opinion issued in International Application No. PCT/EP2015/000706, dated Oct. 13, 2015.
PCT International Search Report and Written Opinion issued in International Application No. PCT/EP2014/002301, dated Mar. 6, 2015.
Petsch et al., "Protective efficacy of in vitro synthesized, specific mRNA vaccines against influenza A virus infection," *Nature Biotechnology*, 30(12):1210-1216, 2012.
Pichon C. et al., "Poly[Lys-(AEDTP)]: a cationic polymer that allows dissociation of pDNA/cationic polymer complexes in a reductive medium and enhances polyfection," *Bioconjug Chem.*, 13(1):76-82, Jan.-Feb. 2002.
Pomroy N.C. et al., "Solubilization of hydrophobic peptides by reversible cysteine PEGylation," Biochem Biophys Res Commun., 245(2):618-21, Apr. 17, 1998.
Racanelli et al., "Presentation of HCV antigens to naive CD8+T cells: why the where, when, what and how are important for virus control and infection outcome", *Clin Immunol.*, 124(1):5-12, 2007.
Radu D.L. et al., "Plasmid expressing the influenza HA gene protects old mice from lethal challenge with influenza viraus," *Viral Immunology*, vol. 12, No. 3, pp. 217-226, 1999.
Ramazeilles et al., "Antisense phosphorothioate oligonucleotides: selective killing of the intracellular parasite *Leishmania amazonensis", Proc Natl Acad Sci USA*, 91(17):7859-63, 1994.
Read et al., "Vectors based on reducible polycations facilitate intracellular release of nucleic acids", *The Journal of Gene Medicine*, 5(3):232-245, 2003.
Read M.L. et al., "A versatile reducible polycation-based system for efficient delivery of a broad range of nucleic acids," *Nucleic Acids Res.*, 33(9):e86, May 24, 2005.
Read M.L. et al., "RNA-based therapeutic strategies for cancer," *Expert Opinion on Therapeutic Patents*, vol. 13, No. 5, pp. 627-638, 2003.
Riedl et al., "Priming Th1 immunity to viral core particles is facilitated by trace amounts of RNA bound to its arginine-rich domain", *J Immunol.*, 168(10):495 1-9, 2002.
Rittner et al., "New basic membrane-destabilizing peptides for plasmid-based gene delivery in Vitro and in Vivo," *Molecular Therapy*, 5(2)104-114, 2002.
Rollier et al., "Control of heterologous hepatitis C virus infection in chimpanzees is associated with the quality of vaccine-induced peripheral t-helper immune response", *J Virol.*, 78(1):187-196, 2004.
Romagne et al., "Current and future drugs targeting one class of innate immunity receptors: the toll-like receptors", *Drug Discov Today*, 12(1-2):80-7, 2007.
Rozenfeld et al., "Stable assemblies of cationic bilayer fragments and CpG oligonucleotide with enhanced immunoadjuvant activity in vivo", *Journal of Controlled Release*, 160(2):367-373, 2011.
Saenz-Badillos et al., "RNA as a tumor vaccine: a review of the literature", *Exp Dermatol.*, 10(3):143-154, 2001.
Sakae M. et al., "Highly efficient in vivo gene transfection by plasmid/PEI complexes coated by anionic PEG derivatives bearing carboxyl groups and RGD peptide," *Biomedicine and Pharmacotherapy*, vol. 62, No. 7, pp. 448-453, Sep. 1, 2008.
Scheel et al., "Therapeutic anti-tumor immunity triggered by injections of immunostimulating single-stranded RNA," *Eur J lmmunol*, vol. 36, No. 10, pp. 2807-2816, 2006.
Scheel et al., "Toll-like receptor-dependent activation of several human blood cell types by protamine-condensed mRNA," *Eur J lmmunol*, vol. 35, No. 5, pp. 1557-1566, 2005.
Scheel et al., "Immunostimulating capacities of stabilized RNA molecules", *Eur J Immunol.*, 24:537-547, 2004.
Scheel et al., "mRNA as immunostimulatory molecule", Krebsimmuntherapie Annual Meeting, Oral Presentation May 9, 2003. (Abstract).
Schirrmacher et al., "Intra-pinna anti-tumor vaccinaton with self-replicating infectious RNA or with DNA encoding a model tumor antigen and a cytokine", *Gene Therapy*, 7(13):1137-1147, 2000.
Schlake et al., "Developing mRNA-vaccine technologies," *RNA Biology*, 9(11):1319-1330, 2012.
Shea et al., "Synthesis, hybridization properties and antiviral activity of lipid-oligodeoxynucleotide conjugates", *Nucleic Acids Research*, 18(13):3777-3783, 1990.
Shiffman et al., "Protein dissociation from DNA in model systems and chromatin," *Nucleic Acids Res.*, 5(9):3409-3426, 1978.
Shirai et al., "An epitope in hepatitis C virus core region recognized by cytotoxic T cells in mice and humans", *J Virol.*, 68(5):3334-3342, 1994.
Stephens et al., "Sequence analysis of the major outer membrane protein gene from *Chlamydia trachomatis* serovar L2", *Journal of Bacteriology*, 168(3):1277-1282, 1986.
Sun et al., "Advances in saponin-based adjuvants," *Vaccine*, 27:1787-1796, 2009.
Takae S. et al., "PEG-detachable polyplex micelles based on disulfide-linked block catiomers as bioresponsive nonviral gene vectors," *J Am Chem Soc.*, 130(18):6001-9, May 7, 2008. Epub Apr. 9, 2008.
Tan et al., "Strategies for hepatitis C therapeutic intervention: now and next", *Curr Opin in Pharmacology*, 4:465-470, 2004.
Tanaka et al., "Disulfide crosslinked stearoyl carrier peptides containing arginine and histidine enhance siRNA uptake and gene silencing," *International Journal of Pharmaceutics*, 398:219-224, 2010.
Teplova et al., "Crystal structure and improved antisense properties of 2'-O-(2-methoxyethyl)-RNA", *Nature Structural Biology*, 6(6):535-539, 1999.
Tokunaga et al., "Effect of oligopeptides on gene expression: comparison of DNA/peptide and DNA/peptide/liposome complexes", *International Journal of Pharmaceutic*, 269(1):71-80, 2004.
Tönges L. et al., "Stearylated octaarginine and artificial virus-like particles for transfection of siRNA into primary rat neurons," *RNA*, 12(7):1431-8. Epub May 12, 2006.
Trinchieri et al., "Cooperation of toll-like receptor signals in innate immune defence", *Nature Reviews Immunology*, 7:179-190, 2007.
Tse et al., "Update on toll-like receptor-directed therapies for human disease", *Ann Rheum Dis.*, 66 Suppl 3:iii77-80, 2007.
Unnamalai N. et al., "Cationic oligopeptide-mediated delivery of dsRNA for posttranscriptional gene silencing in plant cells," *FEBS Lett.*, 566(1-3):307-10, May 21, 2004.
Vivès E. et al., "A truncated HIV-1 Tat protein basic domain rapidly translocates through the plasma membrane and accumulates in the cell nucleus," *J Biol Chem.*, 272(25):16010-7, Jun. 20, 1997.
Wang Y.H. et al., "An intracellular delivery method for siRNA by an arginine-rich peptide," *J Biochem Biophys Methods*, 70(4):579-86, Jun. 10, 2007. Epub Jan. 30, 2007.

(56) References Cited

OTHER PUBLICATIONS

Weide et al., "Direct injection of protamine-protected mRNA: results of a phase 1/2 vaccination trial in metastatic melanoma patients," J Immunother., 32(5):498-507, 2009.
Wyman et al., "Design, synthesis, and characterization of a cationic peptide that binds to nucleic acids and permeabilizes bilayers," *Biochemistry*, 36:3008-3017, 1997.
Xiong et al., "pH-responsive multi-PEGylated dual cationic nanoparticles enable charge modulations for safe gene delivery," *Chem Med Chem*, 2:1321-1327, 2007.
Yoshitomi et al., "Design of core-shell-type nanoparticles carrying stable radicals in the core," *Biomacromolecules*, 10:596-601, 2009.
Zhang et al., "Delivery of telomerase reverse transcriptase small interfering RNA in complex with positively charged single-walled carbon nanotubes suppresses tumor growth," *Clinical Cancer Research*, 12:4933-4939, 2006.
Zhang et al., "Personalized cancer vaccines: targeting the cancer mutanome," Vaccine 35:1094-1100, 2017.
Zhao et al., "N/P ratio significantly influences the transfection efficiency and cytotoxicity of a polyethylenimine/chitosan/DNA complex," Biol. Pharm. Bull., 32(4):706-710, 2009.
Zhou et al., "RNA melanoma vaccine: induction of antitumor immunity by human glycoprotein 100 mRNA immunization", *Human Gene Therapy*, 10:2719-2724, 1999.
Zimmermann et al., "Immunostimulatory DNA as adjuvant: efficacay of phosphodiester CpG oligonucleotides is enhanced by 3' sequence modifications", *Vaccine*, 21(9-10):990-5, 2003. (abstract only).
Zohra et al., "Effective delivery with enhanced translational activity synergistically accelerates mRNA-based transfection," *Biochem Biphys Res Commun*., 358(1):373-378, 2007.
U.S. Appl. No. 17/393,362, filed Aug. 3, 2021.
U.S. Appl. No. 16/555,881, filed Aug. 29, 2019.

* cited by examiner

RSV-F long (GC) R1691

GGGAGAAAGCUUACCAUGGAGCUGCCCAUCCUCAAGGCCAACGCCAUCACCACCAUCCUG
GCGGCCGUGACGUUCUGCUUCGCCAGCUCCCAGAACAUCACCGAGGAGUUCUACCAGAGC
ACCUGCUCCGCCGUCAGCAAGGGCUACCUGUCCGCCCUCCGGACCGGGUGGUACACGAGC
GUGAUCACCAUCGAGCUGUCCAACAUCAAGGAGAACAAGUGCAACGGCACCGACGCGAAG
GUGAAGCUGAUCAACCAGGAGCUCGACAAGUACAAGAACGCCGUCACCGAGCUGCAGCUG
CUCAUGCAGAGCACGACCGCCGCCAACAACCGCGCGCGGCGCGAGCUGCCGCGGUUCAUG
AACUACACCCUGAACAACACCAAGAAGACGAACGUGACCCUCUCCAAGAAGCGCAAGCGG
CGCUUCCUGGGGUUCCUGCUCGGCGUGGGGAGCGCCAUCGCCUCCGGCAUCGCCGUCAGC
AAGGUGCUGCACCUGGAGGGCGAGGUGAACAAGAUCAAGUCCGCCCUCCUGAGCACCAAC
AAGGCGGUCGUGUCCCUGAGCAACGGGGUGUCCGUCCUCACCAGCAAGGUGCUGGACCUG
AAGAACUACAUCGACAAGCAGCUCCUGCCCAUCGUGAACAAGCAGUCCUGCCGGAUCAGC
AACAUCGAGACGGUCAUCGAGUUCCAGCAGAAGAACAACCGCCUGCUCGAGAUCACCCGG
GAGUUCAGCGUGAACGCCGGCGUGACCACCCCCGUCUCCACGUACAUGCUGACCAACAGC
GAGCUGCUCUCCCUGAUCAACGACAUGCCCAUCACCAACGACCAGAAGAAGCUGAUGAGC
AACAACGUGCAGAUCGUGCGCCAGCAGUCCUACAGCAUCAUGUCCAUCAUCAAGGAGGAG
GUCCUCGCCUACGUGGUGCAGCUGCCGCUGUACGGGGUCAUCGACACCCCCUGCUGGAAG
CUCCACACGAGCCCCCUGUGCACCACCAACACCAAGGAGGGCUCCAACAUCUGCCUGACG
CGGACCGACCGCGGGUGGUACUGCGACAACGCCGGCAGCGUGUCCUUCUUCCCCCAGGCC
GAGACCUGCAAGGUCCAGAGCAACCGGGUGUUCUGCGACACCAUGAACUCCCUCACGCUG
CCGAGCGAGGUGAACCUGUGCAACGUCGACAUCUUCAACCCCAAGUACGACUGCAAGAUC
AUGACCUCCAAGACCGACGUGAGCUCCAGCGUGAUCACCUCCCUCGGCGCGAUCGUCAGC
UGCUACGGGAAGACGAAGUGCACCGCCAGCAACAAGAACCGCGGCAUCAUCAAGACCUUC
UCCAACGGGUGCGACUACGUGAGCAACAAGGGCGUGGACACCGUCUCCGUGGGCAACACC
CUGUACUACGUGAACAAGCAGGAGGGGAAGAGCCUGUACGUCAAGGGCGAGCCCAUCAUC
AACUUCUACGACCCCCUCGUGUUCCCGUCCGACGAGUUCGACGCCAGCAUCUCCCAGGUG
AACGAGAAGAUCAACCAGAGCCUGGCCUUCAUCCGGAAGUCCGACGAGCUGCUGCACCAC
GUCAACGCCGGGAAGAGCACGACCAACAUCAUGAUCACCACCAUCAUCAUCGUGAUCAUC
GUGAUCCUCCUGUCCCUGAUCGCGGUCGGCCUCCUGCUGUACUGCAAGGCCCGCAGCACG
CCCGUGACCCUCUCCAAGGACCAGCUGAGCGGGAUCAACAACAUCGCCUUCUCCAACUGA
GGACUAGUUAUAAGACUGACUAGCCCGAUGGGCCUCCCAACGGGCCCUCCUCCCCUCCUU
GCACCGAGAUUAAUAAAAAAAAAAAAAAAAAAAAAAAAAAAAAAAAAAAAAAAAAAAAAA
AAAAAAAAAAAAAAAAAAUGCAUCCCCCCCCCCCCCCCCCCCCCCCCCCCCCCCAAAGGC
UCUUUUCAGAGCCACCAGAAUU

Fig. 1

RSV-F long (GC) R2510

GGGGCGCUGCCUACGGAGGUGGCAGCCAUCUCCUUCUCGGCAUCAAGCUUACCAUGGAGC
UGCCCAUCCUCAAGGCCAACGCCAUCACCACCAUCCUGGCGGCCGUGACGUUCUGCUUCG
CCAGCUCCCAGAACAUCACCGAGGAGUUCUACCAGAGCACCUGCUCCGCCGUCAGCAAGG
GCUACCUGUCCGCCCUCCGGACCGGGUGGUACACGAGCGUGAUCACCAUCGAGCUGUCCA
ACAUCAAGGAGAACAAGUGCAACGGCACCGACGCGAAGGUGAAGCUGAUCAACCAGGAGC
UCGACAAGUACAAGAACGCCGUCACCGAGCUGCAGCUGCUCAUGCAGAGCACGACCGCCG
CCAACAACCGCGCGCGGCGCGAGCUGCCGCGGUUCAUGAACUACACCCUGAACAACACCA
AGAAGACGAACGUGACCCUCUCCAAGAAGCGCAAGCGGCGCUUCCUGGGGUUCCUGCUCG
GCGUGGGGAGCGCCAUCGCCUCCGGCAUCGCCGUCAGCAAGGUGCUGCACCUGGAGGGCG
AGGUGAACAAGAUCAAGUCCGCCCUCCUGAGCACCAACAAGGCGGUCGUGUCCCUGAGCA
ACGGGGUGUCCGUCCUCACCAGCAAGGUGCUGGACCUGAAGAACUACAUCGACAAGCAGC
UCCUGCCCAUCGUGAACAAGCAGUCCUGCCGGAUCAGCAACAUCGAGACGGUCAUCGAGU
UCCAGCAGAAGAACAACCGCCUGCUCGAGAUCACCCGGGAGUUCAGCGUGAACGCCGGCG
UGACCACCCCCGUCUCCACGUACAUGCUGACCAACAGCGAGCUGCUCUCCCUGAUCAACG
ACAUGCCCAUCACCAACGACCAGAAGAAGCUGAUGAGCAACAACGUGCAGAUCGUGCGCC
AGCAGUCCUACAGCAUCAUGUCCAUCAUCAAGGAGGAGGUCCUCGCCUACGUGGUGCAGC
UGCCGCUGUACGGGGUCAUCGACACCCCCUGCUGGAAGCUCCACACGAGCCCCCUGUGCA
CCACCAACACCAAGGAGGGCUCCAACAUCUGCCUGACGCGGACCGACCGCGGGUGGUACU
GCGACAACGCCGGCAGCGUGUCCUUCUUCCCCCAGGCCGAGACCUGCAAGGUCCAGAGCA
ACCGGGUGUUCUGCGACACCAUGAACUCCCUCACGCUGCCGAGCGAGGUGAACCUGUGCA
ACGUCGACAUCUUCAACCCCAAGUACGACUGCAAGAUCAUGACCUCCAAGACCGACGUGA
GCUCCAGCGUGAUCACCUCCCUCGGCGCGAUCGUCAGCUGCUACGGGAAGACGAAGUGCA
CCGCCAGCAACAAGAACCGCGGCAUCAUCAAGACCUUCUCCAACGGGUGCGACUACGUGA
GCAACAAGGGCGUGGACACCGUCUCCGUGGGCAACACCCUGUACUACGUGAACAAGCAGG
AGGGGAAGAGCCUGUACGUCAAGGGCGAGCCCAUCAUCAACUUCUACGACCCCCUCGUGU
UCCCGUCCGACGAGUUCGACGCCAGCAUCUCCCAGGUGAACGAGAAGAUCAACCAGAGCC
UGGCCUUCAUCCGGAAGUCCGACGAGCUGCUGCACCACGUCAACGCCGGGAAGAGCACGA
CCAACAUCAUGAUCACCACCAUCAUCAUCGUGAUCAUCGUGAUCCUCCUGUCCCUGAUCG
CGGUCGGCCUCCUGCUGUACUGCAAGGCCCGCAGCACGCCCGUGACCCUCUCCAAGGACC
AGCUGAGCGGGAUCAACAACAUCGCCUUCUCCAACUGAGGACUAGUGCAUCACAUUUAAA
AGCAUCUCAGCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAAAUUUCUUUA
AUCAUUUUGCCUCUUUUCUCUGUGCUUCAAUUAAUAAAAAAUGGAAAGAACCUAGAUCUA
AAAAAAAAAAAAAAAAAAAAAAAAAAAAAAAAAAAAAAAAAAAAAAAAAAAAAAAAAAAA
AAAUGCAUCCCCCCCCCCCCCCCCCCCCCCCCCCCCCCCAAAGGCUCUUUUCAGAGCCAC
CAGAAUU

Fig. 2

RSV-Fdel554-574 long (GC) R2821

GGGGCGCUGCCUACGGAGGUGGCAGCCAUCUCCUUCUCGGCAUCAAGCUUACCAUGGAGC
UGCCCAUCCUCAAGGCCAACGCCAUCACCACCAUCCUGGCGGCCGUGACGUUCUGCUUCG
CCAGCUCCCAGAACAUCACCGAGGAGUUCUACCAGAGCACCUGCUCCGCCGUCAGCAAGG
GCUACCUGUCCGCCCUCCGGACCGGGUGGUACACGAGCGUGAUCACCAUCGAGCUGUCCA
ACAUCAAGGAGAACAAGUGCAACGGCACCGACGCGAAGGUGAAGCUGAUCAACCAGGAGC
UCGACAAGUACAAGAACGCCGUCACCGAGCUGCAGCUGCUCAUGCAGAGCACGACCGCCG
CCAACAACCGCGCGCGGCGCGAGCUGCCGCGGUUCAUGAACUACACCCUGAACAACACCA
AGAAGACGAACGUGACCCUCUCCAAGAAGCGCAAGCGGCGCUUCCUGGGGUUCCUGCUCG
GCGUGGGGAGCGCCAUCGCCUCCGGCAUCGCCGUCAGCAAGGUGCUGCACCUGGAGGGCG
AGGUGAACAAGAUCAAGUCCGCCCUCCUGAGCACCAACAAGGCGGUCGUGUCCCUGAGCA
ACGGGGUGUCCGUCCUCACCAGCAAGGUGCUGGACCUGAAGAACUACAUCGACAAGCAGC
UCCUGCCCAUCGUGAACAAGCAGUCCUGCCGGAUCAGCAACAUCGAGACGGUCAUCGAGU
UCCAGCAGAAGAACAACCGCCUGCUCGAGAUCACCCGGGAGUUCAGCGUGAACGCCGGCG
UGACCACCCCCGUCUCCACGUACAUGCUGACCAACAGCGAGCUGCUCUCCCUGAUCAACG
ACAUGCCCAUCACCAACGACCAGAAGAAGCUGAUGAGCAACAACGUGCAGAUCGUGCGCC
AGCAGUCCUACAGCAUCAUGUCCAUCAUCAAGGAGGAGGUCCUCGCCUACGUGGUGCAGC
UGCCGCUGUACGGGGUCAUCGACACCCCCUGCUGGAAGCUCCACACGAGCCCCCUGUGCA
CCACCAACACCAAGGAGGGCUCCAACAUCUGCCUGACGCGGACCGACCGCGGGUGGUACU
GCGACAACGCCGGCAGCGUGUCCUUCUUCCCCCAGGCCGAGACCUGCAAGGUCCAGAGCA
ACCGGGUGUUCUGCGACACCAUGAACUCCCUCACGCUGCCGAGCGAGGUGAACCUGUGCA
ACGUCGACAUCUUCAACCCCAAGUACGACUGCAAGAUCAUGACCUCCAAGACCGACGUGA
GCUCCAGCGUGAUCACCUCCCUCGGCGCGAUCGUCAGCUGCUACGGGAAGACGAAGUGCA
CCGCCAGCAACAAGAACCGCGGCAUCAUCAAGACCUUCUCCAACGGGUGCGACUACGUGA
GCAACAAGGGCGUGGACACCGUCUCCGUGGGCAACACCCUGUACUACGUGAACAAGCAGG
AGGGGAAGAGCCUGUACGUCAAGGGCGAGCCCAUCAUCAACUUCUACGACCCCCUCGUGU
UCCCGUCCGACGAGUUCGACGCCAGCAUCUCCCAGGUGAACGAGAAGAUCAACCAGAGCC
UGGCCUUCAUCCGGAAGUCCGACGAGCUGCUGCACCACGUCAACGCCGGGAAGAGCACGA
CCAACAUCAUGAUCACCACCAUCAUCAUCGUGAUCAUCGUGAUCCUCCUGUCCCUGAUCG
CGGUCGGCCUCCUGCUGUACUGCAAGGCCCGCUGAGGACUAGUGCAUCACAUUUAAAAGC
AUCUCAGCCUACCAUGAGAAUAAGAGAAAGAAAAUGAAGAUCAAUAGCUUAUUCAUCUCU
UUUUCUUUUUCGUUGGUGUAAAGCCAACACCCUGUCUAAAAAACAUAAAUUUCUUUAAUC
AUUUUGCCUCUUUUCUCUGUGCUUCAAUUAAUAAAAAAUGGAAAGAACCUAGAUCUAAAA
AAAAAAAAAAAAAAAAAAAAAAAAAAAAAAAAAAAAAAAAAAAAAAAAAAAAAAAAAAAA
UGCAUCCCCCCCCCCCCCCCCCCCCCCCCCCCCCCCAAAGGCUCUUUUCAGAGCCACCAG
AAUU

Fig. 3

RSV-N (GC) R2831

GGGGCGCUGCCUACGGAGGUGGCAGCCAUCUCCUUCUCGGCAUCAAGCUUACCAUGGCCC
UGAGCAAGGUGAAGCUCAACGACACCCUGAACAAGGACCAGCUGCUCUCCAGCUCCAAGU
ACACCAUCCAGCGCAGCACGGGCGACUCCAUCGACACCCCCAACUACGACGUCCAGAAGC
ACAUCAACAAGCUGUGCGGGAUGCUGCUCAUCACCGAGGACGCCAACCACAAGUUCACCG
GCCUGAUCGGGAUGCUGUACGCGAUGAGCCGGCUCGGCCGCGAGGACACGAUCAAGAUCC
UGCGGGACGCCGGGUACCACGUGAAGGCCAACGGCGUGGACGUCACCACCCACCGCCAGG
ACAUCAACGGCAAGGAGAUGAAGUUCGAGGUGCUGACCCUCGCCUCCCUGACGACCGAGA
UCCAGAUCAACAUCGAGAUCGAGAGCCGGAAGUCCUACAAGAAGAUGCUGAAGGAGAUGG
GGGAGGUGGCCCCGGAGUACCGCCACGACAGCCCCGACUGCGGCAUGAUCAUCCUCUGCA
UCGCGGCCCUGGUCAUCACCAAGCUGGCCGCCGGGGACCGGUCCGGCCUCACCGCGGUGA
UCCGCCGGGCCAACAACGUGCUGAAGAACGAGAUGAAGCGCUACAAGGGGCUGCUCCCCA
AGGACAUCGCCAACAGCUUCUACGAGGUCUUCGAGAAGCACCCCCACUUCAUCGACGUGU
UCGUGCACUUCGGCAUCGCCCAGUCCAGCACGCGGGGCGGGUCCCGCGUCGAGGGCAUCU
UCGCCGGGCUGUUCAUGAACGCGUACGGCGCCGGCCAGGUGAUGCUGCGGUGGGGCGUGC
UCGCCAAGAGCGUCAAGAACAUCAUGCUGGGGCACGCCUCCGUGCAGGCCGAGAUGGAGC
AGGUGGUCGAGGUGUACGAGUACGCGCAGAAGCUGGGCGGCGAGGCCGGGUUCUACCACA
UCCUCAACAACCCGAAGGCCAGCCUGCUGUCCCUCACCCAGUUCCCGCACUUCAGCAGCG
UGGUCCUGGGGAACGCCGCCGGCCUGGGGAUCAUGGGCGAGUACCGCGGGACCCCGCGGA
ACCAGGACCUCUACGACGCGGCCAAGGCCUACGCCGAGCAGCUGAAGGAGAACGGCGUGA
UCAACUACUCCGUGCUGGACCUCACCGCCGAGGAGCUGGAGGCGAUCAAGCACCAGCUGA
ACCCCAAGGACAACGACGUCGAGCUCUGAGGACUAGUGCAUCACAUUUAAAAGCAUCUCA
GCCUACCAUGAGAAUAAGAGAAAGAAAAUGAAGAUCAAUAGCUUAUUCAUCUCUUUUUCU
UUUUCGUUGGUGUAAAGCCAACACCCUGUCUAAAAAACAUAAAUUUCUUUAAUCAUUUUG
CCUCUUUUCUCUGUGCUUCAAUUAAUAAAAAAUGGAAAGAACCUAGAUCUAAAAAAAAAA
AAAAAAAAAAAAAAAAAAAAAAAAAAAAAAAAAAAAAAAAAAAAAAAAAAAAAAUGCAUC
CCCCCCCCCCCCCCCCCCCCCCCCCCCCCCAAAGGCUCUUUUCAGAGCCACCAGAAUU

Fig. 4

RSV-M2-1 (GC) R2833

GGGGCGCUGCCUACGGAGGUGGCAGCCAUCUCCUUCUCGGCAUCAAGCUUACCAUGAGCC
GCCGGAACCCCUGCAAGUUCGAGAUCCGCGGCCACUGCCUGAACGGGAAGCGGUGCCACU
UCUCCCACAACUACUUCGAGUGGCCGCCCCACGCCCUCCUGGUGCGCCAGAACUUCAUGC
UGAACCGGAUCCUCAAGAGCAUGGACAAGUCCAUCGACACCCUGAGCGAGAUCUCCGGCG
CCGCGGAGCUGGACCGCACCGAGGAGUACGCCCUCGGGGUCGUGGGCGUGCUGGAGAGCU
ACAUCGGGUCCAUCAACAACAUCACGAAGCAGAGCGCCUGCGUCGCCAUGUCCAAGCUGC
UCACCGAGCUGAACAGCGACGACAUCAAGAAGCUGCGGGACAACGAGGAGCUCAACUCCC
CCAAGAUCCGCGUGUACAACACCGUGAUCAGCUACAUCGAGUCCAACCGGAAGAACAACA
AGCAGACCAUCCACCUGCUGAAGCGCCUCCCCGCCGACGUCCUGAAGAAGACGAUCAAGA
ACACCCUGGACAUCCACAAGAGCAUCACCAUCAACAACCCGAAGGAGCUCACCGUGUCCG
ACACGAACGACCACGCGAAGAACAACGACACCACCUGAGGACUAGUGCAUCACAUUUAAA
AGCAUCUCAGCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAAAUUUCUUUA
AUCAUUUUGCCUCUUUUCUCUGUGCUUCAAUUAAUAAAAAAUGGAAAGAACCUAGAUCUA
AAAAAAAAAAAAAAAAAAAAAAAAAAAAAAAAAAAAAAAAAAAAAAAAAAAAAAAAAAAA
AAAUGCAUCCCCCCCCCCCCCCCCCCCCCCCCCCCCCCCAAAGGCUCUUUUCAGAGCCAC
CAGAAUU

Fig. 5

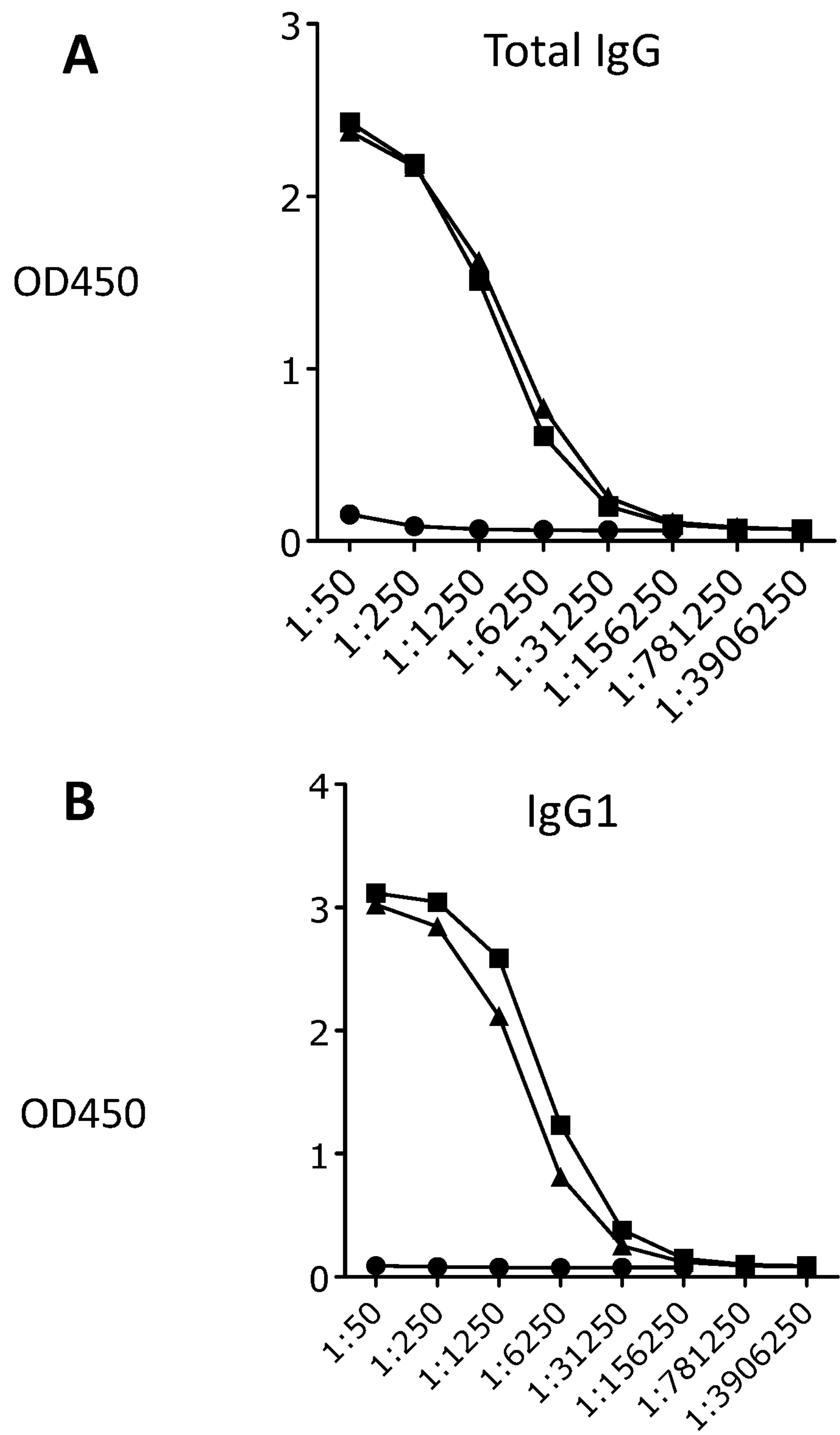
Figs. 6A-B

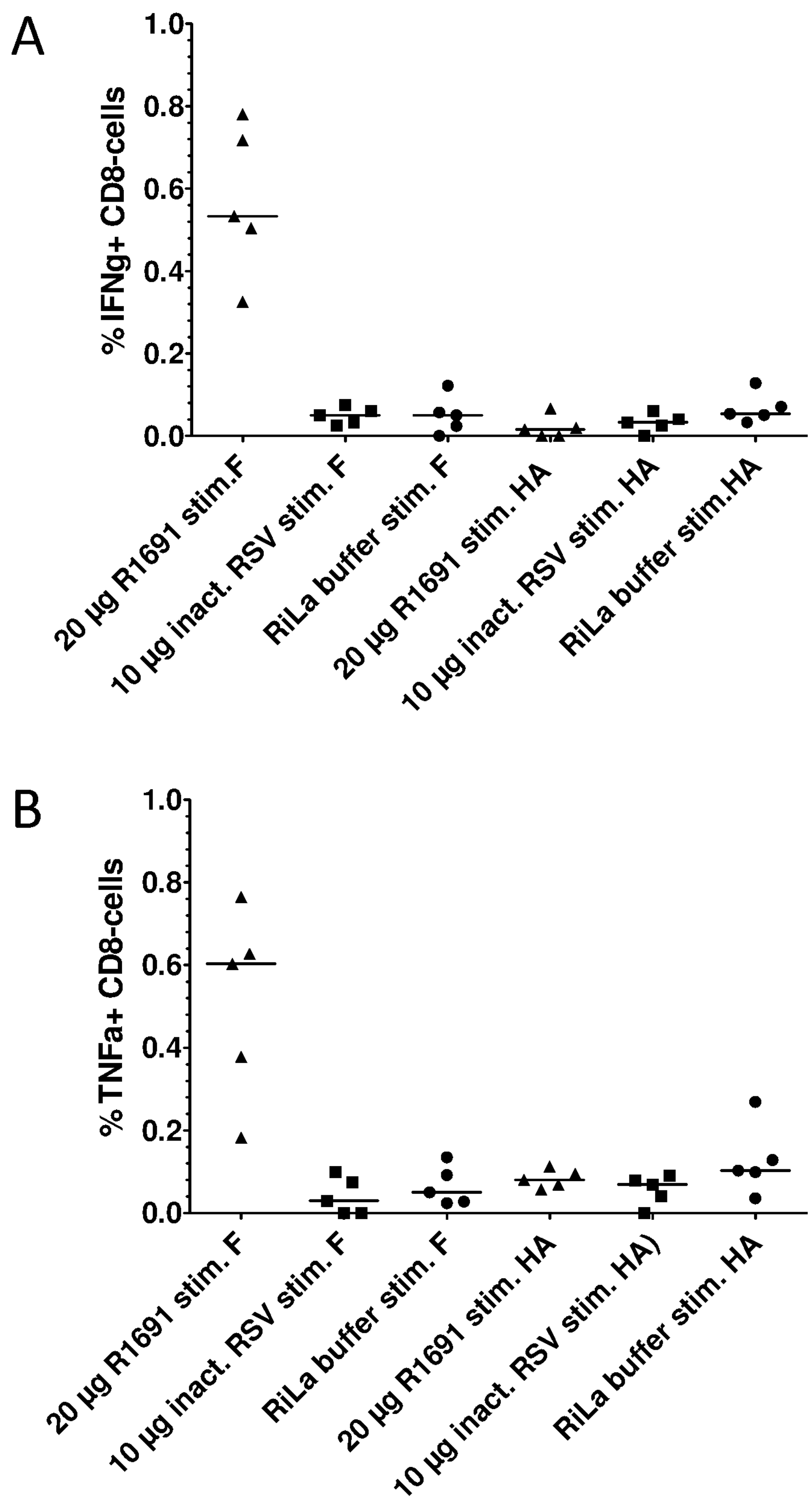
Figs. 8A-B

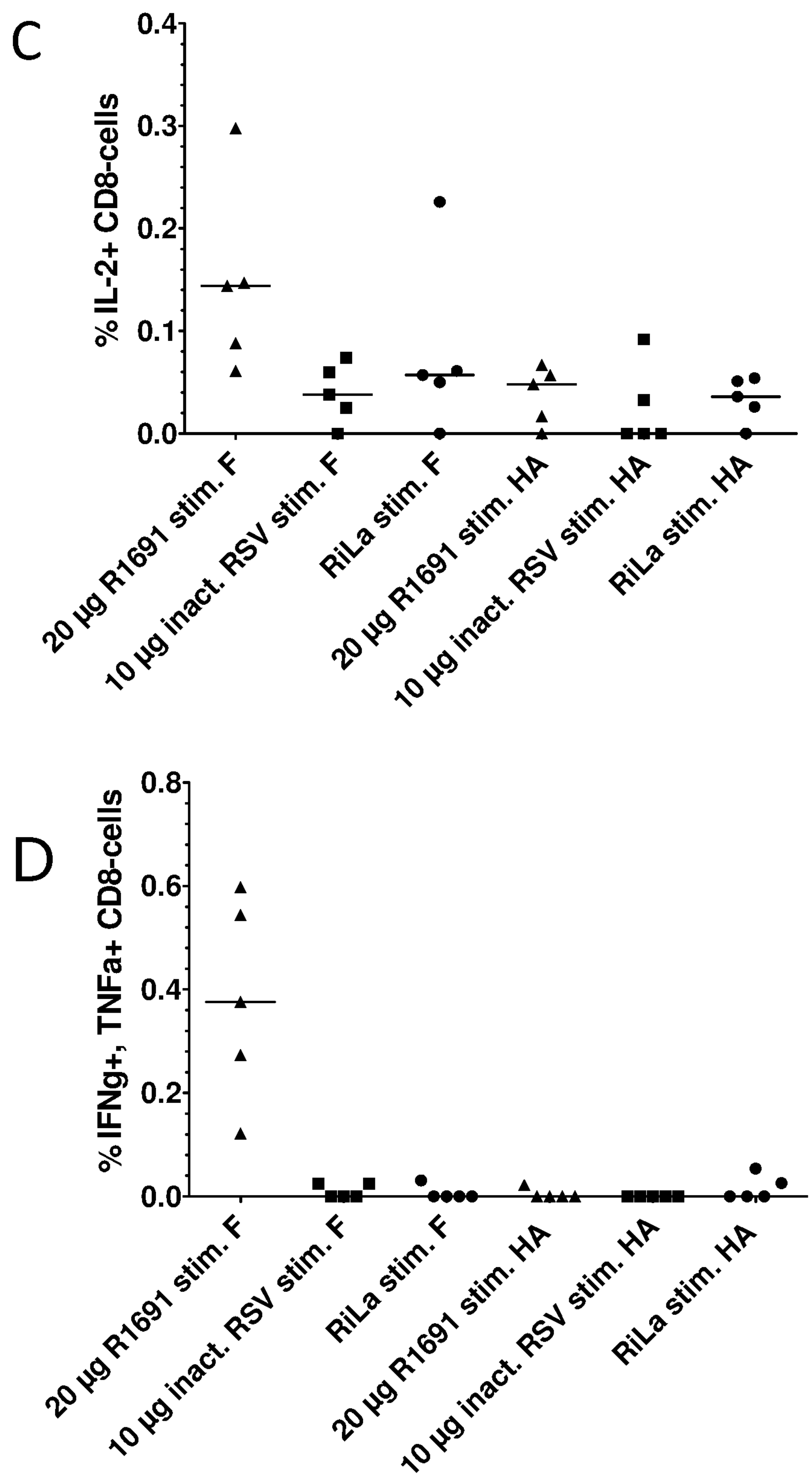
Figs. 8C-D

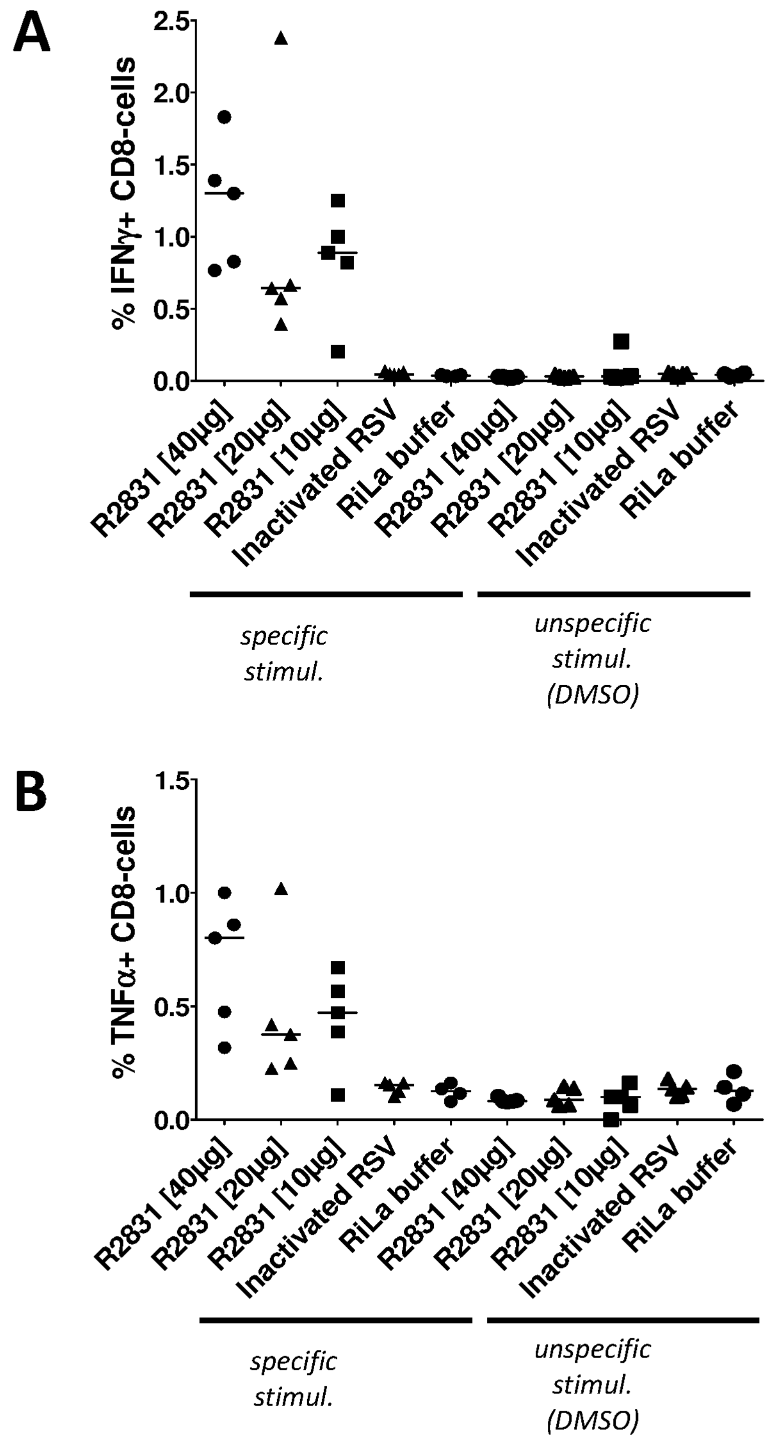
Figs. 9A-B

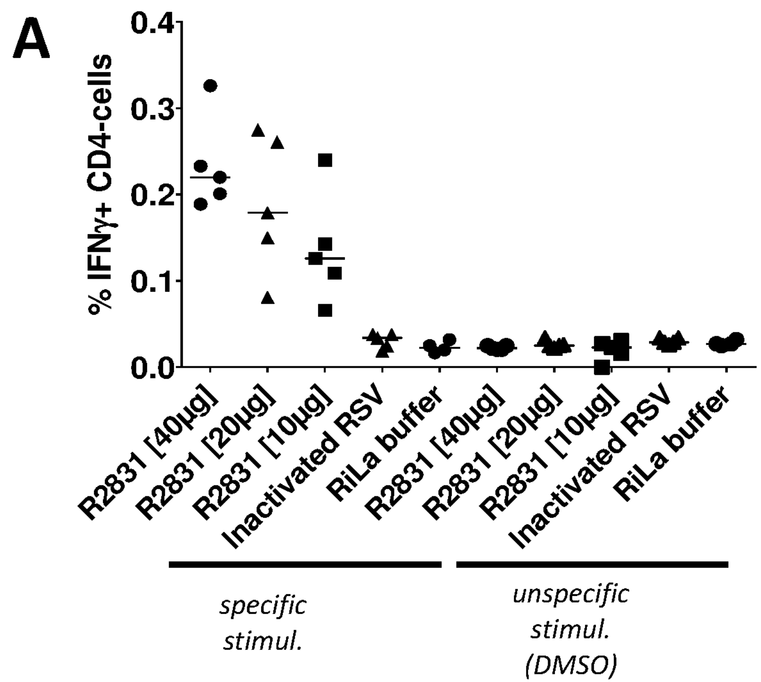
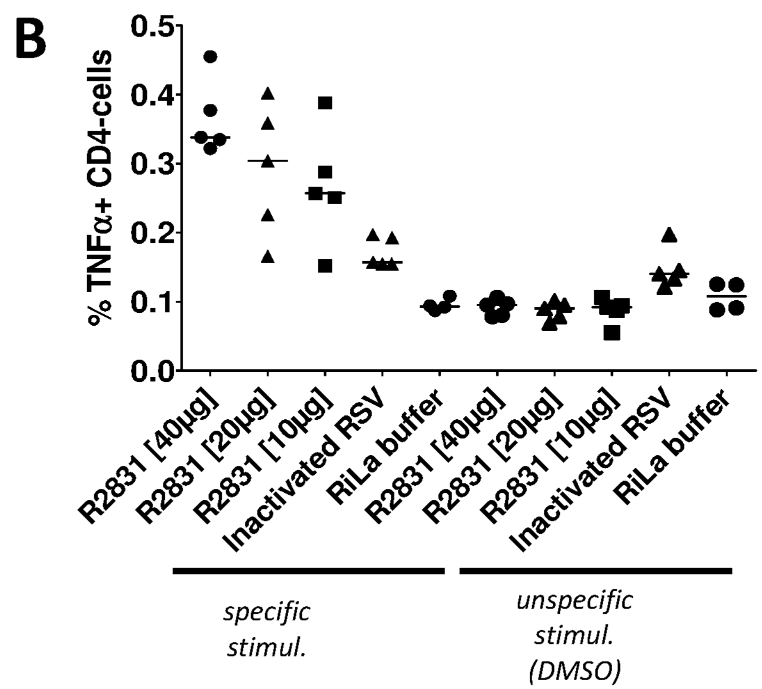
Figs. 10A-B

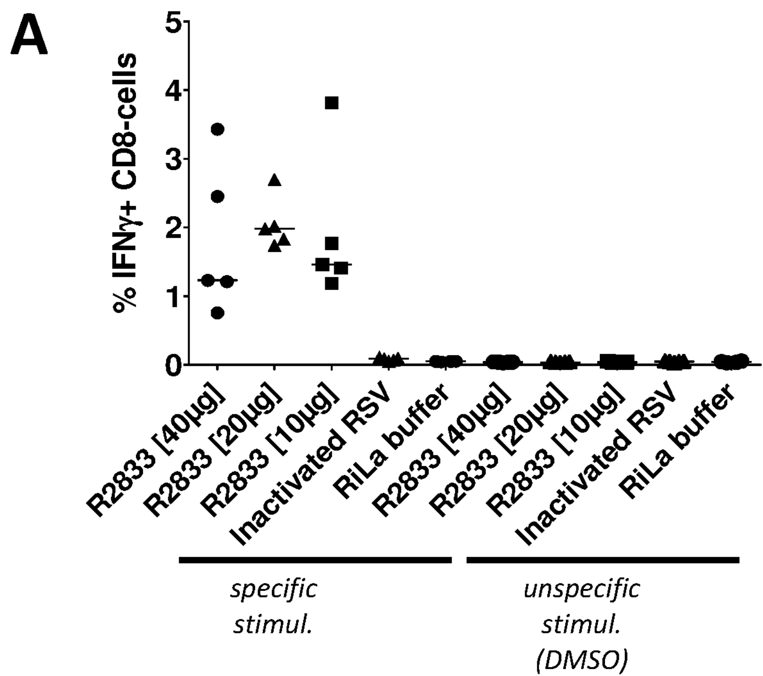
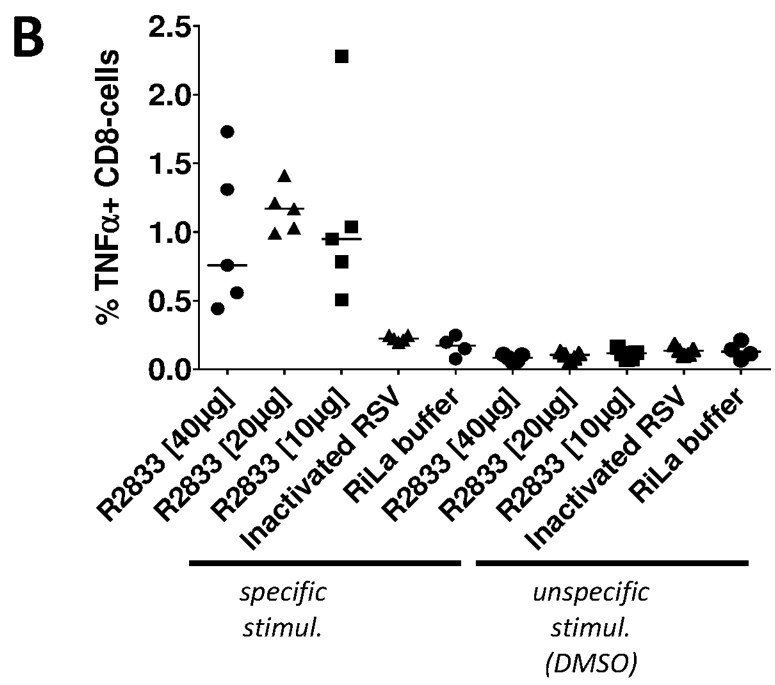
Figs. 11A-B

A
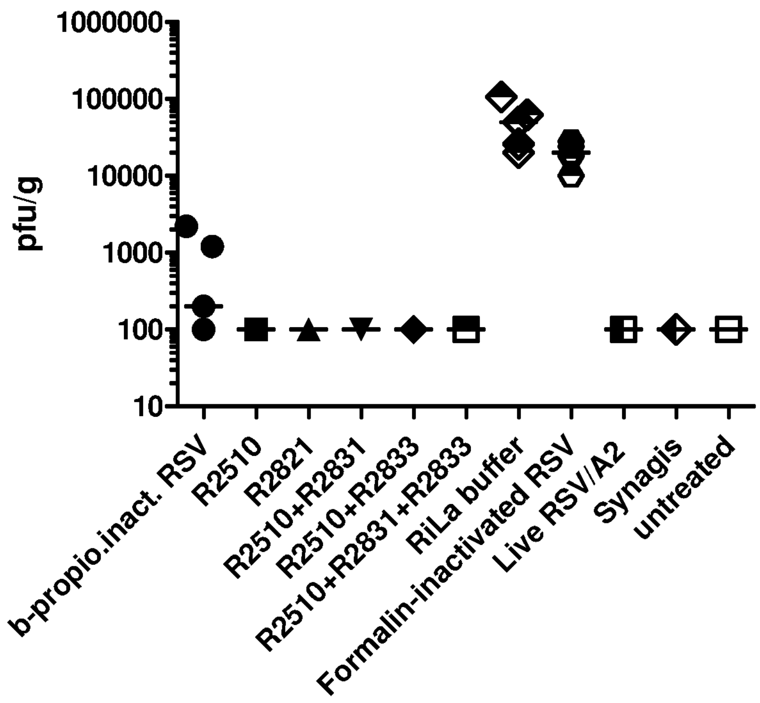
B
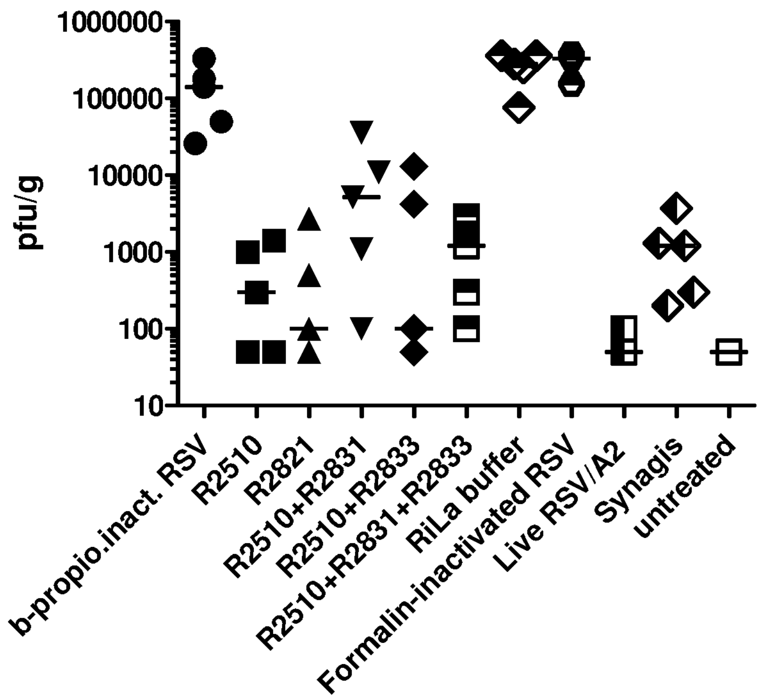
Figs. 14A-B

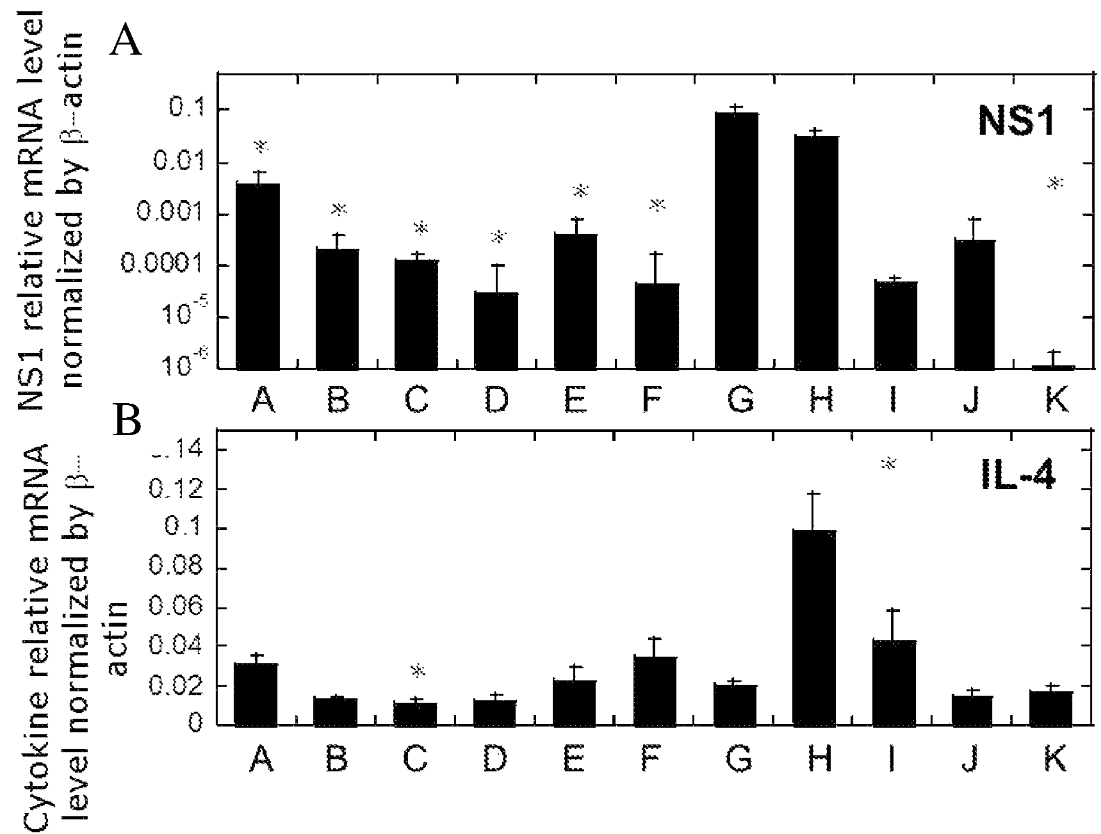
Figs. 16A-B

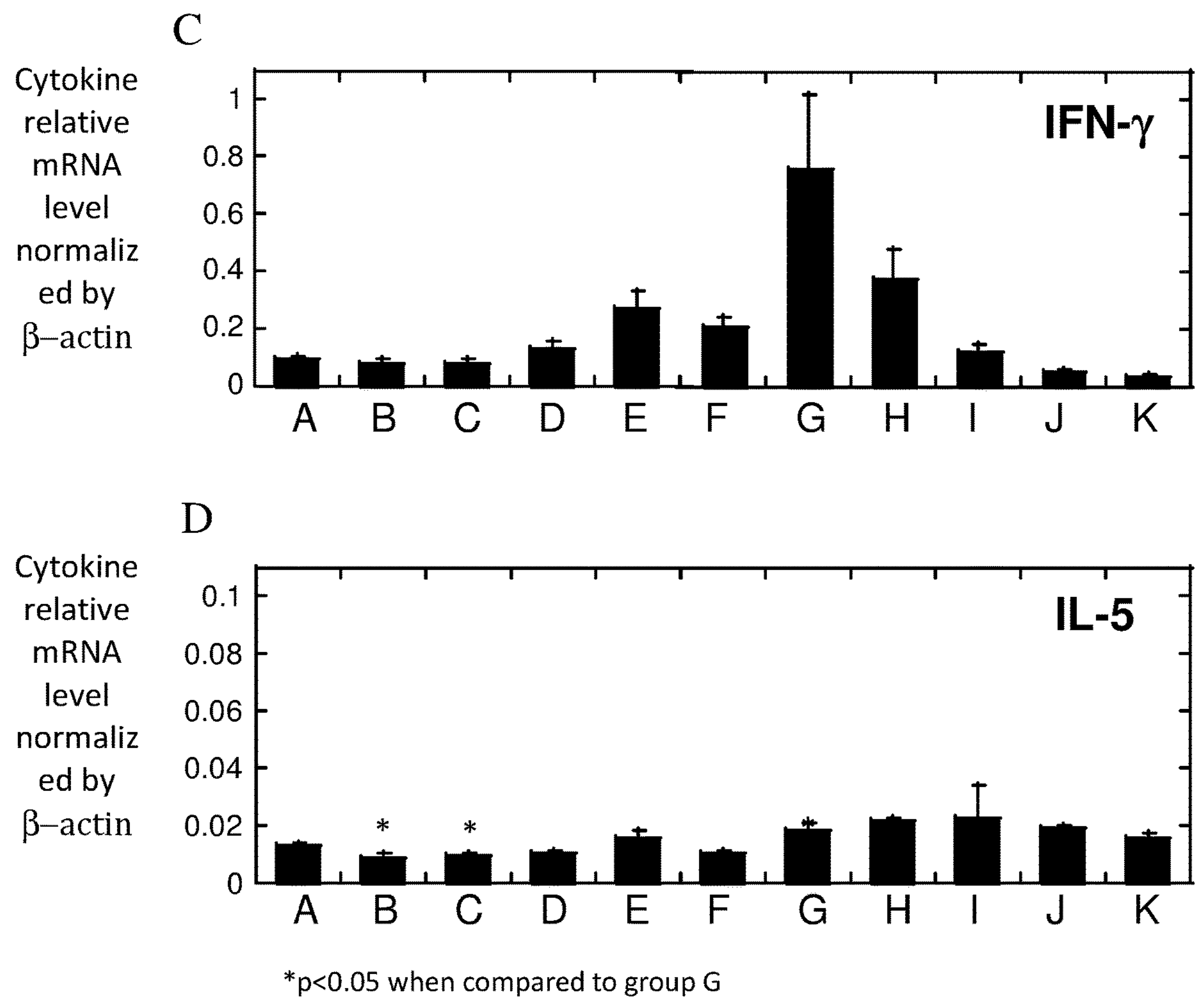
Figs. 16C-D

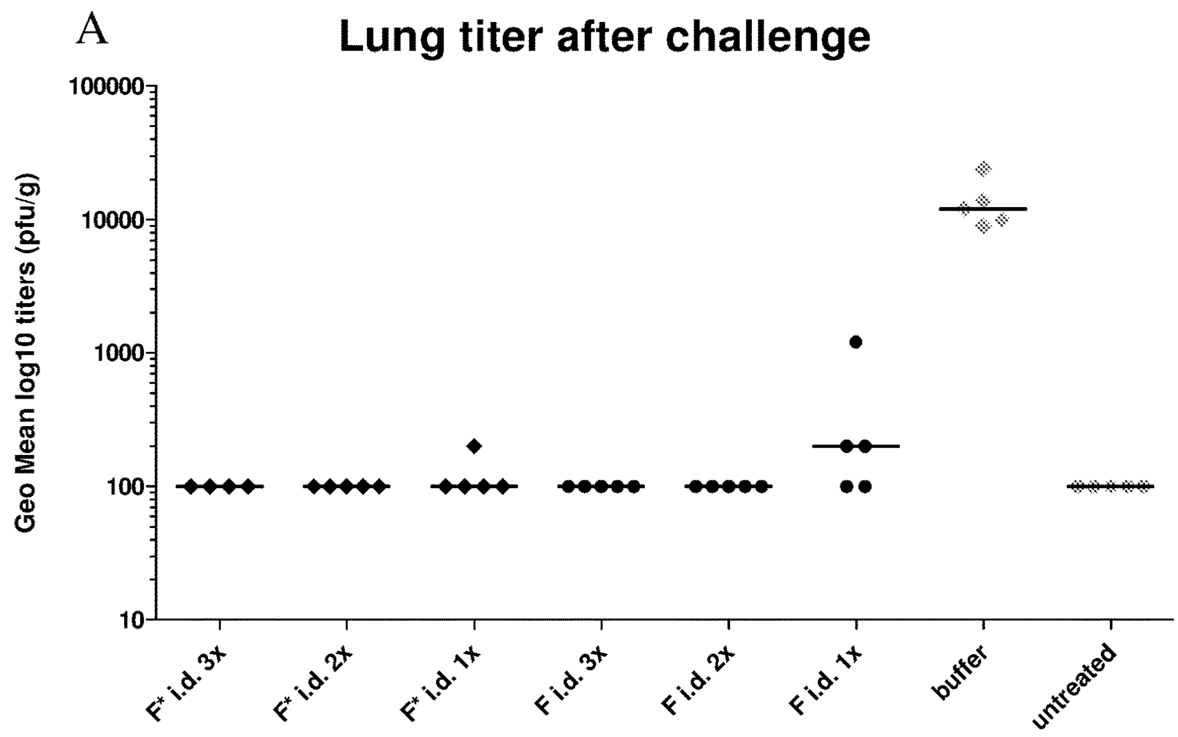
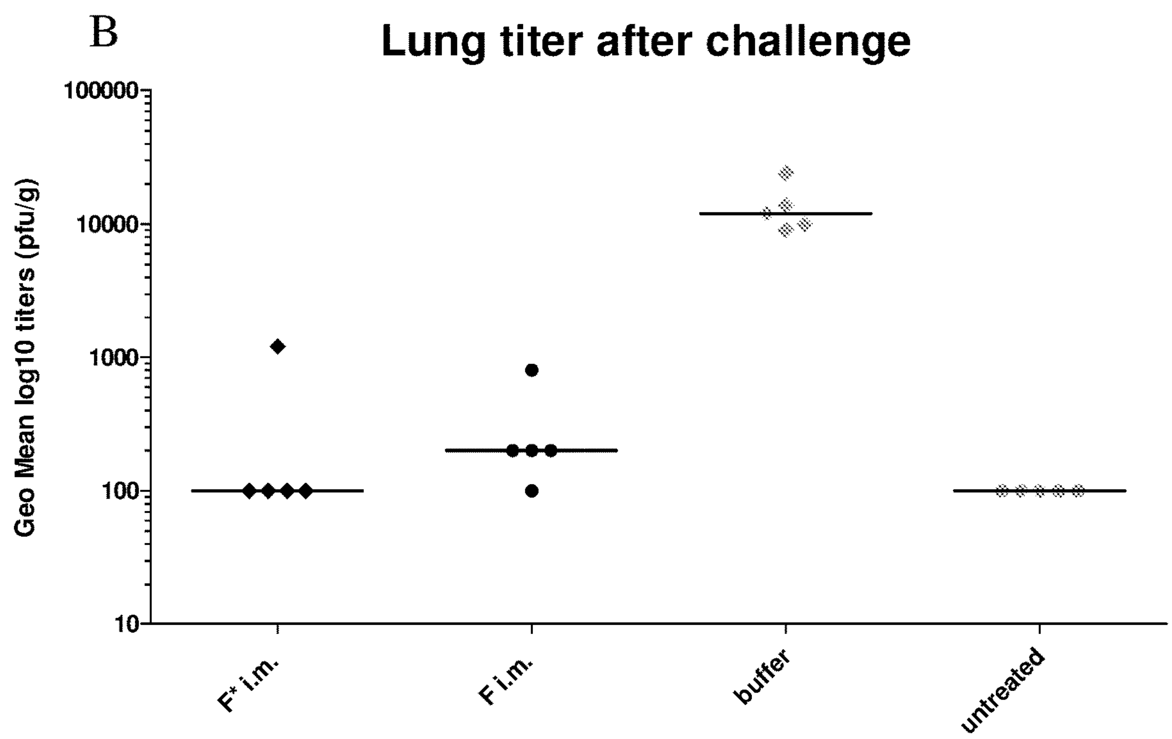
Figs. 17A-B

RESPIRATORY SYNCYTIAL VIRUS (RSV) VACCINE

The present application is a continuation of U.S. application Ser. No. 16/168,747, filed Oct. 23, 2018, which is a continuation of U.S. application Ser. No. 15/488,815, filed Apr. 17, 2017, now U.S. Pat. No. 10,150,797, which is a continuation of U.S. application Ser. No. 15/048,439, filed Feb. 19, 2016, now U.S. Pat. No. 9,688,729, which is a continuation of International Application No. PCT/EP2014/002301, filed Aug. 21, 2014, which claims priority benefit of European Application No. PCT/EP2013/002518, filed Aug. 21, 2013, the entire text of each of the above referenced disclosures being specifically incorporated herein by reference.

BACKGROUND OF THE INVENTION

The present invention relates to an mRNA sequence, comprising a coding region, encoding at least one antigenic peptide or protein of Respiratory syncytial virus (RSV) or a fragment, variant or derivative thereof. Additionally the present invention relates to a composition comprising a plurality of mRNA sequences comprising a coding region, encoding at least one antigenic peptide or protein of Respiratory syncytial virus (RSV) or a fragment, variant or derivative thereof.

Furthermore it also discloses the use of the mRNA sequence or the composition comprising a plurality of mRNA sequences for the preparation of a pharmaceutical composition, especially a vaccine, e.g. for use in the prophylaxis or treatment of RSV infections. The present invention further describes a method of treatment or prophylaxis of RSV infections using the mRNA sequence.

The global medical need and economic impact of RSV is very high. It is the most important cause of acute lower respiratory tract infections (ALRIs) that result in hospital visits during infancy and early childhood. For example, in the United States, more than 60% of infants are infected by RSV during their first RSV season, and nearly all have been infected by 2-3 years of age. Approximately 2.1 million US children less than 5 years of age are treated for RSV disease each year: 3% as inpatients, 25% in emergency departments, and 73% in pediatric practices. Globally, among children less than five years of age, RSV causes an estimated 33.8 million ALRIs each year (more than 22% of all ALRIs), resulting in 66 000-199 000 deaths, 99% of which occur in developing countries. RSV is also a common cause of respiratory disease among the elderly, resulting in as many hospitalizations as influenza in a heavily influenza-immunized population. RSV spreads by respiratory droplets and close contact with infected persons or contaminated objects. In temperate climates, there is an annual winter epidemic. Infants are at highest risk for severe RSV disease in their first 6 months, and hospitalization peaks at 2-3 months of age. Preterm birth and cardiopulmonary disease are risk factors for severe RSV disease. RSV infection of infants elicits partially protective immunity, which appears to wane more rapidly than immunity against most other respiratory viruses. Most children infected with RSV during their first year are re-infected the next year, generally with less severe disease. Re-infections continue throughout life, often with upper respiratory tract symptoms, and sometimes with lower respiratory tract or sinus involvement. Recommended treatment of RSV bronchiolitis consists primarily of respiratory support and hydration. No specific anti-viral therapy is recommended. The neutralizing monoclonal antibody Palivizumab is used for prophylaxis of infants at highest risk for severe infection but is too expensive and impractical for universal use. Currently, there is no licensed RSV vaccine, and developing a safe and effective RSV vaccine is a global public health priority.

In a vaccine trial in the 1960s, infants and young children were immunized with a formalin-inactivated whole virion RSV preparation (FIRSV) or an equivalent paramyxovirus preparation (FIPIV). Five percent of the subjects who were immunized with FI-PIV and then naturally infected by RSV during the next RSV season were hospitalized; 80% of those who were immunized with FI-RSV and then infected by RSV were hospitalized, and two children died. This enhancement of an RSV infection due to vaccination is a specific problem for the development of vaccines against RSV infections (reviewed in Shaw et al. Curr Opin Virol. 2013 June; 3(3):332-42. doi: 10.1016/j.coviro.2013.05.003. Epub 2013 May 30).

Therefore, Respiratory syncytial virus (RSV) infections are the greatest remaining unmet infant vaccine need in developed countries and an important unmet infant vaccine need worldwide. More than 40 years of effort have not yet resulted in a licensed RSV vaccine for humans.

In summary, RSV which belongs to the virus family of Paramyxoviridae, is one of the most contagious pathogens and makes a substantial contribution to severe respiratory tract infections in infants, the elderly and immunocompromised patients.

As mentioned above, currently a humanised monoclonal antibody against the viral surface F protein is the only prophylactic product on the market which is recommended for infants considered at high risk including pre-term infants and infants with chronic lung disease (The IMpact-RSV Study Group. 1998. Palivizumab, a Humanized Respiratory Syncytial Virus Monoclonal Antibody, Reduces Hospitalization From Respiratory Syncytial Virus Infection in High-risk Infants. Pediatrics, 102(3), S.531-537., Tablan et al. 2003. Guidelines for preventing health-care-associated pneumonia, 2003: recommendations of CDC and the Healthcare Infection Control Practices Advisory Committee. MMWR. Recommendations and Reports: Morbidity and Mortality Weekly Report. Recommendations and Reports/ Centers for Disease Control, 53(RR-3), S.1-36).

Recent studies with animal models demonstrated that sufficient amounts of neutralising antibodies targeting RSV F protein limit viral replication leading to a less severe course of disease (Singh, S. R. et al., 2007. Immunogenicity and efficacy of recombinant RSV-F vaccine in a mouse model. Vaccine, 25(33), S.6211-6223., Zhan, X. et al., 2007. Respiratory syncytial virus (RSV) F protein expressed by recombinant Sendai virus elicits B-cell and T-cell responses in cotton rats and confers protection against RSV subtypes A and B. Vaccine, 25(52), S.8782-8793., Vaughan, K., et al., 2005. DNA immunization against respiratory syncytial virus (RSV) in infant rhesus monkeys. Vaccine, 23(22), S.2928-2942).

Moreover, it could be shown that a balanced regulatory and effector T cell function is required for viral clearance and reduction of severity of illness (Liu, J. et al., 2010. Epitope-specific regulatory CD4 T cells reduce virus-induced illness while preserving CD8 T-cell effector function at the site of infection. Journal of Virology, 84(20), S.10501-10509).

Despite the above mentioned humanised monoclonal antibody, live-attenuated vaccine viruses were developed which elicit a strong immune response, but which are not recommended for use in the specific target groups (infants, children, the elderly and immunocompromised patients). Also, DNA vectors expressing RSV F protein which bears B-cell epitopes were used to induce the production of neutralizing antibodies. In this context, WO 2008/077527 and WO 96/040945 disclose vectors comprising DNA sequences encoding RSV F protein for the use as vaccines. However, the use of DNA as a vaccine may be dangerous due to unwanted insertion into the genome, possibly leading to interruption of functional genes and cancer or the formation of anti-DNA antibodies.

Therefore it is the object of the underlying invention to provide an mRNA sequence coding for antigenic peptides or proteins of Respiratory syncytial virus (RSV) for the use as vaccine for prophylaxis or treatment of RSV infections, particularly in infants, the elderly and immunocompromised patients.

These objects are solved by the subject matter of the attached claims. Particularly, the objects underlying the present invention are solved according to a first aspect by an inventive mRNA sequence comprising a coding region, encoding at least one antigenic peptide or protein of Respiratory syncytial virus (RSV) or a fragment, variant or derivative thereof.

For the sake of clarity and readability the following scientific background information and definitions are provided. Any technical features disclosed thereby can be part of each and every embodiment of the invention. Additional definitions and explanations can be provided in the context of this disclosure.

Immune system: The immune system may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immune response: An immune response may typically either be a specific reaction of the adaptive immune system to a particular antigen (so called specific or adaptive immune response) or an unspecific reaction of the innate immune system (so called unspecific or innate immune response). The invention relates to the core to specific reactions (adaptive immune responses) of the adaptive immune system. Particularly, it relates to adaptive immune responses to infections by viruses like e.g. RSV infections. However, this specific response can be supported by an additional unspecific reaction (innate immune response). Therefore, the invention also relates to a compound for simultaneous stimulation of the innate and the adaptive immune system to evoke an efficient adaptive immune response.

Adaptive immune system: The adaptive immune system is composed of highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Adaptive immune response: The adaptive immune response is typically understood to be antigen-specific. Antigen specificity allows for the generation of responses that are tailored to specific antigens, pathogens or pathogen-infected cells. The ability to mount these tailored responses is maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Cellular immunity/cellular immune response: Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

Humoral immunity/humoral immune response: Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Innate immune system: The innate immune system, also known as non-specific immune system, comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Adjuvant/adjuvant component: An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof.

The term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favourably modulate cytokine expression/secretion, antigen presentation, type of immune response etc.

Immunostimulatory RNA: An immunostimulatory RNA (isRNA) in the context of the invention may typically be a RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

Antigen: According to the present invention, the term "antigen" refers typically to a substance which may be recognized by the immune system and may be capable of triggering an antigen-specific immune response, e.g. by formation of antibodies or antigen-specific T-cells as part of an adaptive immune response. An antigen may be a protein or peptide. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by CD8+ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. $CD4^+$ T cells bind to a MHC class II molecule and $CD8^+$ T cells to a MHC class I molecule. MHC class I and MHC class II molecules have distinct distributions among cells that reflect the different effector functions of the T cells that recognize them. MHC class I molecules present peptides of cytosolic and nuclear origin e.g. from pathogens, commonly viruses, to CD8$^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. The CD8$^+$ T cells that recognize MHC class I:peptide complexes at the surface of infected cells are specialized to kill any cells displaying foreign peptides and so rid the body of cells infected with viruses and other cytosolic pathogens. The main function of CD4$^+$ T cells (CD4$^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

Epitope (also called "antigen determinant"): T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Vaccine: A vaccine is typically understood to be a prophylactic or therapeutic material providing at least one antigen or antigenic function. The antigen or antigenic function may stimulate the body's adaptive immune system to provide an adaptive immune response.

Antigen-providing mRNA: An antigen-providing mRNA in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

Bi-/multicistronic mRNA: mRNA, that typically may have two (bicistronic) or more (multicistronic) open reading frames (ORF). An open reading frame in this context is a sequence of several nucleotide triplets (codons) that can be translated into a peptide or protein. Translation of such a mRNA yields two (bicistronic) or more (multicistronic) distinct translation products (provided the ORFs are not identical). For expression in eukaryotes such mRNAs may for example comprise an internal ribosomal entry site (IRES) sequence.

5'-CAP-Structure: A 5'-CAP is typically a modified nucleotide, particularly a guanine nucleotide, added to the 5' end of an mRNA-molecule. Preferably, the 5'-CAP is added using a 5'-5'-triphosphate linkage (also named m7GpppN). Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety. These modified 5'-CAP structures may be used in the context of the present invention to modify the inventive mRNA sequence. Further modified 5'-CAP structures which may be used in the context of the present invention are CAP1 (methylation of the ribose of the adjacent nucleotide of m7GpppN), CAP2 (methylation of the ribose of the 2$^{nd}$ nucleotide downstream of the m7GpppN), CAP3 (methylation of the ribose of the 3$^{rd}$ nucleotide downstream of the m7GpppN), CAP4 (methylation of the ribose of the 4$^{th}$ nucleotide downstream of the m7GpppN), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Fragments of proteins: "Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide.

Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

Variants of proteins: "Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide.

Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Identity of a sequence: In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

Derivative of a protein or peptide: A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Monocistronic mRNA: A monocistronic mRNA may typically be an mRNA, that encodes only one open reading frame. An open reading frame in this context is a sequence of several nucleotide triplets (codons) that can be translated into a peptide or protein.

Nucleic acid: The term nucleic acid means any DNA- or RNA-molecule and is used synonymous with polynucleotide. Wherever herein reference is made to a nucleic acid or nucleic acid sequence encoding a particular protein and/or peptide, said nucleic acid or nucleic acid sequence, respectively, preferably also comprises regulatory sequences allowing in a suitable host, e.g. a human being, its expression, i.e. transcription and/or translation of the nucleic acid sequence encoding the particular protein or peptide.

Peptide: A peptide is a polymer of amino acid monomers. Usually the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

Pharmaceutically effective amount: A pharmaceutically effective amount in the context of the invention is typically understood to be an amount that is sufficient to induce an immune response.

Protein: A protein typically consists of one or more peptides and/or polypeptides folded into 3-dimensional form, facilitating a biological function.

Poly (C) sequence: A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

Poly-A-tail: A poly-A-tail also called "3'-poly(A) tail" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of a RNA.

Stabilized nucleic acid: A stabilized nucleic acid, typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'-CAP-Structure, a Poly-A-Tail, or any other UTR-modification. It can also be achieved by backbone-modification or modification of the G/C-content of the nucleic acid. Various other methods are known in the art and conceivable in the context of the invention.

Carrier/polymeric carrier: A carrier in the context of the invention may typically be a compound that facilitates transport and/or complexation of another compound. Said carrier may form a complex with said other compound. A polymeric carrier is a carrier that is formed of a polymer.

Cationic component: The term "cationic component" typically refers to a charged molecule, which is positively charged (cation) at a pH value of typically about 1 to 9, preferably of a pH value of or below 9 (e.g. 5 to 9), of or below 8 (e.g. 5 to 8), of or below 7 (e.g. 5 to 7), most preferably at physiological pH values, e.g. about 7.3 to 7.4. Accordingly, a cationic peptide, protein or polymer according to the present invention is positively charged under physiological conditions, particularly under physiological salt conditions of the cell in vivo. A cationic peptide or protein preferably contains a larger number of cationic amino acids, e.g. a larger number of Arg, His, Lys or Orn than other amino acid residues (in particular more cationic amino acids than anionic amino acid residues like Asp or Glu) or contains blocks predominantly formed by cationic amino acid residues. The definition "cationic" may also refer to "polycationic" components.

Vehicle: An agent, e.g. a carrier, that may typically be used within a pharmaceutical composition or vaccine for facilitating administering of the components of the pharmaceutical composition or vaccine to an individual.

3'-untranslated region (3'UTR): A 3'UTR is typically the part of an mRNA which is located between the protein coding region (i.e. the open reading frame) and the poly(A) sequence of the mRNA. A 3'UTR of the mRNA is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-Capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence which corresponds to such RNA sequence. In the context of the present invention, the term "a 3'UTR of a gene", such as "a 3'UTR of an albumin gene", is the sequence which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

5'-untranslated region (5'UTR): A 5'-UTR is typically understood to be a particular section of messenger RNA (mRNA). It is located 5' of the open reading frame of the mRNA. Typically, the 5'UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'UTR may be posttranscriptionally modified, for example by addition of a 5'-CAP. In the context of the present invention, a 5'UTR corresponds to the sequence of a mature mRNA which is located between the 5'-CAP and the start codon. Preferably, the 5'UTR corresponds to the sequence which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'UTR sequence may be an RNA sequence, such as in the mRNA sequence used for defining the 5'UTR sequence, or a DNA sequence which corresponds to such RNA sequence. In the context of the present invention, the term "a 5'UTR of a gene", such as "a 5'UTR of a TOP gene", is the sequence which corresponds to the 5'UTR of the mature mRNA derived from this gene, i.e. the mRNA obtained by transcription of the gene and maturation of the pre-mature mRNA. The term "5'UTR of a gene" encompasses the DNA sequence and the RNA sequence of the 5' UTR.

5' Terminal Oligopyrimidine Tract (TOP): The 5' terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5' end with a cytosine nucleotide. In TOP genes and TOP mRNAs, the TOP-motif preferably starts at its 5' end with the transcriptional start site and ends one nucleotide 5' to the first purin residue in said gene or mRNA. A TOP motif in the sense of the present invention is preferably located at the 5' end of a sequence which represents a 5'UTR or at the 5' end of a sequence which codes for a 5'UTR. Thus, preferably, a stretch of 3 or more pyrimidine nucleotides is called "TOP motif" in the sense of the present invention if this stretch is located at the 5' end of a respective sequence, such as the inventive mRNA, the 5'UTR element of the inventive mRNA, or the nucleic acid sequence which is derived from the 5'UTR of a TOP gene as described herein. In other words, a stretch of 3 or more pyrimidine nucleotides which is not located at the 5'-end of a 5'UTR or a 5'UTR element but anywhere within a 5'UTR or a 5'UTR element is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'-CAP to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363, SEQ ID NO. 1395, SEQ ID NO. 1421 and SEQ ID NO. 14221-1363 of the patent application PCT/EP2012/002448WO2013/143700 or homologs or variants thereof, whose disclosure is incorporated herewith by reference. In this context a particularly preferred fragment of a 5'UTR of a TOP gene is a 5'UTR of a TOP gene lacking the 5'TOP motif. The term '5'UTR of a TOP gene' preferably refers to the 5'UTR of a naturally occurring TOP gene.

Fragment of a nucleic acid sequence, particularly an mRNA: A fragment of a nucleic acid sequence consists of a continuous stretch of nucleotides corresponding to a continuous stretch of nucleotides in the full-length nucleic acid sequence which is the basis for the nucleic acid sequence of the fragment, which represents at least 20%, preferably at least 30%, more preferably at least 40%, more preferably at least 50%, even more preferably at least 60%, even more preferably at least 70%, even more preferably at least 80%, and most preferably at least 90% of the full-length nucleic acid sequence. Such a fragment, in the sense of the present invention, is preferably a functional fragment of the full-length nucleic acid sequence.

Variant of a nucleic acid sequence, particularly an mRNA: A variant of a nucleic acid sequence refers to a variant of nucleic acid sequences which forms the basis of a nucleic acid sequence. For example, a variant nucleic acid sequence may exhibit one or more nucleotide deletions, insertions, additions and/or substitutions compared to the nucleic acid sequence from which the variant is derived. Preferably, a variant of a nucleic acid sequence is at least 40%, preferably at least 50%, more preferably at least 60%, more preferably at least 70%, even more preferably at least 80%, even more preferably at least 90%, most preferably at least 95% identical to the nucleic acid sequence the variant is derived from. Preferably, the variant is a functional variant. A "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence.

Homolog of a nucleic acid sequence: The term "homolog" of a nucleic acid sequence refers to sequences of other species than the particular sequence. It is particular preferred that the nucleic acid sequence is of human origin and therefore it is preferred that the homolog is a homolog of a human nucleic acid sequence.

Jet injection: The term “jet injection”, as used herein, refers to a needle-free injection method, wherein a fluid containing at least one inventive mRNA sequence and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the mRNA sequence according to the invention. In a preferred embodiment, jet injection is used for intramuscular injection of the inventive mRNA. In a further preferred embodiment, jet injection is used for intradermal injection of the inventive mRNa.

The present invention is based on the surprising finding of the present inventors that an mRNA sequence comprising a coding region, encoding at least one antigenic peptide or protein of Respiratory syncytial virus (RSV) induces antigen-specific immune responses and therefore prevent or at least minimize Respiratory syncytial virus (RSV) infections. It was very surprising for the inventors that the inventive mRNA sequence induces at least the same immune responses than vaccines based on inactivated RSV which consists of the whole virus. Even more surprisingly the inventive mRNA sequence coding for an antigenic protein of RSV induced antigen-specific CD8+-T cells in contrast to a vaccine based on an inactivated RSV. Additionally, in a cotton rat RSV challenge model, the virus titers in the nose and in the lung of mRNA vaccinated animals were much lower compared to animals vaccinated with vaccines based on an inactivated RSV virus. With regard to safety the inventors could show that the mRNA-based RSV vaccine showed no hints for vaccine-mediated disease enhancement, in terms of lung pathology, compared to a vaccine based on formalin-inactivated virus. Furthermore, it has surprisingly been found by the inventors that already one single vaccination with the inventive mRNA sequence was sufficient for eliciting an immune response against the administered antigen(s). Specifically, it has been found that one single administration, preferably by intradermal or intramuscular injection, of the inventive mRNA is highly efficient in reducing viral titers in the lung after challenge with RSV virus.

In summary, the inventive mRNA sequence comprising a coding region encoding at least one antigenic peptide or protein of Respiratory syncytial virus (RSV) could provide an effective and safe vaccine, particularly for infants, the elderly and immunocompromised patients.

In this context it is particularly preferred that the inventive mRNA sequence comprises a coding region, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof.

The coding region of the inventive mRNA sequence according to the first aspect of the present invention may occur as a mono-, bi-, or even multicistronic mRNA, i.e. an mRNA sequence which carries the coding sequences of one, two or more proteins or peptides. Such coding sequences in bi-, or even multicistronic mRNAs may be separated by at least one internal ribosome entry site (IRES) sequence, e.g. as described herein or by signal peptides which induce the cleavage of the resulting polypeptide which comprises several proteins or peptides.

According to the first aspect of the present invention, the inventive mRNA sequence comprises a coding region, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof. In a particularly preferred embodiment of the first aspect of the invention, the inventive mRNA sequence comprises a coding region, encoding at least one antigenic peptide or protein derived from the fusion protein F, the nucleoprotein N, or the M2-1 protein of Respiratory syncytial virus (RSV) or a fragment, variant or derivative thereof.

In this context, the amino acid sequence of the at least one antigenic peptide or protein may be selected from any peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of any RSV isolate or from any synthetically engineered RSV peptide or protein or from a fragment, variant or derivative thereof.

In a particularly preferred embodiment, the full-length protein of the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) is encoded by the coding region comprised in the inventive mRNA.

In this context, the full-length protein from the fusion protein F and the nucleoprotein N are particularly preferred. Furthermore a mutant of the F protein with a deletion of the cytoplasmic tail is particularly preferred. An example of such a deletion mutant is the RSV-Fdel 554-574 long protein according to (Oomens et al. 2006. J. Virol. 80(21):10465-77).

In a further particularly preferred embodiment, a fragment comprising at least one epitope of the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) is encoded by the coding region comprised in the inventive mRNA.

Particularly preferred are the amino acid sequences of the RSV strain long (ATCC VR-26) according to the NCBI accession No. AY911262:

Fusion Protein F of the RSV Strain ATCC VR-26 Long:

```
Amino acid sequence according to SEQ ID No. 1:
MELPILKANA ITTILAAVTF CFASSQNITE EFYQSTCSAV

SKGYLSALRT GWYTSVITIE LSNIKENKCN GTDAKVKLIN

QELDKYKNAV TELQLLMQST TAANNRARRE LPRFMNYTLN

NTKKTNVTLS KKRKRRFLGF LLGVGSAIAS GIAVSKVLHL
```

-continued

```
EGEVNKIKSA LLSTNKAVVS LSNGVSVLTS KVLDLKNYID

KQLLPIVNKQ SCRISNIETV IEFQQKNNRL LEITREFSVN

AGVTTPVSTY MLTNSELLSL INDMPITNDQ KKLMSNNVQI

VRQQSYSIMS IIKEEVLAYV VQLPLYGVID TPCWKLHTSP

LCTTNTKEGS NICLTRTDRG WYCDNAGSVS FFPQAETCKV

QSNRVFCDTM NSLTLPSEVN LCNVDIFNPK YDCKIMTSKT

DVSSSVITSL GAIVSCYGKT KCTASNKNRG IIKTFSNGCD

YVSNKGVDTV SVGNTLYYVN KQEGKSLYVK GEPIINFYDP

LVFPSDEFDA SISQVNEKIN QSLAFIRKSD ELLHHVNAGK

STTNIMITTI IIVIIVILLS LIAVGLLLYC KARSTPVTLS

KDQLSGINNI AFSN
```

Glycoprotein G of the RSV Strain ATCC VR-26 Long:

```
Amino acid sequence according to SEQ ID No. 2:
MSKNKDQRTA KTLEKTWDTL NHLLFISSGL YKLNLKSIAQ

ITLSILAMII STSLIITAII FIASANHKVT LTTAIIQDAT

SQIKNTTPTY LTQDPQLGIS FSNLSEITSQ TTTILASTTP

GVKSNLQPTT VKTKNTTTTQ TQPSKPTTKQ RQNKPPNKPN

NDFHFEVFNF VPCSICSNNP TCWAICKRIP NKKPGKKTTT

KPTKKPTFKT TKKDLKPQTT KPKEVPTTKP TEEPTINTTK

TNITTTLLTN NTTGNPKLTS QMETFHSTSS EGNLSPSQVS

TTSEHPSQPS SPPNTTRQ
```

Short Hydrophobic Protein SH of the RSV Strain ATCC VR-26 Long:

```
Amino acid sequence according to SEQ ID No. 3:
MENTSITIEF SSKFWPYFTL IHMITTIISL LIIISIMTAI

LNKLCEYNVF HNKTFELPRA RVNT
```

Matrix Protein M of the RSV Strain ATCC VR-26 Long:

```
Amino acid sequence according to SEQ ID No. 4:
METYVNKLHE GSTYTAAVQY NVLEKDDDPA SLTIWVPMFQ

SSMPADLLIK ELANVNILVK QISTPKGPSL RVMINSRSAL

LAQMPSKFTI CANVSLDERS KLAYDVTTPC EIKACSLTCL

KSKNMLTTVK DLTMKTLNPT HDIIALCEFE NIVTSKKVII

PTYLRSISVR NKDLNTLENI TTTEFKNAIT NAKIIPYSGL

LLVITVTDNK GAFKYIKPQS QFIVDLGAYL EKESIYYVTT

NWKHTATRFA IKPMED
```

Nucleoprotein N of the RSV Strain ATCC VR-26 Long:

```
Amino acid sequence according to SEQ ID No. 5:
MALSKVKLND TLNKDQLLSS SKYTIQRSTG DSIDTPNYDV

QKHINKLCGM LLITEDANHK FTGLIGMLYA MSRLGREDTI

KILRDAGYHV KANGVDVTTH RQDINGKEMK FEVLTLASLT

TEIQINIEIE SRKSYKKMLK EMGEVAPEYR HDSPDCGMII

LCIAALVITK LAAGDRSGLT AVIRRANNVL KNEMKRYKGL

LPKDIANSFY EVFEKHPHFI DVFVHFGIAQ SSTRGGSRVE

GIFAGLFMNA YGAGQVMLRW GVLAKSVKNI MLGHASVQAE

MEQVVEVYEY AQKLGGEAGF YHILNNPKAS LLSLTQFPHF

SSVVLGNAAG LGIMGEYRGT PRNQDLYDAA KAYAEQLKEN

GVINYSVLDL TAEELEAIKH QLNPKDNDVE L
```

Large Polymerase L of the RSV Strain ATCC VR-26 Long:

```
Amino acid sequence according to SEQ ID No. 6:
MDPIINGNSA NVYLTDSYLK GVISFSECNA LGSYIFNGPY

LKNDYTNLIS RQNPLIEHMN LKKLNITQSL ISKYHKGEIK

LEEPTYFQSL LMTYKSMTSL EQIATTNLLK KIIRRAIEIS

DVKVYAILNK LGLKEKDKIK SNNGQDEDNS VITTIIKDDI

LSAVKDNQSH LKADKNHSTK QKDTIKTTLL KKLMCSMQHP

PSWLIHWFNL YTKLNNILTQ YRSNEVKNHG FILIDNQTLS

GFQFILNQYG CIVYHKELKR ITVTTYNQFL TWKDISLSRL

NVCLITWISN CLNTLNKSLG LRCGFNNVIL TQLFLYGDCI

LKLFHNEGFY IIKEVEGFIM SLILNITEED QFRKRFYNSM

LNNITDAANK AQKNLLSRVC HTLLDKTVSD NIINGRWIIL

LSKFLKLIKL AGDNNLNNLS ELYFLFRIFG HPMVDERQAM

DAVKVNCNET KFYLLSSLSM LRGAFIYRII KGFVNNYNRW

PTLRNAIVLP LRWLTYYKLN TYPSLLELTE RDLIVLSGLR

FYREFRLPKK VDLEMIINDK AISPPKNLIW TSFPRNYMPS

HIQNYIEHEK LKFSESDKSR RVLEYYLRDN KFNECDLYNC

VVNQSYLNNP NHVVSLTGKE RELSVGRMFA MQPGMFRQVQ

ILAEKMIAEN ILQFFPESLT RYGDLELQKI LELKAGISNK

SNRYNDNYNN YISKCSIITD LSKFNQAFRY ETSCICSDVL

DELHGVQSLF SWLHLTIPHV TIICTYRHAP PYIRDHIVDL

NNVDEQSGLY RYHMGGIEGW CQKLWTIEAI SLLDLISLKG

KFSITALING DNQSIDISKP VRLMEGQTHA QADYLLALNS

LKLLYKEYAG IGHKLKGTET YISRDMQFMS KTIQHNGVYY

PASIKKVLRV GPWINTILDD FKVSLESIGS LTQELEYRGE

SLLCSLIFRN VWLYNQIALQ LKNHALCNNK LYLDILKVLK

HLKTFFNLDN IDTALTLYMN LPMLFGGGDP NLLYRSFYRR

TPDFLTEAIV HSVFILSYYT NHDLKDKLQD LSDDRLNKFL

TCIITFDKNP NAEFVTLMRD PQALGSERQA KITSEINRLA

VTEVLSTAPN KIFSKSAQHY TTTEIDLNDI MQNIEPTYPH

GLRVVYESLP FYKAEKIVNL ISGTKSITNI LEKTSAIDLT

DIDRATEMMR KNITLLIRIL PLDCNRDKRE ILSMENLSIT

ELSKYVRERS WSLSNIVGVT SPSIMYTMDI KYTTSTIASG
```

-continued

IIIEKYNVNS LTRGERGPTK PWVGSSTQEK KTMPVYNRQV

LTKKQRDQID LLAKLDWVYA SIDNKDEFME ELSIGTLGLT

YEKAKKLFPQ YLSVNYLHRL TVSSRPCEFP ASIPAYRTTN

YHFDTSPINR ILTEKYGDED IDIVFQNCIS FGLSLMSVVE

QFTNVCPNRI ILIPKLNEIH LMKPPIFTGD VDIHKLKQVI

QKQHMFLPDK ISLTQYVELF LSNKTLKSGS HVNSNLILAH

KISDYFHNTY ILSTNLAGHW ILIIQLMKDS KGIFEKDWGE

GYITDHMFIN LKVFFNAYKT YLLCFHKGYG KAKLECDMNT

SDLLCVLELI DSSYWKSMSK VFLEQKVIKY ILSQDASLHR

VKGCHSFKLW FLKRLNVAEF TVCPWVVNID YHPTHMKAIL

TYIDLVRMGL INIDRIHIKN KHKFNDEFYT SNLFYINYNF

SDNTHLLTKH IRIANSELEN NYNKLYHPTP ETLENILANP

IKSNDKKTLN DYCIGKNVDS IMLPLLSNKK LVKSSAMIRT

NYSKQDLYNL FPTVVIDRII DHSGNTAKSN QLYTTTSHQI

SLVHNSTSLY CMLPWHHINR FNFVFSSTGC KISIEYILKD

LKIKDPNCIA FIGEGAGNLL LRTVVELHPD IRYIYRSLKD

CNDHSLPIEF LRLYNGHINI DYGENLTIPA TDATNNIHWS

YLHIKFAEPI SLFVCDAELP VTVNWSKIII EWSKHVRKCK

YCSSVNKCTL IVKYHAQDDI DFKLDNITIL KTYVCLGSKL

KGSEVYLVLT IGPANIFPVF NVVQNAKLIL SRTKNFIMPK

KADKESIDAN IKSLIPFLCY PITKKGINTA LSKLKSVVSG

DILSYSIAGR NEVFSNKLIN HKHMNILKWF NHVLNFRSTE

LNYNHLYMVE STYPYLSELL NSLTTNELKK LIKITGSLLY

NFHNE

M2-1 Protein of the RSV Strain ATCC VR-26 Long:

Amino acid sequence according to SEQ ID No. 7:
MSRRNPCKFE IRGHCLNGKR CHFSHNYFEW PPHALLVRQN

FMLNRILKSM DKSIDTLSEI SGAAELDRTE EYALGVVGVL

ESYIGSINNI TKQSACVAMS KLLTELNSDD IKKLRDNEEL

NSPKIRVYNT VISYIESNRK NNKQTIHLLK RLPADVLKKT

IKNTLDIHKS ITINNPKELT VSDTNDHAKN NDTT

M2-2 Protein of the RSV Strain ATCC VR-26 Long:

Amino acid sequence according to SEQ ID No. 8:
MTMPKIMILP DKYPCSITSI LITSRCRVTM YNRKNTLYFN

QNNPNNHMYS PNQTFNEIHW TSQDLIDTIQ NFLQHLGVIE

DIYTIYILVS

Phosphoprotein P of the RSV Strain ATCC VR-26 Long:

Amino acid sequence according to SEQ ID No. 9:
MEKFAPEFHG EDANNRATKF LESIKGKFTS PKDPKKKDSI

ISVNSIDIEV TKESPITSNS TIINPTNETD DNAGNKPNYQ

RKPLVSFKED PIPSDNPFSK LYKETIETFD NNEEESSYSY

EEINDQTNDN ITARLDRIDE KLSEILGMLH TLVVASAGPT

SARDGIRDAM VGLREEMIEK IRTEALMTND RLEAMARLRN

EESEKMAKDT SDEVSLNPTS EKLNNLLEGN DSDNDLSLED

F

Non-Structural Protein NS1 of the RSV Strain ATCC VR-26 Long:

Amino acid sequence according to SEQ ID No. 10:
MGSNSLSMIK VRLQNLFDND EVALLKITCY TDKLIHLTNA

LAKAVIHTIK LNGIVFVHVI TSSDICPNNN IVVKSNFTTM

PVLQNGGYIW EMMELTHCSQ PNGLIDDNCE IKFSKKLSDS

TMTNYMNQLS ELLGFDLNP

Non-Structural Protein NS2 of the RSV Strain ATCC VR-26 Long:

Amino acid sequence according to SEQ ID No. 11:
MDTTHNDTTP QRLMITDMRP LSLETTITSL TRDIITHRFI

YLINHECIVR KLDERQATFT FLVNYEMKLL HKVGSTKYKK

YTEYNTKYGT FPMPIFINHD GFLECIGIKP TKHTPIIYKY

DLNP

In the context of the invention, additionally to the here disclosed amino acid sequences according to SEQ ID Nos. 1-11, also amino acid sequences of different Respiratory syncytial virus (RSV) isolates can be used according to the invention and are incorporated herewith. These Respiratory syncytial virus (RSV) isolates show preferably an identity of at least 70%, more preferably of at least 80% and most preferably of at least 90% with the amino acid sequences according to SEQ ID Nos. 1-11.

Furthermore, in this context the coding region encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof, may be selected from any nucleic acid sequence comprising a coding region derived from any Respiratory syncytial virus (RSV) isolate or a fragment or variant thereof.

Particularly preferred are the wild type mRNA sequences of the coding regions of the RSV strain long (ATCC VR-26) according to the NCBI accession No. AY911262:

mRNA Coding for the Fusion Protein F of the RSV Strain ATCC VR-26 Long:

mRNA sequence according to SEQ ID No. 12:
auggaguugccaauccucaaagcaaaugcaauuaccacaauccucgcugc
agucacauuuugcuuugcuucuagucaaaacaucacugaagaauuuuauc
aaucaacaugcagugcaguuagcaaaggcuaucuuagugcucuaagaacu
gguugguauacuaguguuauaacuauagaauuaaguaauaucaaggaaaa
uaaguguaauggaacagaugcuaagguaaaauugauaaaccaagaauuag
auaaauauaaaaaugcuguaacagaauugcaguugcucaugcaaagcaca
acagcagcaaacaaucgagccagaagagaacuaccaagguuuaugaauua
uacacucaacaauaccaaaaaaaccaauguaacauuaagcaagaaaagga
aaagaagauuucuugguuuuuuguuagguguuggaucugcaaucgccagu
ggcauugcuguaucuaagguccugcacuuagaaggagaagugaacaagau
caaaagugcucuacuauccacaaacaaggccguagucagcuuaucaaaug
gaguuagugucuuaaccagcaaaguguuagaccucaaaaacuauauagau
aaacaauuguuaccuauugugaauaagcaaagcugcagaauaucaaauau
agaaacugugauagaguuccaacaaaagaacaacagacuacuagagauua
ccagggaauuuaguguuaaugcagguguaacuacaccuguaagcacuuac
auguuaacuaauagugaauuauugucauuaaucaaugauaugccuauaac
aaaugaucagaaaaaguuaauguccaacaauguucaaauaguuagacagc
aaaguuacucuaucauguccauaauaaaagaggaagucuuagcauaugua
guacaauuaccacuauaugguguggauagauacaccuuguuggaaauuaca
cacauccccucuauguacaaccaacacaaaagaagggucaaacaucuguu
uaacaagaacugacagaggaugguacugugacaaugcaggaucaguaucu
uucuucccacaagcugaaacauguaaaguucaaucgaaucgaguauuuug
ugacacaaugaacaguuuaacauuaccaagugaaguaaaucucugcaaug
uugacauauucaaucccaaauaugauuguaaaauuaugacuucaaaaaca
gauguaagcagcuccguuaucacaucucuaggagccauuguguucaugcua
uggcaaaacuaaauguacagcauccaauaaaaaucguggaaucauaaaga
cauuuucuaacggguguugauuauguaucaaauaaaggggguggacacugug
ucuguagguaacacauuauauuauguaaauaagcaagaaggcaaaagucu
cuauguaaaaggugaaccaauaauaaauuucuaugacccauuaguauucc
ccucugaugaauuugaugcaucaauaucucaagucaaugagaagauuaac
cagaguuuagcauuuauucguaaauccgaugaauuauuacaucauguaaa
ugcugguaaaucaaccacaaauaucaugauaacuacuauaauuauaguga
uuauaguaauauuguuaucauuaauugcuguuggacugcuccuauacugu
aaggccagaagcacaccagucacacuaagcaaggaucaacugagugguau
aaauaauauugcauuuaguaacuga mRNA Coding for the Glycoprotein G of the RSV Strain ATCC VR-26 Long:

mRNA sequence according to SEQ ID No. 13:
auguccaaaaacaaggaccaacgcaccgcuaagacacuagaaaagaccug
ggacacucucaaucauuuauuauucauaucaucgggcuuauauaaguuaa -continued aucuuaaaucuauagcacaaaucacauuauccauucuggcaaugauaaauc
ucaacuucacuuauaauuacagccaucauauucauagccucggcaaacca
caaagucacacuaacaacugcaaucauacaagaugcaacaagccagauca
agaacacaaccccaacauaccucacucaggauccucagcuuggaaucagc
uucuccaaucugucugaaauuacaucacaaaccaccaccauacuagcuuc
aacaacaccaggagucaagucaaaccugcaacccacaacagucaagacua
aaaacacaacaacaacccaaacacaacccagcaagcccacuacaaaacaa
cgccaaaacaaaccaccaaacaaacccaauaaugauuuucacuucgaagu
guuuaacuuuguacccugcagcauaugcagcaacaauccaaccugcuggg
cuaucugcaaaagaauaccaaacaaaaaaccaggaaagaaaaccaccacc
aagccuacaaaaaaaccaaccuucaagacaaccaaaaaagaucucaaacc
ucaaaccacuaaaccaaaggaaguacccaccaccaagcccacagaagagc
caaccaucaacaccaccaaaacaaacaucacaacuacacugcucaccaac
aacaccacaggaaauccaaaacucacaagucaaauggaaaccuuccacuc
aaccuccuccgaaggcaaucuaagcccuucucaagucuccacaacauccg
agcacccaucacaacccucaucuccacccaacacaacacgccaguag mRNA Coding for the Short Hydrophobic Protein SH of the RSV Strain ATCC VR-26 Long:

mRNA sequence according to SEQ ID No. 14:
auggaaaauacauccauaacaauagaauucucaagcaaauucuggccuua
cuuuacacuaauacacaugaucacaacaauaaucucuuugcuaaucauaa
ucuccaucaugacugcaauacuaaacaaacuuugugaauauaacguauuc
cauaacaaaaccuuugaguuaccaagagcucgagucaacacauag mRNA Coding for the Matrixprotein M of the RSV Strain ATCC VR-26 Long:

mRNA sequence according to SEQ ID No. 15:
auggaaacauacgugaacaagcuucacgaaggcuccacauacacagcugc
uguucaauacaauguccuagaaaaagacgaugacccugcaucacuuacaa
uaugggugcccauguuccaaucaucuaugccagcagauuuacuuauaaaa
gaacuagcuaaugucaacauacuagugaaacaaauauccacacccaaggg
accuucacuaagagucaugauaaacucaagaagugcauugcuagcacaaa
ugcccagcaaauuuaccauaugugcuaaugugucccuuggaugaaagaagc
aaacuggcauaugaugaaccacacccugugaaaucaaggcauguagucu
aacaugccuaaaaucaaaaaaauauguuaacuacaguuaaagaucucacua
ugaagacacucaaccccacacaugauauuauugcuuuaugugaauuugaa
aacauaguaacaucaaaaaaagucauaauaccaacauaccuaagauccau
cagugucagaaauaaagaucugaacacacuugaaaauauaacaaccacug
aauucaaaaaugccaucacaaaugcaaaaaucaucccuuacucaggauua
cuauuagucaucacagugacugacaacaaaggagcauucaaauacauaaa
gccgcaaagucaauucauaguagaucuuggagcuuaccuagaaaaagaaa -continued guauauauuauguuaccacaaauuggaagcacacagcuacacgauuugca aucaaacccauggaagauuaa mRNA Coding for the Nucleoprotein N of the RSV Strain ATCC VR-26 Long:

mRNA sequence according to SEQ ID No. 16:
auggcucuuagcaaagucaaguugaaugauacacucaacaaagaucaacu ucugucaucuagcaaauacaccauccaacggagcacaggagauaguauug auacuccuaauuaugaugugcagaaacacaucaauaaguuauguggcaug uuauuaaucacagaagaugcuaaucauaaauucacugguuaauagguau guuauaugcuaugucuagguuaggaagagaagacaccauaaaaauacuca gagaugcgggauaucauguaaaagcaaauggaguagauguaacaacacau cgucaagacaucaaugggaaagaaaugaaauuugaaguguuaacauuggc aagcuuaacaacugaaauucaaaucaacauugagauagaaucuagaaaau ccuacaaaaaaaugcuaaaagaaaugggagagguagcuccagaauacagg caugauucuccugauugugggaugauaauauuauguauagcagcauuagu -continued aauaaccaaauuggcagcaggggauagaucuggucuuacagccgugauua ggagagcuaauaauguccuaaaaaaugaaaugaaacguuacaaaggcuua cuacccaaggauauagccaacagcuucuaugaaguguuugaaaaacaucc ccacuuuauagauguuuuuguucauuuugguauagcacaaucuuccacca gagguggcaguagaguugaagggauuuuugcaggauuguuuaugaaugcc uauggugcagggcaaguaaugcuacggugggagucuuagcaaaaucagu uaaaaauauuauguuaggacaugcuagugugcaagcagaaauggaacaag uuguugagguuuaugaauaugcccaaaaauuggguggagaagcaggauuc uaccauauauugaacaacccaaaagcaucauuauuaucuuugacucaauu uccucacuuuuccaguguaguauuaggcaaugcugcuggccuaggcauaa ugggagaguacagagguacaccgaggaaucaagaucuauaugaugcagca aaggcauaugcugaacaacucaaagaaaauggugugauuaacuacagugu auuagacuugacagcagaagaacuagaggcuaucaaacaucagcuuaauc caaaagauaaugauguagagcuuuga mRNA Coding for the Large Polymerase L of the RSV Strain ATCC VR-26 Long:

mRNA sequence according to SEQ ID No. 17:
auggaucccauuauuaauggaaauucugcuaauguuuaucuaaccgauaguuauuuaaaagguguuaucucuuucucagagu guaaugcuuuaggaaguuacauauucaaugguccuuaucucaaaaaugauuauaccaacuuaauuaguagacaaaauccauua auagaacacaugaaucuaaagaaacuaaauauaacacaguccuuaauaucuaaguaucauaaaggugaaauaaaauuagaaga gccuacuuauuuucagucauuacuuaugacauacaagaguaugaccucguuggaacagauugcuaccacuaauuuacuuaaa aagauaauaagaagagcuauagaaauaagugaugucaaagucuaugcuauauugaauaaacuagggcuuaaagaaaaggacaa gauuaaauccaacaauggacaggaugaagacaacucaguuauuacgaccauaaucaaagaugauauacuuucagcuguuaagg auaaucaaucucaucuuaaagcagacaaaaaucacucuacaaaacaaaaagacacaaucaaaacaacacucuugaagaaauuaau guguucaaugcagcauccuccaucaugguuaauacauugguuuaauuuauacacaaaauuaaacaacauauuaacacaguauc gaucaaaugagguuaaaaaccauggguuuauauugauagauaaucaaacucuuaguggauuucaauuuauuuugaaucaaua ugguuguauaguuuaucauaaggaacucaaaagaauuacugugacaaccuauaaucaauucuugacauggaaagauauuagc cuuaguagauuaaauguuuguuuaauuacauggauuaguaacugcuugaacacauuaaauaaaagcuuaggcuuaagaugcg gauucaauaauguuaucuugacacaacuauuccuuuauggugauuguauacuaaagcuauuucacaaugagggguucuacau aauaaaagagguagagggauuuauuaugucucuaauuuuaaauauaacagaagaagaucaauucagaaaacgauuuuauaau aguaugcucaacaacaucacagaugcugcuaauaaagcucagaaaaucugcuaucaagaguaugucauacauuauuagauaa gacaguauccgauaauauaauaaauggcagauggauaauucuauuaaguaaguuccuuaaauuaauuaagcuugcaggugac aauaaccuuaacaaucugagugaacuauauuuuuuguucagaauauuggacacccaagguagaugaaagacaagccaugg augcuguuaaaguuaauugcaaugagaccaaauuuuacuuguuaagcaguuugaguauguuaagaggugccuuuauauaua gaauuauaaaaggguuuguaaauaauuacaacagauggccuacuuuaagaaaugcuauuguuuuacccuuaagaugguuaac uuacuauaaacuaaacacuuauccuucuuuguuggaacuuacagaaagagauuugauuguguuaucaggacuacguuucuau cgugaguuucgguugccuaaaaaaguggaucuugaaaugauuauaaaugauaaagcuauaucacccccuaaaaauuugauau ggacuaguuucccuagaaauuauaugccgucacacauacaaaacuauauagaacaugaaaaauuaaaauuuuccgagagugau aaaucaagaagaguauuagaguauuauuuaagagauaacaaauucaaugaaugugauuuauacaacuguguaguuaaucaaa guuaucucaacaacccuaaucaugugguaucauugacaggcaaagaaagagaacucaguguagguagaauguuugcaaugca -continued accgggaauguucagacagguucaaauauuggcagagaaaaugauagcugaaaacauuuuacaauucuuuccugaaagucuu acaagauaugggugaucuagaacuacaaaaaauauuagaauugaaagcaggaauaaguaacaaaucaaaucgcuacaaugauaa uuacaacaauuacauuaguaagugcucuaucaucacagaucucagcaaauucaaucaagcauuucgauaugaaacgucaugua uuuguagugaugugcuggaugaacugcaugguguacaaucucuauuuuccugguuacauuuaacuauuccucaugucacaa uaauaugcacauauaggcaugcacccccuauauaagagaucauauuguagaucuuaacaauguagaugaacaaaguggauua uauagauaucacaugggugguauugaagggugggugucaaaaacuauggaccauagaagcuauaucacuauuggaucuaaauau cucucaaagggaaauucucaauuacugcuuuaauuaauggugacaaucaaucaauagauauaagcaaaccagucagacucaug gaaggucaaacucaugcucaagcagauuauuugcuagcauuaaauagccuuaaauuacuguauaaagaguaugcaggcauag gucacaaauuaaaaggaacugagacuuauauaucacgagauaugcaauuuaugaguaaaacaauucaacauaacgguguauau uacccugcuaguauaaagaaaguccuaagagugggaccguggauaaacacuauacuugaugauuucaaagugagucuagaau cuauagguaguuugacacaagaauuagaauauagaggugaaagucuauuaugcaguuuaauauuuagaaauguaugguuaua uaaucaaauugcucuacaauuaaaaaaucaugcguuauguaacaauaaauuauauuuggacauauuaaagguucugaaacacu uaaaaaccuuuuuuaaucuugauaauauugauacagcauuaacauuguauaugaauuuacccauguuauuuggugguggug aucccaacuuguuauaucgaaguuucuauagaagaacuccugauuuccucacagaggcuauaguucacucuguguucauacu uaguuauuauacaaaccaugacuuaaaagauaaacuucaagauuugucagaugauagauugaauaaguucuuaacaugcauaa ucacguuugacaaaaacccuaaugcugaauucguaacauugaugagagaucccucaagcuuuagggucugagagacaagcuaaa auuacuagugaaaucaauagacuggcaguuacagagguuuugaguacagcuccaaacaaaauauucuccaaaagugcacaaca uuauaccacuacagagauagaucuaaaugauauuaugcaaaauauagaaccuacauauccucacgggcuaagaguuguuuaug aaaguuuacccuuuuauaaagcagagaaaauaguaaaucuuauaucagguacaaaaucuauaacuaacauacuggaaaagacu ucugccauagacuuaacagauauugauagagccacugagaugaugaggaaaaacauaacuuugcuuauaaggauacuuccau uggauuguaacagagauaaaagagaaauauugaguauggaaaaccuaaguauuacugaauuaagcaaauauguuagggaaag aucuuggucuuuauccaauauaguugguguuacaucacccaguaucauguauacaauggacaucaaauauacaacaagcacua uagcuaguggcauaauuauagagaaauauaauguuaacaguuuaacacguggugagagaggaccaacuaaaccaugguugg uucaucuacacaagagaaaaaaacaaugccaguuuauaauagacaaguuuuaaccaaaaaacaaagagaucaaauagaucuauu agcaaaauuggauuggguguaugcaucuauagauaacaaggaugaauucauggaagaacucagcauaggaacccuuggguua acauaugaaaaggccaaaaaauuauuuccacaauauuuaagugucaacuauuugcaucgccuuacagucaguaguagaccaug ugaauucccugcaucaauaccagcuuauagaacaacaaauuaucacuuugacacuagcccuauuaaucgcauauuaacagaaa aguauggugaugaagauauugacauaguauuccaaaacuguauaagcuuuggccuuagcuuaaugucaguaguagaacaauu uacuaauguauguccuaacagaauuauucucauaccuaagcuuaaugagauacauuugaugaaaccucccauauucacaggug auguugauauucacaaguuaaaacaagugauacaaaaacagcauauguuuuuaccagacaaaauaaguuugacucaauaugug gaauuauucuuaaguaacaaaacacucaaaucuggaucucauguuaauucuaauuuaauauuggcacauaaaauaucugacua uuuucauaauacuuacauuuuaaguacuaauuuagcuggacauuggauucuaauuauacaacuuaugaaagauucuaaaggu auuuuugaaaaagauuggggagagggauauauaacugaucauauguuuauuaauuugaaaguuuucuucaaugcuuauaag accuaucucuuguguuuucauaaagguuauggcaaagcaaaacuggagugugauaugaacacuucagaucuucuauguguau uggaauuaauagacaguaguuauuggaagucuaugucuaagguauuuuuagaacaaaaaguuaucaaauacauucuuagcca agaugcaaguuuacauagaguaaaaggaugucauagcuucaaauuaugguuucuuaaacgucuuaauguagcagaauuuaca guuugcccuuggguuguuaacauagauuaucauccaacacauaugaaagcaauauuaacuuauauagaucuuguuagaaugg gauugauaaauauagauagaauacacauuaaaaauaaacacaaauucaaugaugaauuuuauacuucuaaucucuuuuacauu aauuauaacuucucagauaauacucaucuauuaacuaaacauauaaggauugcuaauucagaauuagaaaauaauuacaacaa auuauaucauccuacaccagaaacccuagagaauauacuagccaauccgauuaaaaguaaugacaaaaagacacugaacgacua -continued uuguauagguaaaaauguugacucaauaauguuaccauuguuaucuaauaagaagcuuguuaaaucgucugcaaugauuaga accaauuacagcaaacaagaccuguacaaucuauucccuacgguugugaucgauagaauuauagaucauucagguaauacagc caaauccaaccaacuuuacacuacuacuucccaucaaauaucuuuagugcacaauagcacaucacuuuauugcaugcuuccuu ggcaucauauuaauagauucaauuuuguauuuaguucuacagguuguaaaauuaguauagaguauauuuuaaaagaccuuaa aauuaaagauccuaauuguauagcauucauaggugaaggagcagggaauuuauuauugcguacagugguggaacuucauccu gacauaagauauauuuacagaagucugaaagauugcaaugaucauaguuuaccuauugaguuuuuaaggcuauacaauggac auaucaacauugauuauggugaaaauuugaccauuccugcuacagaugcaaccaacaacauucauuggucuuauuuacauaua aaguuugcugaaccuaucagucuuuuuguaugugaugccgaauugccuguaacagucaacuggaguaaaauuauaauagaau ggagcaagcauguaagaaaaugcaaguacuguuccucaguuaauaaauguacguuaauaguaaaauaucaugcucaagauga uauugauuucaaauuagacaauauaacuauauuaaaaacuuauguaugcuuaggcaguaaguuaaagggaucggagguuuac uuaguccuuacaauagguccugcaaauauauuuccaguauuuaauguaguacaaaaugcuaaauugauacuaucaagaaccaa aaauuucaucaugccuaagaaagcugauaaagagucuauugaugcaaauauuaaaaguuugauacccuuucuuuguuacccu auaacaaaaaaaggaauuaauacugcauugucaaaacuaaagaguguuguuaguggagauauacuaucauauucuauagcug gacggaaugaaguuuucagcaauaaacuuauaaaucauaagcauaugaacaucuuaaagugguucaaucauguuuuaaauuu cagaucaacagaacuaaacuauaaccauuuauauaugguagaaucuacauauccuuaccuaagugaauuguuaaacagcuuga caacuaaugaacuuaaaaaacugauuaaaaucacagguagucuguuauacaacuuucauaaugaauaa mRNA Coding for the Protein M2-1 of the RSV Strain ATCC VR-26 Long:

mRNA sequence according to SEQ ID No. 18:
Augucacgaaggaauccuugcaaauuugaaauucgaggucauugcuugaa ugguaagagaugucauuuuagucauaauuauuuugaauggccaccccaug cacugcucguaagacaaaacuuuauguuaaacagaauacuuaagucuaug gauaaaaguauagauaccuuaucagaaauaaguggagcugcagaguugga cagaacagaagaguaugcucuugguguaguuggagugcuagagaguuaua uaggaucaauaaauaauauaacuaaacaaucagcauguguugccaugagc aaacuccucacugaacucaauagugaugauaucaaaaaacugagagacaa ugaagagcuaaauucacccaagauaagaguguacaauacugucauaucau auauugaaagcaacaggaaaaacaauaaacaaacuauccaucuguuaaaa agauugccagcagacguauugaagaaaaccaucaaaaacacauuggauau ccacaagagcauaaccaucaacaacccaaaagaauuaacuguuagugaua caaaugaccaugccaaaaauaaugauacuaccuga mRNA Coding for the Protein M2-2 of the RSV Strain ATCC VR-26 Long:

mRNA sequence according to SEQ ID No. 19:
augaccaugccaaaaauaaugauacuaccugacaaauauccuuguaguau aacuuccauacuaauaacaaguagauguagagucacuauguauaaucgaa agaacacacuauauuucaaucaaaacaacccaaauaaccauauguacuca ccgaaucaaacauucaaugaaauccauuggaccucacaagacuugauuga cacaauucaaaauuuucuacagcaucuagguguuauugaggauauauaua caauauauauauuagugucauaa mRNA Coding for the Phosphoprotein P of the RSV Strain ATCC VR-26 Long:

mRNA sequence according to SEQ ID No. 20:
auggaaaaguuugcuccugaauuccauggagaagaugcaaacaacagggc uacuaaauuccuagaaucaauaaagggcaaauucacaucaccuaaagauc ccaagaaaaaagauaguaucauaucugucaacucaauagauauagaagua accaaagaaagcccuauaacaucaaauucaaccauuauuaacccaacaaa ugagacagaugauaaugcagggaacaagcccaauuaucaaagaaaaccuc uaguaaguuucaaagaagacccuauaccaagugauaaucccuuuucaaaa cuauacaaagaaaccauagagacauuugauaacaaugaagaagaaucuag cuauucauaugaagaaauaaaugaucagacgaacgauaauauaacugcaa gauuagauaggauugaugaaaaauuaagugaaauacuaggaaugcuucac acauuaguaguagcaagugcaggaccuacaucugcuagggaugguauaag agaugccaugguugguuuaagagaagaaaugauagaaaaaaucagaacug aagcauuaaugaccaaugacagauuagaagcuauggcaagacucaggaau gaggaaagugaaaagauggcaaaagacacaucagaugaagugucucucaa uccaacaucagagaaauugaacaaccuguuggaagggaaugauagugaca augaucuaucacuugaagauuucuga mRNA Coding for the Non-Structural Protein NS1 of the RSV Strain ATCC VR-26 Long:

mRNA sequence according to SEQ ID No. 21:
augggcagcaauucguugaguaugauaaaaguuagauuacaaaauuuguu ugacaaugaugaaguagcauuguuaaaaauaacaugcuauacugacaaau uaauacauuuaacuaaugcuuuggcuaaggcagugauacauacaaucaaa -continued

```
uugaauggcauuguguuugugcauguuauuacaaguagugauauuugccc

uaauaauaauauuguaguaaaauccaauuucacaacaaugccagugcuac

aaaauggagguuauauaugggaaaugauggaauuaacacauugcucucaa

ccuaauggucuaauagaugacaauugugaaauuaaauucuccaaaaaacu

aagugauucaacaaugaccaauuauaugaaucaauuaucugaauuacuug

gauuugaucuuaauccauaa
```

mRNA Coding for the Non-Structural Protein NS2 of the RSV Strain ATCC VR-26 Long:

```
mRNA sequence according to SEQ ID No. 22:
auggacacaacccacaaugauaccacaccacaaagacugaugaucacaga

caugagaccguugucacuugagacuacaauaacaucacuaaccagagaca

ucauaacacacagauuuauauacuuaauaaaucaugaaugcauagugaga

aaacuugaugaaagacaggccacauuuacauuccuggucaacuaugaaau

gaaacuauugcacaaaguaggaagcacuaaauauaaaaaauauacugaau

acaacacaaaauauggcacuuucccuaugccgauauucaucaaucaugau

ggguucuuagaaugcauuggcauuaagccuacaaagcauacucccauaau

auacaaguaugaucucaauccauag
```

In the context of the invention, additionally to the here disclosed nucleic acid sequences, also nucleic acid sequences of different Respiratory syncytial virus (RSV) isolates are incorporated herewith. These different Respiratory syncytial virus (RSV) isolates show preferably an identity of at least 50%, 60%, 70%, more preferably of at least 80% and most preferably of at least 90% with the nucleic acid sequences according to SEQ ID Nos. 12-22 or of fragments thereof.

In a preferred embodiment, the mRNA sequence according to the invention does not comprise a reporter gene or a marker gene. Preferably, the mRNA sequence according to the invention does not encode, for instance, luciferase; green fluorescent protein (GFP) and its variants (such as eGFP, RFP or BFP); α-globin; hypoxanthine-guanine phosphoribosyltransferase (HGPRT); β-galactosidase; galactokinase; alkaline phosphatase; secreted embryonic alkaline phosphatase (SEAP)) or a resistance gene (such as a resistance gene against neomycin, puromycin, hygromycin and zeocin). In a preferred embodiment, the mRNA sequence according to the invention does not encode luciferase. In another embodiment, the mRNA sequence according to the invention does not encode GFP or a variant thereof.

In a further preferred embodiment, the mRNA sequence according to the invention does not encode a protein (or a fragment of a protein) derived from a virus belonging to the family of Orthomyxoviridae. Preferably the mRNA sequence does not encode a protein that is derived from an influenza virus, more preferably an influenza A virus. Preferably, the mRNA sequence according to the invention does not encode an influenza A protein selected from the group consisting of hemagglutinin (HA), neuraminidase (NA), nucleoprotein (NP), M1, M2, NS1, NS2 (NEP: nuclear export protein), PA, PB1 (polymerase basic 1), PB1-F2 and PB2. In another preferred embodiment, the mRNA according to the invention does not encode ovalbumin (OVA) or a fragment thereof. Preferably, the mRNA sequence according to the invention does not encode an influenza A protein or ovalbumin.

By a further embodiment, the inventive mRNA preferably comprises at least one of the following structural elements: a 5'- and/or 3'-untranslated region element (UTR element), particularly a 5'-UTR element which comprises or consists of a nucleic acid sequence which is derived from the 5'-UTR of a TOP gene or from a fragment, homolog or a variant thereof, or a 5'- and/or 3'-UTR element which may be derivable from a gene that provides a stable mRNA or from a homolog, fragment or variant thereof; a histone-stem-loop structure, preferably a histone-stem-loop in its 3' untranslated region; a 5'-CAP structure; a poly-A tail; or a poly(C) sequence.

In a preferred embodiment of the first aspect of the present invention, the inventive mRNA comprises at least one 5'- or 3'-UTR element. In this context, an UTR element comprises or consists of a nucleic acid sequence which is derived from the 5'- or 3'-UTR of any naturally occurring gene or which is derived from a fragment, a homolog or a variant of the 5'- or 3'-UTR of a gene. Preferably, the 5'- or 3'-UTR element used according to the present invention is heterologous to the coding region of the inventive mRNA sequence. Even if 5'- or 3'-UTR elements derived from naturally occurring genes are preferred, also synthetically engineered UTR elements may be used in the context of the present invention.

In a particularly preferred embodiment of the first aspect of the present invention, the inventive mRNA sequence comprises at least one 5'-untranslated region element (5'UTR element) which comprises or consists of a nucleic acid sequence which is derived from the 5'UTR of a TOP gene or which is derived from a fragment, homolog or variant of the 5'UTR of a TOP gene.

It is particularly preferred that the 5'UTR element does not comprise a TOP-motif or a 5'TOP, as defined above.

In some embodiments, the nucleic acid sequence of the 5'UTR element which is derived from a 5'UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'UTR element does not comprise any part of the protein coding region. Thus, preferably, the only protein coding part of the inventive mRNA is provided by the coding region.

The nucleic acid sequence, which is derived from the 5'UTR of a TOP gene, is derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element is preferably selected from 5'-UTR elements comprising or consisting of a nucleic acid sequence, which is derived from a nucleic acid sequence selected from the group consisting of SEQ ID Nos. 1-1363, SEQ ID NO. 1395, SEQ ID NO. 1421 and SEQ ID NO. 1422 of the patent application WO2013/143700, whose disclosure is incorporated herein by reference, from the homologs of SEQ ID Nos. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID Nos. 1-1363, SEQ ID NO. 1395, SEQ ID NO. 1421 and SEQ ID NO. 1422 of the patent application WO2013/143700" refers to sequences of other species than *Homo sapiens*, which are homologous to the sequences according to SEQ ID Nos. 1-1363, SEQ ID NO. 1395, SEQ ID NO. 1421 and SEQ ID NO. 1422 of the patent application WO2013/143700.

In a preferred embodiment, the 5'UTR element comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'UTR element comprises or consists of a nucleic acid sequence, which is derived from a 5'UTR of a TOP gene encoding a ribosomal protein or from a variant of a 5'UTR of a TOP gene encoding a ribosomal protein. For example, the 5'UTR element comprises or consists of a nucleic acid sequence which is derived from a 5'UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3' end of the sequences) corresponds to the 5'UTR of said sequences.

Preferably, the 5'UTR element comprises or consists of a nucleic acid sequence which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence which is derived from a 5'UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5' TOP motif.

In a particularly preferred embodiment, the 5'UTR element comprises or consists of a nucleic acid sequence which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 23 (5'-UTR of human ribosomal protein Large 32 lacking the 5' terminal oligopyrimidine tract: GGCGCTGCCTACGGAGGTGGCAGC-CATCTCCTTCTCGGCATC; corresponding to SEQ ID No. 1368 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 23 or more preferably to a corresponding RNA sequence, wherein, preferably, the fragment is as described above, i.e. being a continuous stretch of nucleotides representing at least 20%, preferably at least 30%, more preferably at least 40%, more preferably at least 50%, even more preferably at least 60%, even more preferably at least 70%, even more preferably at least 80%, and most preferably at least 90%. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the inventive mRNA comprises a 5'UTR element which comprises or consists of a nucleic acid sequence which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5' terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'UTR element comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 36 (5'-UTR of ATP5A1 lacking the 5' terminal oligopyrimidine tract: GCGGCTCGGCCATTTTGTCCCAGTCAGTCCGGAGGCTGCGGCTGCAG AAGTACCGCC TGCG-GAGTAACTGCAAAG; corresponding to SEQ ID No. 1414 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 26 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a further preferred embodiment, the inventive mRNA further comprises at least one 3'UTR element, which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

The term '3'UTR element' refers to a nucleic acid sequence which comprises or consists of a nucleic acid sequence that is derived from a 3'UTR or from a variant of a 3'UTR. A 3'UTR element in the sense of the present invention may represent the 3'UTR of an mRNA. Thus, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence which corresponds to the 3'UTR of an mRNA, preferably to the 3'UTR of an artificial mRNA, such as an mRNA obtained by transcription of a genetically engineered vector construct. Preferably, the 3'UTR element fulfils the function of a 3'UTR or encodes a sequence which fulfils the function of a 3'UTR.

Preferably, the inventive mRNA comprises a 3'UTR element which may be derivable from a gene that relates to an mRNA with an enhanced half-life (that provides a stable mRNA), for example a 3'UTR element as defined and described below.

In a particularly preferred embodiment, the 3'UTR element comprises or consists of a nucleic acid sequence which is derived from a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID No. 1369-1390 of the patent application WO2013/143700 whose disclosure is incorporated herein by reference. In a particularly preferred embodiment, the 3'UTR element comprises or consists of a nucleic acid sequence which is derived from a 3'UTR of an albumin gene, preferably a vertebrate albumin gene, more preferably a mammalian albumin gene, most preferably a human albumin gene according to SEQ ID No. 24.

```
Human albumin 3'UTR SEQ ID No. 24:
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT
(corresponding to SEQ ID No: 1369 of the
patent application WO2013/143700).
```

In this context, it is particularly preferred that the inventive mRNA comprises a 3'-UTR element comprising a corresponding RNA sequence derived from the nucleic acids according to SEQ ID No. 1369-1390 of the patent application WO2013/143700 or a fragment, homolog or variant thereof.

Most preferably the 3'-UTR element comprises the nucleic acid sequence derived from a fragment of the human albumin gene according to SEQ ID No. 25:

```
albumin7 3'UTR
CATCACATTTAAAAGCATCTCAGCCTACCATGAGAATAAGAGAAAGAAAA

TGAAGATCAATAGCTTATTCATCTCTTTTTCTTTTTCGTTGGTGTAAAGC

CAACACCCTGTCTAAAAAACATAAATTTCTTTAATCATTTTGCCTCTTTT

CTCTGTGCTTCAATTAATAAAAAATGGAAAGAACCT
(SEQ ID No. 25 corresponding to SEQ ID No: 1376 of
the patent application WO2013/143700)
```

In this context, it is particularly preferred that the 3'-UTR element of the inventive mRNA comprises or consists of a corresponding RNA sequence of the nucleic acid sequence according to SEQ ID No. 25.

In another particularly preferred embodiment, the 3'UTR element comprises or consists of a nucleic acid sequence which is derived from a 3'UTR of an α-globin gene, preferably a vertebrate α- or β-globin gene, more preferably a mammalian α- or β-globin gene, most preferably a human α- or β-globin gene according to SEQ ID No. 26-28:

```
3'-UTR of Homo sapiens hemoglobin, alpha 1 (HBA1)
GCTGGAGCCTCGGTGGCCATGCTTCTTGCCCCTTGGGCCTCCCCCCAGCC

CCTCCTCCCCTTCCTGCACCCGTACCCCCGTGGTCTTTGAATAAAGTCTG

AGTGGGCGGC
(SEQ ID No: 26 corresponding to SEQ ID No. 1370 of
the patent application WO2013/143700)
```

```
3'-UTR of Homo sapiens hemoglobin, alpha 2 (HBA2)
GCTGGAGCCTCGGTAGCCGTTCCTCCTGCCCGCTGGGCCTCCCAACGGGC

CCTCCTCCCCTCCTTGCACCGGCCCTTCCTGGTCTTTGAATAAAGTCTGA

GTGGGCAG
(SEQ ID No: 27 corresponding to SEQ ID No. 1371 of
the patent application WO2013/143700)
```

```
3'-UTR of Homo sapiens hemoglobin, beta (HBB)
GCTCGCTTTCTTGCTGTCCAATTTCTATTAAAGGTTCCTTTGTTCCCTAA

GTCCAACTACTAAACTGGGGGATATTATGAAGGGCCTTGAGCATCTGGAT

TCTGCCTAATAAAAAACATTTATTTTCATTGC
(SEQ ID No: 28 corresponding to SEQ ID No. 1372 of
the patent application WO2013/143700)
```

For example, the 3'UTR element may comprise or consist of the center, α-complex-binding portion of the 3'UTR of an α-globin gene, such as of a human α-globin gene, preferably according to SEQ ID No. 29:

```
Center, α-complex-binding portion of the 3'UTR of
an α-globin gene (also named herein as "muag")
GCCCGATGGGCCTCCCAACGGGCCCTCCTCCCCTCCTTGCACCG
(SEQ ID NO. 29 corresponding to SEQ ID No. 1393 of
the patent application WO2013/143700).
```

In this context, it is particularly preferred that the 3'-UTR element of the inventive mRNA comprises or consists of a corresponding RNA sequence of the nucleic acid sequence according to SEQ ID No. 29 or a homolog, a fragment or variant thereof.

The term 'a nucleic acid sequence which is derived from the 3'UTR of a [ . . . ] gene' preferably refers to a nucleic acid sequence which is based on the 3'UTR sequence of a [ . . . ] gene or on a part thereof, such as on the 3'UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term 'a nucleic acid sequence which is derived from a variant of the 3'UTR of a [ . . . ] gene' preferably refers to a nucleic acid sequence which is based on a variant of the 3'UTR sequence of a gene, such as on a variant of the 3'UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

Preferably, the at least one 5'UTR element and the at least one 3'UTR element act synergistically to increase protein production from the inventive mRNA as described above.

In a particularly preferred embodiment, the inventive mRNA comprising a coding region, encoding at least one antigenic peptide or protein of Respiratory syncytial virus (RSV) or a fragment, variant or derivative thereof, comprises a histone stem-loop sequence/structure. Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

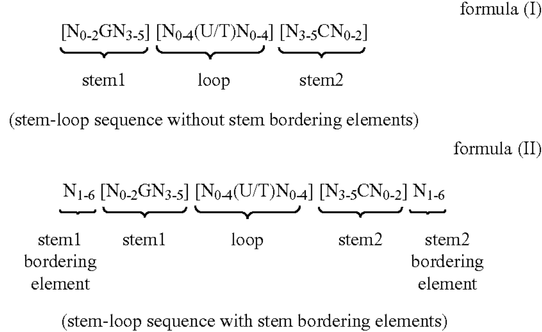

wherein:

stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}\ GN_{3-5}]$ is reverse complementary or partially reverse complementary with element stem2, and is a consecutive sequence between of 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence $[N_{0-4}\ (U/T)N_{0-4}]$ is located between elements stem1 and stem2, and is a consecutive sequence of 3 to 5 nucleotides, more preferably of 4 nucleotides;

wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}\ CN_{0-2}]$ is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment of the first inventive aspect, the inventive mRNA sequence may comprise at least one histone stem-loop sequence according to at least one of the following specific formulae (Ia) or (IIa):

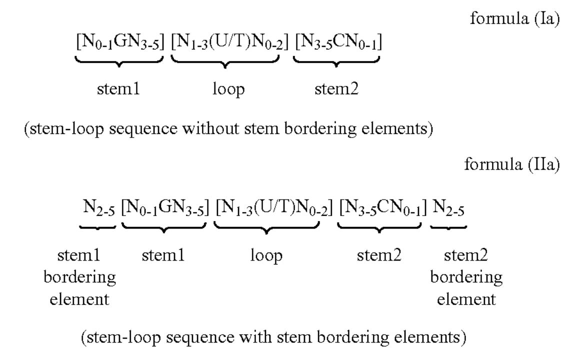

wherein:

N, C, G, T and U are as defined above.

According to a further more particularly preferred embodiment of the first aspect, the inventive mRNA sequence may comprise at least one histone stem-loop sequence according to at least one of the following specific formulae (Ib) or (IIb):

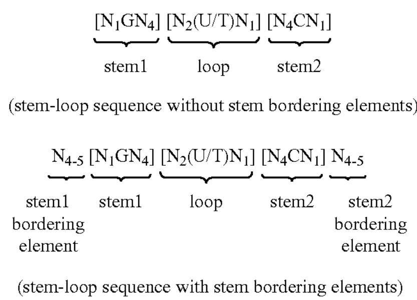

wherein:

N, C, G, T and U are as defined above.

A particular preferred histone stem-loop sequence is the sequence according to SEQ ID NO: 30 CAAAGGCTCTTTTCAGAGCCACCA or more preferably the corresponding RNA sequence of the nucleic acid sequence according to SEQ ID NO: 30 (CAAAGGCUCUUUUCAGAGCCACCA SEQ ID NO: 37).

In a particular preferred embodiment of the first aspect of the present invention the inventive mRNA comprises additionally to the coding region encoding at least one antigenic peptide or protein of Respiratory syncytial virus (RSV) or a fragment, variant or derivative thereof, a poly(A) sequence, also called poly-A-tail, preferably at the 3'-terminus of the inventive mRNA. When present, such a poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context, the term "about" refers to a deviation of ±10% of the value(s) it is attached to. This poly(A) sequence is preferably located 3' of the coding region comprised in the inventive mRNA according to the first aspect of the present invention.

According to a further preferred embodiment, the inventive mRNA can be modified by a sequence of at least 10 cytosines, preferably at least 20 cytosines, more preferably at least 30 cytosines (so-called "poly(C) sequence"). Particularly, the mRNA may contain a poly(C) sequence of typically about 10 to 200 cytosine nucleotides, preferably about 10 to 100 cytosine nucleotides, more preferably about 10 to 70 cytosine nucleotides or even more preferably about 20 to 50 or even 20 to 30 cytosine nucleotides. This poly(C) sequence is preferably located 3' of the coding region, more preferably 3' of an optional poly(A) sequence comprised in the inventive mRNA according to the first aspect of the present invention.

In this context, the inventive mRNA sequence may comprise in a specific embodiment:

a.) a 5'-CAP structure, preferably m7GpppN;

b.) a coding region encoding at least one antigenic peptide or protein of Respiratory syncytial virus (RSV), preferably derived from the fusion protein F of Respiratory syncytial virus (RSV);

c.) a poly(A) sequence preferably comprising 64 adenosines; and d.) optionally, a poly(C) sequence, preferably comprising 30 cytosines.

In a particularly preferred embodiment of the first aspect of the present invention the inventive mRNA comprising a coding region encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;

b.) a coding region encoding at least one antigenic peptide or protein of Rabies virus, preferably derived from the glycoprotein G (RAV-G) of Rabies virus;

c.) a poly(A) sequence preferably comprising 64 adenosines;

d.) optionally, a poly(C) sequence, preferably comprising 30 cytosines; and e.) a histone-stem-loop, preferably comprising the corresponding RNA sequence of the nucleic acid sequence according to SEQ ID NO: 30.

In a further particularly preferred embodiment of the first aspect of the present invention, the inventive mRNA comprising a coding region encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;

b.) a coding region encoding at least one antigenic peptide or protein of Respiratory syncytial virus (RSV), preferably derived from the fusion protein F of Respiratory syncytial virus (RSV);

c.) optionally, a 3'-UTR element derived from an alpha globin gene, preferably comprising the corresponding RNA sequence of the nucleic acid sequence according to SEQ ID NO. 29, a homolog, a fragment, or a variant thereof;

d.) a poly(A) sequence preferably comprising 64 adenosines;

e.) optionally, a poly(C) sequence, preferably comprising 30 cytosines; and f.) a histone-stem-loop, preferably comprising the corresponding RNA sequence of the nucleic acid sequence according to SEQ ID NO: 30.

In another particular preferred embodiment, the inventive mRNA encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;

b.) optionally, a 5'-UTR element derived from a TOP gene, preferably derived from the corresponding RNA sequence of the nucleic acid sequence according to SEQ ID NO. 23, a homolog, a fragment, or a variant thereof;

c.) a coding region encoding at least one antigenic peptide or protein of Respiratory syncytial virus (RSV), preferably derived from the fusion protein F of Respiratory syncytial virus (RSV);

d.) optionally, a 3'UTR element derived of a gene providing a stable mRNA, preferably derived from the corresponding RNA sequence of a nucleic acid sequence according to SEQ ID NO. 25, a homolog, a fragment, or a variant thereof;

e.) a poly(A) sequence preferably comprising 64 adenosines;

f.) optionally, a poly(C) sequence, preferably comprising 30 cytosines; and g.) a histone-stem-loop, preferably comprising the corresponding RNA sequence of the nucleic acid sequence according to SEQ ID NO: 30.

The coding region might encode at least partially one of the amino acid sequences according to SEQ ID Nos. 1-11 or fragments, variants or derivatives thereof. Furthermore, the coding region of the inventive mRNA may encode a combination of at least two of these amino acid sequences or a combination of fragments, variants or derivatives thereof. Particularly preferred in this context is a combination of fusion protein F with nucleoprotein N and a combination of fusion protein F and M2-1 protein.

Additionally the coding region might be or might comprise at least partially one of the sequences according to SEQ ID No. 12 to SEQ ID No. 22, or fragments, homologs or variants thereof. Furthermore, the mRNA might comprise a combination of at least two of these sequences or a combination of fragments, homologs or variants thereof.

For further improvement of the resistance to e.g. in vivo degradation (e.g. by an exo- or endo-nuclease), the inventive mRNA may be provided as a stabilized nucleic acid, e.g. in the form of a modified nucleic acid. According to a further embodiment of the invention it is therefore preferred that the inventive mRNA is stabilized, preferably by backbone modifications, sugar modifications and/or base modifications, more preferred stabilized by modification of the G/C-content. All of these modifications may be introduced into the inventive mRNA without impairing the mRNA's function to be translated into the antigenic function derived from the Respiratory syncytial virus (RSV) peptide or protein.

A backbone modification in the context of the present invention is preferably a modification in which phosphates of the backbone of the nucleotides contained in the inventive mRNA are chemically modified, e.g. anionic internucleoside linkage, N3'→P5' modifications, replacement of non-bridging oxygen atoms by boranes, neutral internucleoside linkage, amide linkage of the nucleosides, methylene(methylimino) linkages, formacetal and thioformacetal linkages, introduction of sulfonyl groups, or the like.

A sugar modification in the context of the present invention is preferably a chemical modification of the sugar of the nucleotides of the inventive mRNA, e.g. methylation of the ribose residue or the like.

According to another embodiment, the inventive mRNA may be modified and thus stabilized by modifying the G (guanosine)/C (cytosine) content of the mRNA, preferably of the coding region thereof.

Therein, the G/C content of the inventive mRNA, preferably of the coding region, is particularly increased compared to the G/C content of the coding region of its particular wild type coding sequence, i.e. the unmodified mRNA. However, the encoded amino acid sequence of the inventive mRNA is preferably not modified compared to the coded amino acid sequence of the particular wild type/unmodified mRNA.

The modification of the G/C-content of the inventive mRNA is based on the fact that RNA sequences having an increased G (guanosine)/C (cytosine) content are more stable than RNA sequences having an increased A (adenosine)/U (uracil) content. The codons of a coding sequence or a whole RNA might therefore be varied compared to the wild type coding sequence or mRNA, such that they include an increased amount of G/C nucleotides while the translated amino acid sequence is retained. In respect to the fact that several codons code for one and the same amino acid (so-called degeneration of the genetic code), the most favourable codons for the stability can be determined (so-called alternative codon usage). Preferably, the G/C content of the coding region of the inventive mRNA according to the invention is increased by at least 7%, more preferably by at least 15%, particularly preferably by at least 20%, compared to the G/C content of the coded region of the wild type RNA. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence. In this context, it is particularly preferable to increase the G/C content of the inventive mRNA to the maximum (i.e. 100% of the substitutable codons), in particular in the coding region, compared to the wild type sequence.

According to a further preferred embodiment of the invention, the inventive mRNA is optimized for translation, preferably optimized for translation by replacing codons for less frequent tRNAs of a given amino acid by codons for more frequently occurring tRNAs of the respective amino acid. This is based on the finding that the translation efficiency is also determined by a different frequency in the occurrence of tRNAs in cells. Thus, if so-called "less frequent codons" are present in the inventive mRNA to an increased extent, the corresponding modified RNA is translated to a significantly poorer degree than in the case where codons coding for more frequent tRNAs are present. Preferably, the coding region of the inventive mRNA is modified compared to the corresponding region of the wild type RNA or coding sequence such that at least one codon of the wild type sequence which codes for a tRNA which is relatively rare or less frequent in the cell is exchanged for a codon which codes for a tRNA which is more or most frequent in the cell and carries the same amino acid as the relatively rare or less frequent tRNA. By this modification, the sequences of the inventive mRNA can be modified such that codons for which more frequently occurring tRNAs are available are inserted. In other words, according to the invention, by this modification all codons of the wild type sequence which code for a tRNA which is relatively rare in the cell can in each case be exchanged for a codon which codes for a respective tRNA which is relatively frequent in the cell and which, in each case, carries the same amino acid as the relatively rare tRNA. Furthermore, it is particularly preferable to link the sequential G/C content which is increased, in particular maximized, in the inventive mRNA with the "frequent" codons without modifying the amino acid sequence of the protein encoded by the coding region of the inventive mRNA or of the coding region. This preferred embodiment allows provision of a particularly efficiently translated and stabilized (modified) inventive mRNA.

Substitutions, additions or eliminations of bases are preferably carried out using a DNA matrix for preparation of the nucleic acid molecule by techniques of the well known site directed mutagenesis or with an oligonucleotide ligation. In such a process, for preparation of the at least one RNA of the inventive combination vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one RNA to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

In a particularly preferred embodiment, the inventive mRNA sequence according to the first aspect of the present invention comprises, preferably in 5'- to 3'-direction:

a) a 5'-CAP structure, as defined herein, preferably m7GpppN;
b) a coding region, preferably with an increased or even maximized G/C content compared with the G/C content of the coding region of the wild type mRNA, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV), or a fragment, variant or derivative thereof;
c) a 3'-UTR element as defined herein, preferably derived of a gene providing a stable mRNA, most preferably the corresponding RNA sequence of the nucleic acid sequence according to SEQ ID No. 29, or a homolog, a fragment or variant thereof;
d) a poly(A) sequence, preferably consisting of 64 adenosines
e) optionally a poly(C) sequence, preferably consisting of 30 cytosines.
f) at least one histone stem-loop sequence, preferably the corresponding RNA sequence of the nucleic acid sequence according to SEQ ID NO. 30.

Most preferably, the inventive mRNA sequence of that specific embodiment comprises the sequence modifications as shown in FIG. 1 (SEQ ID NO. 31) using the example of an inventive mRNA coding for the fusion protein F of RSV long.

In a further particularly preferred embodiment, the inventive mRNA sequence according to the first aspect of the present invention comprises preferably in 5' to 3' direction:

a) a 5'-CAP structure, as defined herein, preferably preferably m7GpppN;
b) a 5'-UTR element as defined herein, preferably a 5'-UTR element which comprises or consists of a nucleic acid sequence which is derived from the 5'-UTR of a TOP gene, preferably the 5'-UTR of human ribosomal protein Large 32 lacking the 5' terminal oligopyrimidine tract according to SEQ ID No. 23 or the corresponding RNA sequence; or a fragment, homolog or variant thereof;
c) a coding region, preferably with an increased or even maximized G/C content compared with the G/C content of the coding region of the wild type mRNA, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof;
d) a 3'-UTR element, preferably the 3'-UTR element of human albumin according to SEQ ID No. 24 or the corresponding RNA, or a homolog, a fragment or a variant thereof;
e) a poly(A) sequence, preferably consisting of 64 adenosines
f) optionally a poly(C) sequence, preferably consisting of 30 cytosines.
g) at least one histone stem-loop sequence, preferably the corresponding RNA sequence of the nucleic acid sequence according to SEQ ID NO. 30.

Most preferably, the inventive mRNA of that specific embodiment comprises the sequence modifications as shown in FIG. 2 (SEQ ID NO. 32) using the example of an inventive mRNA coding for the fusion protein F of RSV long.

In an even more particularly preferred embodiment the inventive mRNA sequence comprises or consists of the sequences shown in FIG. 1-5 according to SEQ ID Nos. 31 and 35.

In further specific embodiments, the mRNA according to the invention may further comprise an internal ribosome entry site (IRES) sequence or IRES-motif, which may separate several open reading frames, for example if the inventive mRNA encodes for two or more antigenic peptides or proteins. An IRES-sequence may be particularly helpful if the mRNA is a bi- or multicistronic mRNA.

Additionally, the inventive mRNA may be prepared using any method known in the art, including synthetic methods such as e.g. solid phase synthesis, as well as in vitro methods, such as in vitro transcription reactions.

According to one embodiment of the present invention the mRNA comprising a coding region, encoding at least one antigenic peptide or protein of Respiratory syncytial virus (RSV) or a fragment, variant or derivative thereof may be administered naked without being associated with any further vehicle, transfection or complexation agent for increasing the transfection efficiency and/or the immunostimulatory properties of the inventive mRNA or of further comprised nucleic acid.

In a preferred embodiment, the inventive mRNA may be formulated together with a cationic or polycationic compound and/or with a polymeric carrier. Accordingly, in a further embodiment of the invention it is preferred that the inventive mRNA or any other nucleic acid comprised in the inventive pharmaceutical composition or vaccine is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of mRNA or nucleic acid to cationic or polycationic compound and/or with a polymeric carrier; or optionally in a nitrogen/phosphate ratio of mRNA or nucleic acid to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9.

Thereby, the inventive mRNA or any other nucleic acid comprised in the inventive pharmaceutical composition or vaccine can also be associated with a vehicle, transfection or complexation agent for increasing the transfection efficiency and/or the immunostimulatory properties of the inventive mRNA or of optionally comprised further included nucleic acids.

Cationic or polycationic compounds, being particularly preferred agents in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, plsl, FGF, Lactoferrin, Transportan, Buforin-2, Bac715-24, SynB, SynB(1), pVEC, hCT-derived peptides, SAP, or histones.

In this context, protamine is particularly preferred.

Additionally, preferred cationic or polycationic proteins or peptides may be selected from the following proteins or peptides having the following total formula (III):

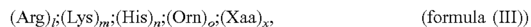

$(Arg)_l;(Lys)_m;(His)_n;(Orn)_o;(Xaa)_x$, (formula (III))

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. In this context the disclosure of WO 2009/030481 is incorporated herewith by reference.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIPS: rac-[2 (2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

A polymeric carrier used according to the invention might be a polymeric carrier formed by disulfide-crosslinked cationic components. The disulfide-crosslinked cationic components may be the same or different from each other. The polymeric carrier can also contain further components. It is also particularly preferred that the polymeric carrier used according to the present invention comprises mixtures of cationic peptides, proteins or polymers and optionally further components as defined herein, which are crosslinked by disulfide bonds as described herein. In this context, the disclosure of WO 2012/013326 is incorporated herewith by reference.

In this context, the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex an mRNA or a nucleic acid as defined according to the present invention, and thereby preferably condensing the mRNA or the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to complex the inventive mRNA or any further nucleic acid comprised in the inventive pharmaceutical composition or vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex the inventive mRNA or any further nucleic acid comprised in the inventive pharmaceutical composition or vaccine may be formed by disulfide-crosslinked cationic (or polycationic) components.

Preferably, such cationic or polycationic peptides or proteins or polymers of the polymeric carrier, which comprise or are additionally modified to comprise at least one —SH moiety, are selected from, proteins, peptides and polymers as defined above for complexation agent.

In a further particular embodiment, the polymeric carrier which may be used to complex the inventive mRNA or any further nucleic acid comprised in the inventive pharmaceutical composition or vaccine may be selected from a polymeric carrier molecule according to generic formula (IV):

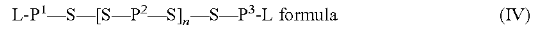

$L\text{-}P^1—S—[S—P^2—S]_n—S—P^3\text{-}L$ formula (IV)

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), $(AA)_x$, or $[(AA)_x]_z$ if such components are used as a linker between $P^1$ and $P^2$ or $P^3$ and $P^2$) and/or with further components (e.g. (AA), $(AA)_x$, $[(AA)_x]_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_x$, or $[(AA)_x]_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_x$, $[(AA)_x]_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In this context the disclosure of WO 2011/026641 is incorporated herewith by reference. Each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (V) above (the brackets are omitted for better readability), wherein any of S, $P^1$ and $P^3$ are as defined herein, typically represent a situation, wherein one-SH-moiety of hydrophilic polymers $P^1$ and $P^3$ was condensed with one —SH-moiety of component $P^2$ of generic formula (V) above, wherein both sulphurs of these —SH-moieties form a disulfide bond —S—S— as defined herein in formula (V). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH-moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, α,β unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH— moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

In this context, it is particularly preferred that the inventive mRNA is complexed at least partially with a cationic or polycationic compound and/or a polymeric carrier, preferably cationic proteins or peptides. In this context the disclosure of WO 2010/037539 and WO 2012/113513 is incorporated herewith by reference. Partially means that only a part of the inventive mRNA is complexed with a cationic compound and that the rest of the inventive mRNA is (comprised in the inventive pharmaceutical compostion or vaccine) in uncomplexed form ("free"). Preferably the ratio of complexed mRNA to: free mRNA (in the inventive pharmaceutical composition or vaccine) is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed mRNA to free mRNA in the inventive pharmaceutical composition or vaccine is selected from a ratio of about 1:1 (w/w).

The complexed mRNA in the inventive pharmaceutical composition or vaccine, is preferably prepared according to a first step by complexing the inventive mRNA with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed mRNA after complexing the mRNA. Accordingly, the ratio of the mRNA and the cationic or polycationic compound and/or the polymeric carrier in the component of the complexed mRNA is typically selected in a range that the mRNA is entirely complexed and no free cationic or polycationic compound or polymeric carrier or only a negligibly small amount thereof remains in the composition.

Preferably the ratio of the mRNA to the cationic or polycationic compound and/or the polymeric carrier, preferably as defined herein, is selected from a range of about 6:1 (w/w) to about 0,25:1 (w/w), more preferably from about 5:1 (w/w) to about 0,5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the mRNA to the cationic or polycationic compound and/or the polymeric carrier, preferably as defined herein, in the component of the complexed mRNA, may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of mRNA: cationic or polycationic compound and/or polymeric carrier, preferably as defined herein, in the complex, and most preferably in a range of about 0.7-1,5, 0.5-1 or 0.7-1, and even most preferably in a range of about 0.3-0.9 or 0.5-0.9., preferably provided that the cationic or polycationic compound in the complex is a cationic or polycationic cationic or polycationic protein or peptide and/or the polymeric carrier as defined above. In this specific embodiment the complexed mRNA is also emcompassed in the term "adjuvant component".

In a further aspect, the invention provides for a composition comprising a plurality or more than one, preferably 2 to 10, more preferably 2 to 5, most preferably 2 to 4 of the inventive mRNA sequences as defined herein. These inventive compositions comprise more than one inventive mRNA sequences, preferably encoding different peptides or proteins which comprise preferably different pathogenic antigens or fragments, variants or derivatives thereof. Particularly preferred in this context is that at least one mRNA sequence encodes at least one antigenic peptide or protein derived from the fusion protein F of Respiratory syncytial virus (RSV) and that at least one mRNA sequence encodes at least one antigenic peptide or protein derived from another antigen of Respiratory syncytial virus (RSV), particularly of nucleoprotein N or M2-1 protein. Further particularly preferred combinations of antigens are in this context:

F+G (serotype A)+G (serotype B)
F+G (serotype A)+G (serotype B)+M2-1
F+G (serotype A)+G (serotype B)+N
F+G (serotype A)+G (serotype B)+N+M2-1
F+M2-1+N
F+M2-1
F+N
F+G (serotype A)+G (serotype B)+N+M2-1+P+M2-2+M+L
F+G (serotype A)+G (serotype B)+N+M2-1+P+M2-2+M
F+G (serotype A)+G (serotype B)+N+M2-1+P+M2-2+L
F+G (serotype A)+G (serotype B)+N+M2-1+P+M+L
F+G (serotype A)+G (serotype B)+N+M2-1+M2-2+M+L
F+G (serotype A)+G (serotype B)+N+P+M2-2+M+L
F+G (serotype A)+G (serotype B)+M2-1+P+M2-2+M+L Accordingly, in a further particular preferred aspect, the present invention also provides a pharmaceutical composition, comprising at least one inventive mRNA sequence as defined herein or an inventive composition comprising a plurality of inventive mRNA sequences as defined herein and optionally a pharmaceutically acceptable carrier and/or vehicle.

As a first ingredient, the inventive pharmaceutical composition comprises at least one inventive mRNA sequence as defined herein.

As a second ingredient, the inventive pharmaceutical composition may optionally comprise at least one additional pharmaceutically active component. A pharmaceutically active component in this connection is a compound that has a therapeutic effect to heal, ameliorate or prevent a particular indication or disease as mentioned herein, preferably RSV infections. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc. Particularly preferred in this context are RSV vaccines, or RSV immune globulines, e.g. Palivizumab) (Synagis®).

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intraarticular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

In a preferred embodiment, the inventive pharmaceutical composition is administered via intradermal or intramuscular injection, preferably by using conventional needle-based injection technique or by using a needle-free system, e.g. jet injection. In a further preferred embodiment, the inventive pharmaceutical composition may be administered by jet injection as defined herein. Preferably, the inventive pharmaceutical composition may be adminstered intramuscularly by jet injection. According to another embodiment, the pharmaceutical composition is administered intradermally via jet injection.

In a preferred embodiment, the pharmaceutical composition may be administered once, twice or three times, preferably by intradermal or intramuscular injection, preferably by jet injection. According to a certain embodiment, a single administration of the inventive pharmaceutical composition, preferably via intradermal or intramuscular injection, preferably by using jet injection, is sufficient for eliciting an immune response against the at least one antigen encoded by the mRNA sequence according to the invention. In a preferred embodiment, the single administration of the pharmaceutical composition elicits an immune response resulting in virus neutralisation. In this context, one single intradermal or intramuscular injection of the pharmaceutical composition is particularly preferred. Preferably, further administrations of the pharmaceutical composition may optionally be carried out in order to enhance and/or prolong the immune response.

According to a specific embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive mRNA sequence as vehicle, transfection or complexation agent.

Furthermore, the inventive pharmaceutical composition may comprise one or more additional adjuvants, which are suitable to initiate or increase an immune response of the innate immune system, i.e. a non-specific immune response, particularly by binding to pathogen-associated molecular patterns (PAMPs). With other words, when administered, the pharmaceutical composition or vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following. According to one embodiment such an adjuvant may be selected from an adjuvant as defined above.

Also such an adjuvant may be selected from any adjuvant known to a skilled person and suitable for the present case, i.e. supporting the induction of an innate immune response in a mammal and/or suitable for depot and delivery of the components of the inventive pharmaceutical composition or vaccine. Preferred as adjuvants suitable for depot and delivery are cationic or polycationic compounds as defined above. Likewise, the adjuvant may be selected from the group consisting of, e.g., cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha, 25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo [4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-lbeta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (□β-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21);

Quil-A (Quil-A saponin); S-28463 (4-amino-otec-dimethyl-2-ethoxymethyl-1H-imidazo [4,5-c]quinoline-1-ethanol); SAF-1™ ("Syntex adjuvant formulation"); Sendai proteoliposomes and Sendai containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T-cells, such as GM-CSF, IL-12, IFNg, any immunostimulatory nucleic acid as defined above, preferably an immunostimulatory RNA, CpG DNA, etc.

In a further preferred embodiment, it is also possible that the inventive pharmaceutical composition contains besides the antigen-providing mRNA further components, which are selected from the group comprising: further antigens or further antigen-providing nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

The inventive pharmaceutical composition can additionally contain one or more auxiliary substances in order to increase its immunogenicity or immunostimulatory capacity, if desired. A synergistic action of the inventive mRNA sequence as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives, which may be included in the inventive pharmaceutical composition, are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

In this context, it is particularly preferred that the optionally comprised adjuvant component comprises the same inventive mRNA as comprised in the inventive pharmaceutical composition as antigen-providing mRNA e.g. mRNA coding for an antigenic peptide or protein of RSV infections Respiratory syncytial virus (RSV) or fragments, variants or derivatives thereof.

Despite, the inventive pharmaceutical composition may comprise further components for facilitating administration and uptake of components of the pharmaceutical composition. Such further components may be an appropriate carrier or vehicle, additional adjuvants for supporting any immune response, antibacterial and/or antiviral agents.

Accordingly, in a further embodiment, the inventive pharmaceutical composition furthermore comprises a pharmaceutically acceptable carrier and/or vehicle.

Such a pharmaceutically acceptable carrier typically includes the liquid or non-liquid basis of a composition comprising the components of the inventive pharmaceutical composition. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the pharmaceutical composition according to the invention. The term "compatible" as used here means that these constituents of the inventive pharmaceutical composition are capable of being mixed with the components of the inventive pharmaceutical composition in such a manner that no interaction occurs which would substantially reduce the pharmaceutical effectiveness of the pharmaceutical composition under typical use conditions.

A further component of the inventive pharmaceutical composition may be an immunotherapeutic agent that can be selected from immunoglobulins, preferably IgGs, monoclonal or polyclonal antibodies, polyclonal serum or sera, etc, most preferably immunoglobulins directed against Respiratory syncytial virus (RSV), e.g. Palivizumab. Preferably, such a further immunotherapeutic agent may be provided as a peptide/protein or may be encoded by a nucleic acid, preferably by a DNA or an RNA, more preferably an mRNA. Such an immunotherapeutic agent allows providing passive vaccination additional to active vaccination triggered by the inventive antigen-providing mRNA.

Furthermore, in a specific embodiment, additionally to the antigen-providing mRNA further antigens can be included in the inventive pharmaceutical composition and are typically substances such as cells, cell lysates, viruses, attenuated viruses, inactivated viruses, proteins, peptides, nucleic acids or other bio- or macromolecules or fragments thereof. Preferably, antigens may be proteins and peptides or fragments thereof, such as epitopes of those proteins or peptides, preferably having 5 to 15, more preferably 6 to 9, amino acids. Particularly, said proteins, peptides or epitopes may be derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV), or from fragments, variants or derivatives thereof. Further, antigens may also comprise any other biomolecule, e.g., lipids, carbohydrates, etc. Preferably, the antigen is a protein or (poly-) peptide antigen, a nucleic acid, a nucleic acid encoding a protein or (poly-) peptide antigen, a polysaccharide antigen, a polysaccharide conjugate antigen, a lipid antigen, a glycolipid antigen, a carbohydrate antigen, a bacterium, a cell (vaccine), or killed or attenuated viruses.

The inventive pharmaceutical composition or vaccine as defined herein may furthermore comprise further additives or additional compounds. Further additives, which may be included in the pharmaceutical composition, are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives, RNase inhibitors and/or an anti-bacterial agent or an anti-viral agent. Additionally the inventive pharmaceutical composition may comprise small interfering RNA (siRNA) directed against genes of Respiratory syncytial virus (RSV), e.g. siRNA directed against the gene encoding the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV). The inventive pharmaceutical composition typically comprises a "safe and effective amount" of the components of the inventive pharmaceutical composition, particularly of the inventive mRNA sequence(s) as defined herein. As used herein, a "safe and effective amount" means an amount of the inventive mRNA sequence(s) as defined herein as such that is sufficient to significantly induce a positive modification of a disease or disorder or to prevent a disease, preferably RSV infections as defined herein. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general or as a vaccine.

According to another particularly preferred aspect, the inventive pharmaceutical composition (or the inventive mRNA sequence as defined herein or the inventive composition comprising a plurality of inventive mRNA sequences as defined herein) may be provided or used as a vaccine. Typically, such a vaccine is as defined above for pharmaceutical compositions. Additionally, such a vaccine typically contains the inventive mRNA sequence as defined herein or the inventive composition comprising a plurality of inventive mRNA sequences as defined herein.

The inventive vaccine may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form.

In a preferred embodiment, the inventive vaccine is administered via intradermal or intramuscular injection, preferably by using conventional needle-based injection technique or by using a needle-free system, e.g. jet injection. In a further preferred embodiment, the inventive vaccine may be administered by jet injection as defined herein. Preferably, the inventive vaccine is adminstered intramuscularly by jet injection. According to another embodiment, the vaccine is administered intradermally via jet injection.

In a preferred embodiment, the vaccine may be administered once, twice or three times, preferably by intradermal or intramuscular injection, preferably by jet injection. According to a certain embodiment, a single administration of the inventive vaccine, preferably via intradermal or intramuscular injection, preferably by using jet injection, is sufficient for eliciting an immune response against the at least one antigen encoded by the mRNA sequence according to the invention. In a preferred embodiment, the single administration of the vaccine elicits an immune response resulting in virus neutralisation. In this context, one single intradermal or intramuscular injection of the vaccine is particularly preferred. Preferably, further administrations of the vaccine may optionally be carried out in order to enhance and/or prolong the immune response.

The inventive vaccine can additionally contain one or more auxiliary substances in order to increase its immunogenicity or immunostimulatory capacity, if desired. Particularly preferred are adjuvants as auxiliary substances or additives as defined for the pharmaceutical composition.

In a further aspect, the invention is directed to a kit or kit of parts comprising the components of the inventive mRNA sequence, the inventive composition comprising a plurality of inventive mRNA sequences, the inventive pharmaceutical composition or vaccine and optionally technical instructions with information on the administration and dosage of the components.

Beside the components of the inventive mRNA sequence, the inventive composition comprising a plurality of inventive mRNA sequences, the inventive pharmaceutical composition or vaccine the kit may additionally contain a pharmaceutically acceptable vehicle, an adjuvant and at least one further component as defined herein, as well as means for administration and technical instructions. The components of the inventive mRNA sequence, the inventive composition comprising a plurality of inventive mRNA sequences, the inventive pharmaceutical composition or vaccine and e.g. the adjuvant may be provided in lyophilized form. In a preferred embodiment, prior to use of the kit for vaccination, the provided vehicle is than added to the lyophilized components in a predetermined amount as written e.g. in the provided technical instructions. By doing so the inventive mRNA sequence, the inventive composition comprising a plurality of inventive mRNA sequences, the inventive pharmaceutical composition or vaccine, according to the above described aspects of the invention is provided that can afterwards be used in a method as described above, also.

The present invention furthermore provides several applications and uses of the inventive mRNA sequence as defined herein, of the inventive composition comprising a plurality of inventive mRNA sequences as defined herein, of the inventive pharmaceutical composition, of the inventive vaccine, all comprising the inventive mRNA sequence as defined herein or of kits comprising same.

In a further aspect, the invention provides an mRNA sequence encoding at least one antigenic peptide or protein of Respiratory syncytial virus (RSV), or a fragment, variant or derivative thereof, and a composition, a pharmaceutical composition, a vaccine and a kit, all comprising the mRNA sequence for use in a method of prophylactic and/or therapeutic treatment of RSV infections. Consequently, in a further aspect, the present invention is directed to the first medical use of the inventive mRNA sequence, the inventive composition comprising a plurality of inventive mRNA sequences, the inventive pharmaceutical composition, the inventive vaccine, and the inventive kit as defined herein as a medicament. Particularly, the invention provides the use of an mRNA sequence encoding at least one antigenic peptide or protein of Respiratory syncytial virus (RSV), or a fragment, variant or derivative thereof as defined above for the preparation of a medicament.

According to another aspect, the present invention is directed to the second medical use of the mRNA sequence encoding at least one antigenic peptide or protein of Respiratory syncytial virus (RSV), or a fragment, variant or derivative thereof, as defined herein, optionally in form of a composition comprising a plurality of inventive mRNA sequences, a pharmaceutical composition or vaccine, kit or kit of parts, for the treatment of RSV infections as defined herein. Particularly, the mRNA sequence encoding at least one antigenic peptide or protein of Respiratory syncytial virus (RSV), or a fragment, variant or derivative thereof to be used in a method as said above is a mRNA sequence formulated together with a pharmaceutically acceptable vehicle and an optionally additional adjuvant and an optionally additional further component as defined above e.g. a further antigen or a RSV immune globuline. In this context particularly the (prophylactic) treatment of infants, the elderly and immunocompromised patients is preferred. And even more preferred is the (prophylactic) treatment of preterm infants and infants with chronic lung disease.

The inventive mRNA sequence may alternatively be provided such that it is administered for preventing or treating RSV infections by several doses, each dose containing the inventive mRNA sequence encoding at least one antigenic peptide or protein of RSV infections Respiratory syncytial virus (RSV), or a fragment, variant or derivative thereof, e.g. the first dose containing at least one mRNA encoding at least one antigenic peptide or protein derived from the fusion protein F (or fragments, variants or derivatives thereof) and the second dose containing at least one mRNA sequence encoding at least one antigenic peptide or protein derived from a different antigen of Respiratory syncytial virus (RSV), preferably from the nucleoprotein N (or fragments, variants or derivatives thereof), from the M2-1 protein or the glycoprotein G (or fragments, variants or derivatives thereof). By that embodiment, both doses are administered in a staggered way, i.e. subsequently, shortly one after the other, e.g. within less than 10 minutes, preferably less than 2 minutes, and at the same site of the body to achieve the same immunological effect as for administration of one single composition containing both, e.g. the mRNA encoding the fusion protein F and the mRNA encoding the nucleoprotein N.

According to a specific embodiment, the inventive mRNA sequence, or the inventive pharmaceutical composition or vaccine may be administered to the patient as a single dose. In certain embodiments, the inventive mRNA sequence or the inventive pharmaceutical composition or vaccine may be administered to a patient as a single dose followed by a second dose later and optionally even a third, fourth (or more) dose subsequent thereto etc. In accordance with this embodiment, booster inoculations with the inventive mRNA sequence or the inventive pharmaceutical composition or vaccine may be administered to a patient at specific time intervals, preferably as defined below, following the second (or third, fourth, etc.) inoculation. In this context, it is particularly preferred that several doses comprise the same mRNA sequence encoding the same antigenic peptide or protein of Respiratory syncytial virus (RSV), e.g. fusion protein F. In that embodiment the doses are given in a specific time period e.g. 20-30 days. For example for post-exposure prophylaxis at least 5 doses of the inventive mRNA sequence or inventive pharmaceutical composition or vaccine can be administered in 20-30 days.

In a preferred embodiment, inventive mRNA sequence, inventive pharmaceutical composition or vaccine is administered via intradermal or intramuscular injection, preferably by using conventional needle-based injection technique or by using a needle-free system, e.g. jet injection. In a further preferred embodiment, the inventive mRNA sequence, inventive pharmaceutical composition or vaccine may be administered by jet injection as defined herein. Preferably, the inventive mRNA sequence, inventive pharmaceutical composition or vaccine is adiminstered intramuscularly by jet injection. According to another embodiment, the inventive mRNA sequence, inventive pharmaceutical composition or vaccine is administered intradermally via jet injection.

In a preferred embodiment, the inventive mRNA sequence, inventive pharmaceutical composition or vaccine may be administered once, twice or three times, preferably by intradermal or intramuscular injection, preferably by jet injection. According to a certain embodiment, a single administration of the inventive mRNA sequence, inventive pharmaceutical composition or vaccine, preferably via intradermal or intramuscular injection, preferably by using jet injection, is sufficient for eliciting an immune response against the at least one antigen encoded by the mRNA sequence according to the invention. In a preferred embodiment, the single administration of the inventive mRNA sequence, inventive pharmaceutical composition or vaccine elicits an immune response resulting in virus neutralisation. In this context, one single intradermal or intramuscular injection of the inventive mRNA sequence, inventive pharmaceutical composition or vaccine is particularly preferred. Preferably, further administrations of the inventive mRNA sequence, inventive pharmaceutical composition or vaccine may optionally be carried out in order to enhance and/or prolong the immune response.

In certain embodiments, such booster inoculations with the inventive mRNA sequence or inventive pharmaceutical composition or vaccine may utilize an additional compound or component as defined for the inventive mRNA sequence or inventive pharmaceutical composition or vaccine as defined herein.

According to a further aspect, the present invention also provides a method for expression of an encoded antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) comprising the steps, e.g. a) providing the inventive mRNA sequence as defined herein or the inventive composition comprising a plurality of inventive mRNA sequences as defined herein, b) applying or administering the inventive mRNA sequence as defined herein or the inventive composition comprising a plurality of inventive mRNA sequences as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, e.g. in naked or complexed form or as a pharmaceutical composition or vaccine as described herein, preferably via transfection or by using any of the administration modes as described herein. The method may be carried out in vitro, in vivo or ex vivo. The method may furthermore be carried out in the context of the treatment of a specific disease, particularly in the treatment of infectious diseases, preferably RSV infections as defined herein.

In this context, in vitro is defined herein as transfection or transduction of the inventive mRNA as defined herein or of the inventive composition comprising a plurality of inventive mRNA sequences as defined herein into cells in culture outside of an organism; in vivo is defined herein as transfection or transduction of the inventive mRNA or of the inventive composition comprising a plurality of inventive mRNA sequences into cells by application of the inventive mRNA or of the inventive composition to the whole organism or individual and ex vivo is defined herein as transfection or transduction of the inventive mRNA or of the inventive composition comprising a plurality of inventive mRNA sequences into cells outside of an organism or individual and subsequent application of the transfected cells to the organism or individual.

Likewise, according to another aspect, the present invention also provides the use of the inventive mRNA sequence as defined herein or of the inventive composition comprising a plurality of inventive mRNA sequences as defined herein, preferably for diagnostic or therapeutic purposes, for expression of an encoded antigenic peptide or protein, e.g. by applying or administering the inventive mRNA sequence as defined herein or of the inventive composition comprising a plurality of inventive mRNA sequences as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, preferably in naked form or complexed form, or as a pharmaceutical composition or vaccine as described herein, preferably via transfection or by using any of the administration modes as described herein. The use may be carried out in vitro, in vivo or ex vivo. The use may furthermore be carried out in the context of the treatment of a specific disease, particularly in the treatment of RSV infections.

In a further aspect, the invention provides a method of treatment or prophlaxis of RSV infections comprising the steps:

a) providing the inventive mRNA sequence, the composition comprising a plurality of inventive mRNA sequences, the pharmaceutical composition or the kit or kit of parts comprising the inventive mRNA sequence as defined above;
b) applying or administering the mRNA sequence, the composition, the pharmaceutical composition or the kit or kit of parts to a tissue or an organism;
c) optionally administering RSV immune globuline.

Taken together, the invention provides in a certain aspect an mRNA sequence comprising a coding region encoding at least one antigenic peptide or protein of Respiratory syncytial virus (RSV). The inventive mRNA sequence is for use in a method of prophylactic and/or therapeutic treatment of infections caused by syncytial virus (RSV). Accordingly, the invention relates to an mRNA sequence as defined herein for use in a method of prophylactic and/or therapeutic treatment of RSV infections.

In the present invention, if not otherwise indicated, different features of alternatives and embodiments may be combined with each other, where suitable. Furthermore, the term "comprising" shall not be narrowly construed as being limited to "consisting of" only, if not specifically mentioned. Rather, in the context of the present invention, "consisting of" is an embodiment specifically contemplated by the inventors to fall under the scope of "comprising", wherever "comprising" is used herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF DESCRIPTION OF THE FIGURES

The figures shown in the following are merely illustrative and shall describe the present invention in a further way. These figures shall not be construed to limit the present invention thereto.

FIG. 1: G/C optimized mRNA sequence of R1691 coding for RSV-F protein of the RSV long strain (RSV-F long) as comprised in the RSV-F long mRNA vaccine (SEQ ID NO. 31).

FIG. 2: G/C optimized mRNA sequence of R2510 coding for RSV-F protein of the RSV long strain (RSV-F long) as comprised in the RSV-F long mRNA vaccine (SEQ ID NO. 32).

FIG. 3: G/C optimized mRNA sequence of R2821 coding for RSV-F del554-574 mutant protein of the RSV long strain (RSV-F long) (SEQ ID NO. 33).

FIG. 4: G/C optimized mRNA sequence of R2831 coding for RSV-N protein of the RSV long strain (RSV-F long) (SEQ ID NO. 34).

FIG. 5: G/C optimized mRNA sequence of R2833 coding for RSV-$M_{2-1}$ protein of the RSV long strain (RSV-F long) (SEQ ID NO. 35).

FIGS. 6A-C: show that the RSV-F long mRNA vaccine induces antibody titers against the RSV-F protein comparable to those against inactivated RSV.

Female BALB/c mice were intradermally (i.d.) injected with the RSV-F long mRNA vaccine (160 μg of R1691) or Ringer-Lactate (RiLa buffer) as buffer control. One group was intramuscularly (i.m.) injected with 10 μg of the inactivated RSV long vaccine. All animals received boost injections on days 21 and 35, blood samples were collected on day 49 for the determination of antibody titers of pooled sera as described in Example 2.

As can be seen, the RSV-F long mRNA vaccine induces anti-F protein antibodies of the IgG1 and IgG2a subclasses. Antibody titers are displayed in the graph (n=5 mice/group).

Figure 7:
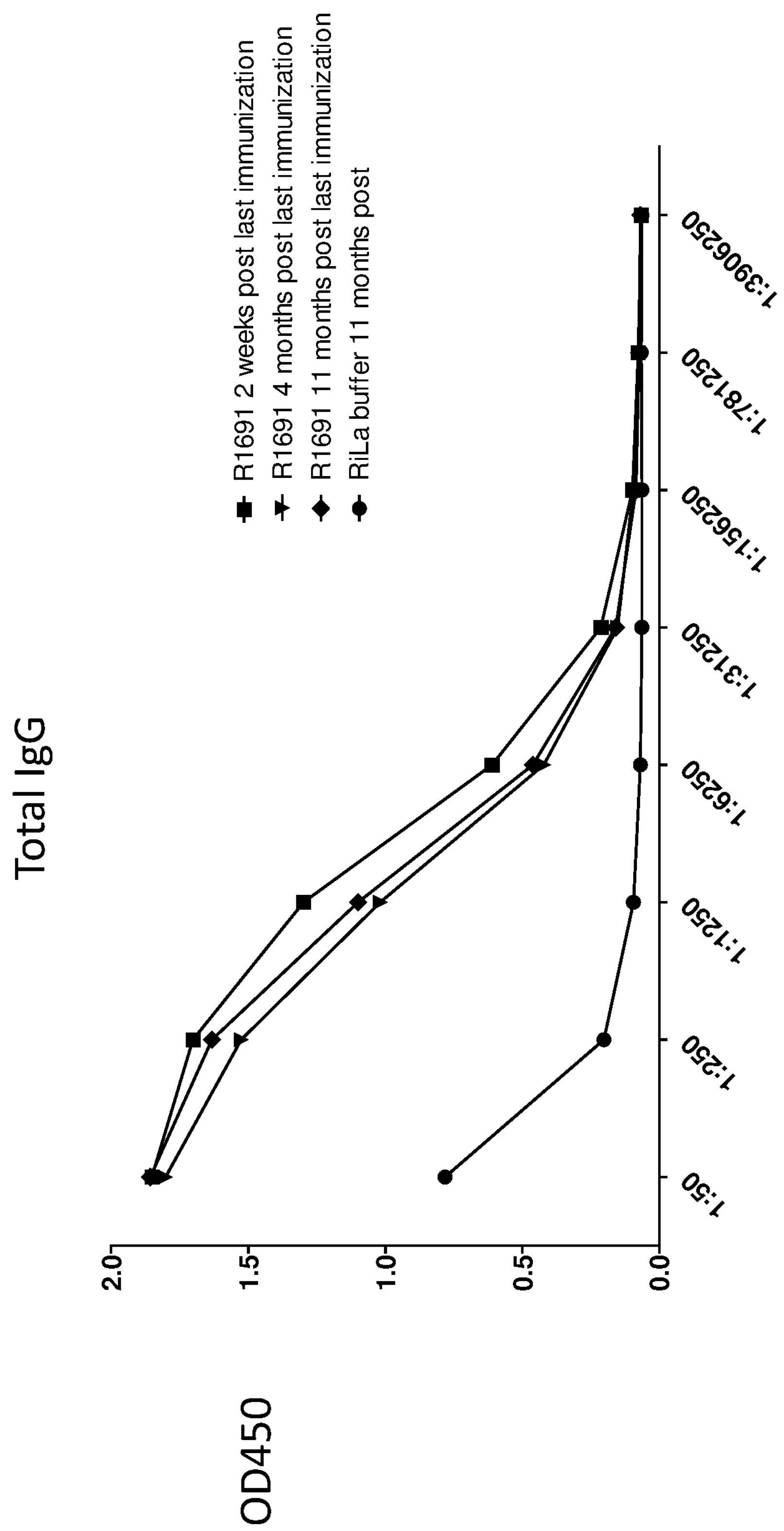

FIG. 7: shows that the RSV-F long mRNA vaccine (R1691) induces a long-lived immune response in mice.

The experiment was performed as described in Example 3 and antibody total IgG titers determined by ELISA.

As can be seen, the antibody titers are stable for at least eleven months after the last boost vaccination.

FIGS. 8A-D: show that the RSV-F long mRNA vaccine (R1691) induces RSV Fusion (F) protein-specific multifunctional $CD8^+$ T cells in mice.

The experiment was performed as described in Example 4 and T cells were analysed by intracellular cytokine staining for the antigen-specific induction of cytokines. Cells were stimulated with a RSV-F peptide (stim. F; KYKNAVTEL) or a control influenza HA peptide (stim. HA; IYSTVASSL). The line in the graph represents the median value (n=5 mice/group).

As can be seen, the RSV-F long mRNA vaccine induces RSV Fusion (F) protein-specific multifunctional $CD8^+$ T cells in contrast to the vaccine based on inactivated RSV which is not able to induce F protein-specific $CD8^+$ T cells.

Figure 9C:
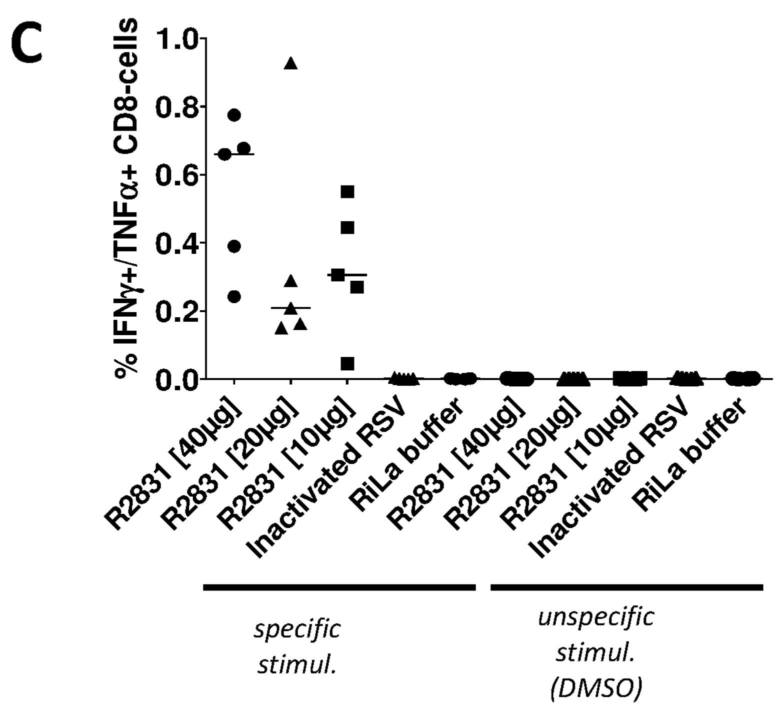

FIGS. 9A-C: show that the RSV-N mRNA vaccine (R2831) induces Nucleoprotein (N)-specific multifunctional $CD8^+$ T cells in mice.

The experiment was performed as described in Example 5 and T cells were analysed by intracellular cytokine staining for the antigen-specific induction of cytokines after stimulation with ProMix RSV-N (15 mer peptides). The line in the graph represents the median value (n=5 mice/group).

As can be seen, the RSV-N mRNA vaccine induces RSV Nucleoprotein (N)-specific multifunctional $CD8^+$ T cells in contrast to the vaccine based on inactivated RSV which is not able to induce N protein-specific $CD8^+$ T cells.

Figure 10C:
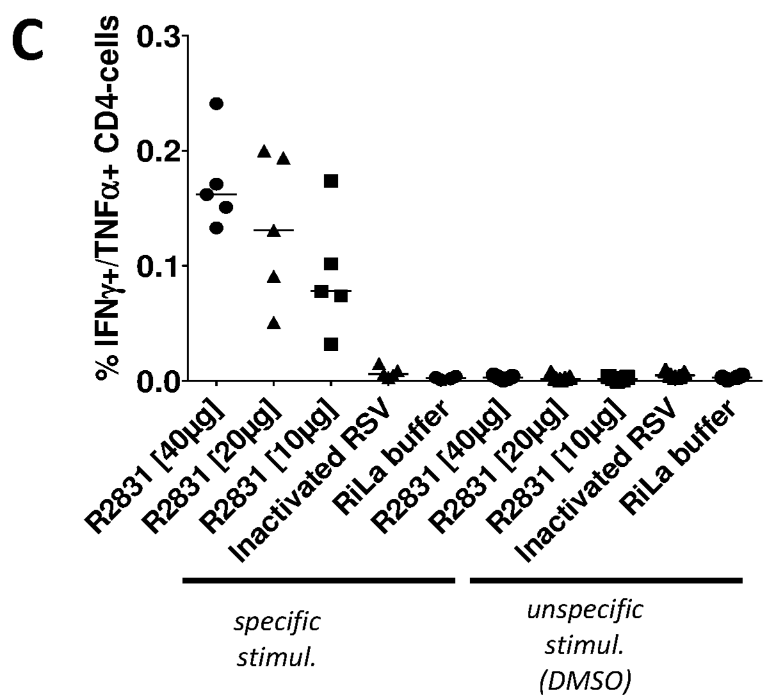

FIGS. 10A-C: show that the RSV-N mRNA vaccine (R2831) induces Nucleoprotein (N)-specific multifunctional $CD4^+$ T cells in mice.

The experiment was performed as described in Example 5 and T cells were analysed by intracellular cytokine staining for the antigen-specific induction of cytokines after stimulation with ProMix RSV-N (15 mer peptides). The line in the graph represents the median value (n=5 mice/group).

As can be seen, the RSV-N mRNA vaccine induces RSV Nucleoprotein (N)-specific multifunctional $CD4^+$ T cells in contrast to the vaccine based on inactivated RSV which is not able to induce N protein-specific $CD4^+$ T cells.

Figure 11C:
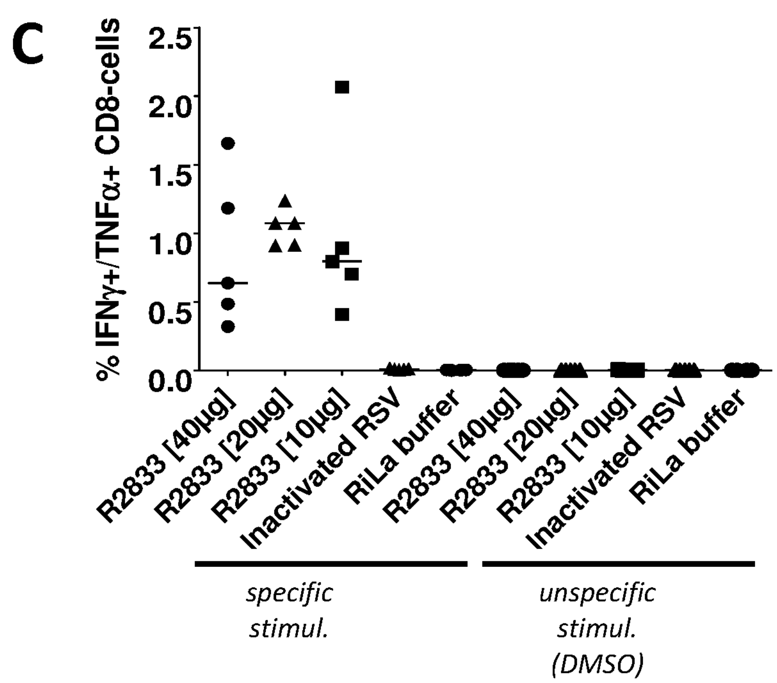

FIGS. 11A-C: show that the RSV-$M_{2-1}$ mRNA vaccine (R2833) induces $M_{2-1}$-specific multifunctional $CD8^+$ T cells in mice.

The experiment was performed as described in Example 5 and T cells were analysed by intracellular cytokine staining for the antigen-specific induction of cytokines after stimulation with a $M_{2-1}$ specific 9 mer peptide. The line in the graph represents the median value (n=5 mice/group).

As can be seen, the RSV-$M_{2-1}$ mRNA vaccine induces RSV RSV-$M_{2-1}$-specific multifunctional $CD8^+$ T cells in contrast to the vaccine based on inactivated RSV which is not able to induce $M_{2-1}$ protein-specific $CD8^+$ T cells.

Figure 12:
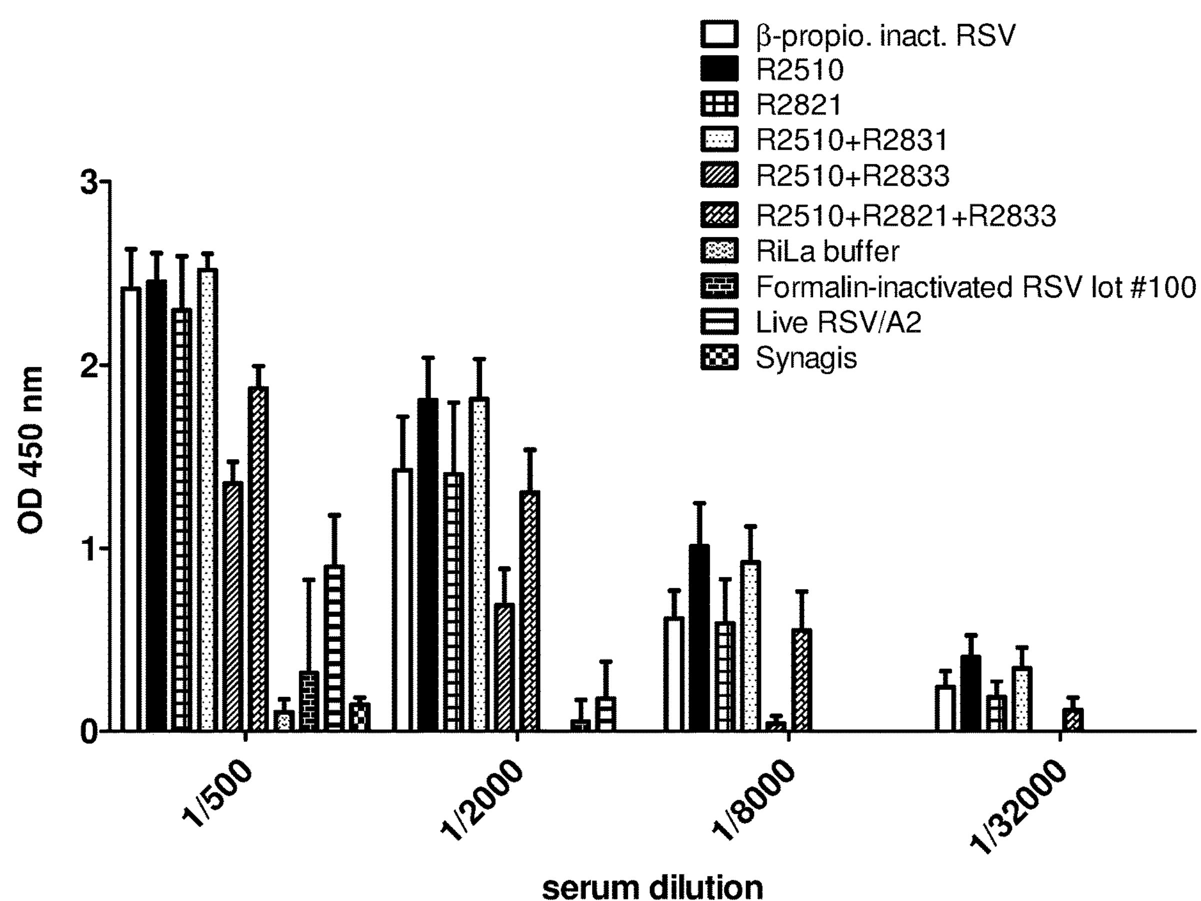

FIG. 12: shows that RSV-F mRNA vaccines either alone (RSV-F=R2510; RSV-Fdel554-574 mutant=R2821) or in combination with mRNAs encoding other RSV proteins (RSV-N=R2831; RSV-$M_{2-1}$=R2833) induce humoral immune responses in cotton rats.

The experiment was performed as described in Example 6 and RSV-F specific total IgG antibody titers were determined by ELISA on day 49. Serum was analyzed in different dilution, as given below the graph.

Figure 13:
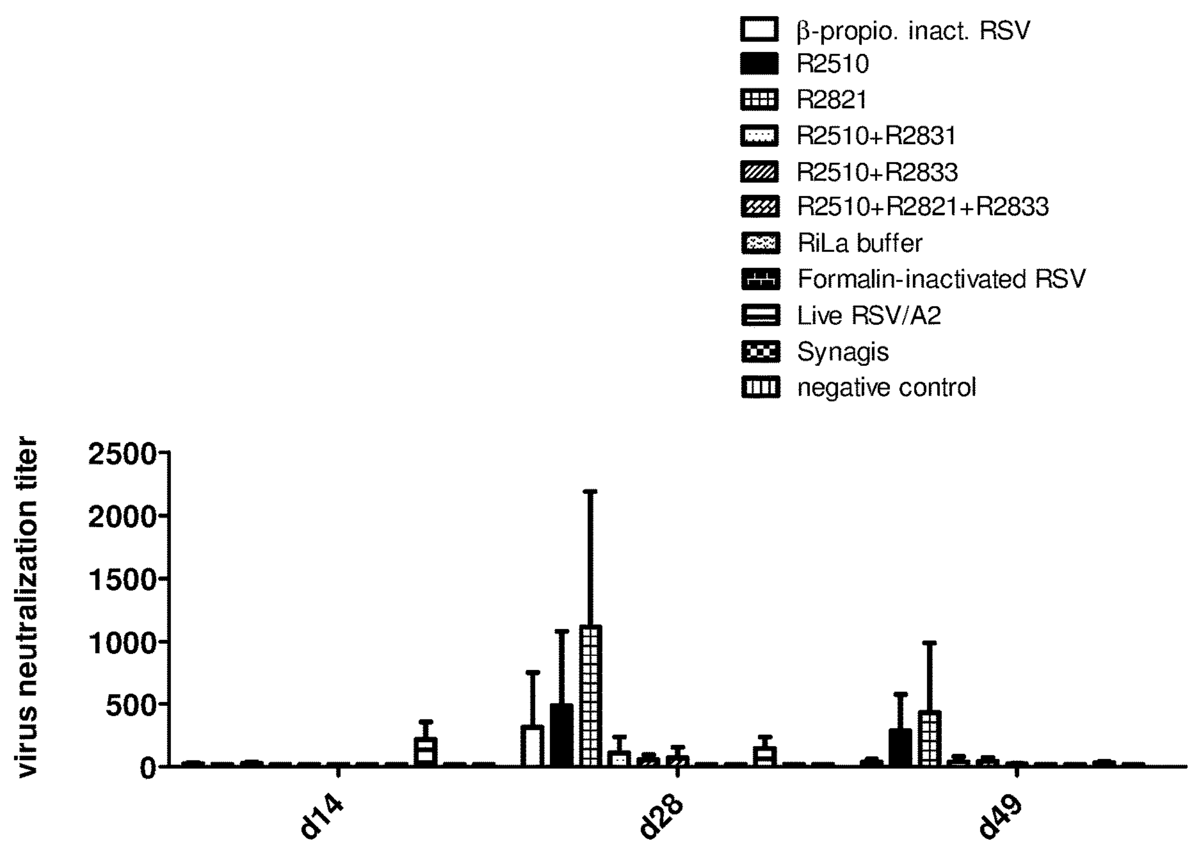

FIG. 13: shows that RSV-F mRNA vaccines either alone (RSV-F, R2510; RSV-Fdel554-574 mutant, R2821) or in combination with mRNAs encoding other RSV proteins (RSV-N=R2831; RSV-$M_{2-1}$=R2833) induce the formation of functional antibodies in cotton rats as shown by virus neutralizing antibody titers.

The experiment was performed as described in Example 6 and virus neutralizing titers on day 49 were determined by plaque reduction assay.

FIGS. 14A-B: show that RSV-F mRNA vaccines either alone (RSV-F=R2510; RSV-Fdel554-574 mutant=R2821) or in combination with mRNAs encoding other RSV proteins (RSV-N=R2831; RSV-$M_{2-1}$=R2833) reduce lung and nasal titers in cotton rats challenged with RSV virus.

The experiment was performed as described in Example 6.

(A) Lung titers on day 5 after RSV challenge infection. All animal groups vaccinated with mRNA vaccines showed virus titers below the level of detection of the performed virus titration demonstrating protection of vaccinated cotton rats in terms of viral lung titers. In comparison to the mRNA vaccines the vaccine based on formalin-inactivated virus were not able to prevent virus titers in the lung.

(B) Nasal titers on day 5 after RSV challenge infection. The viral titer in the nasal tissue was also strongly reduced in groups vaccinated with mRNA. In comparison to the mRNA vaccines the vaccine based on formalin-inactivated virus were not able to reduce the nasal virus titers.

Figure 15:
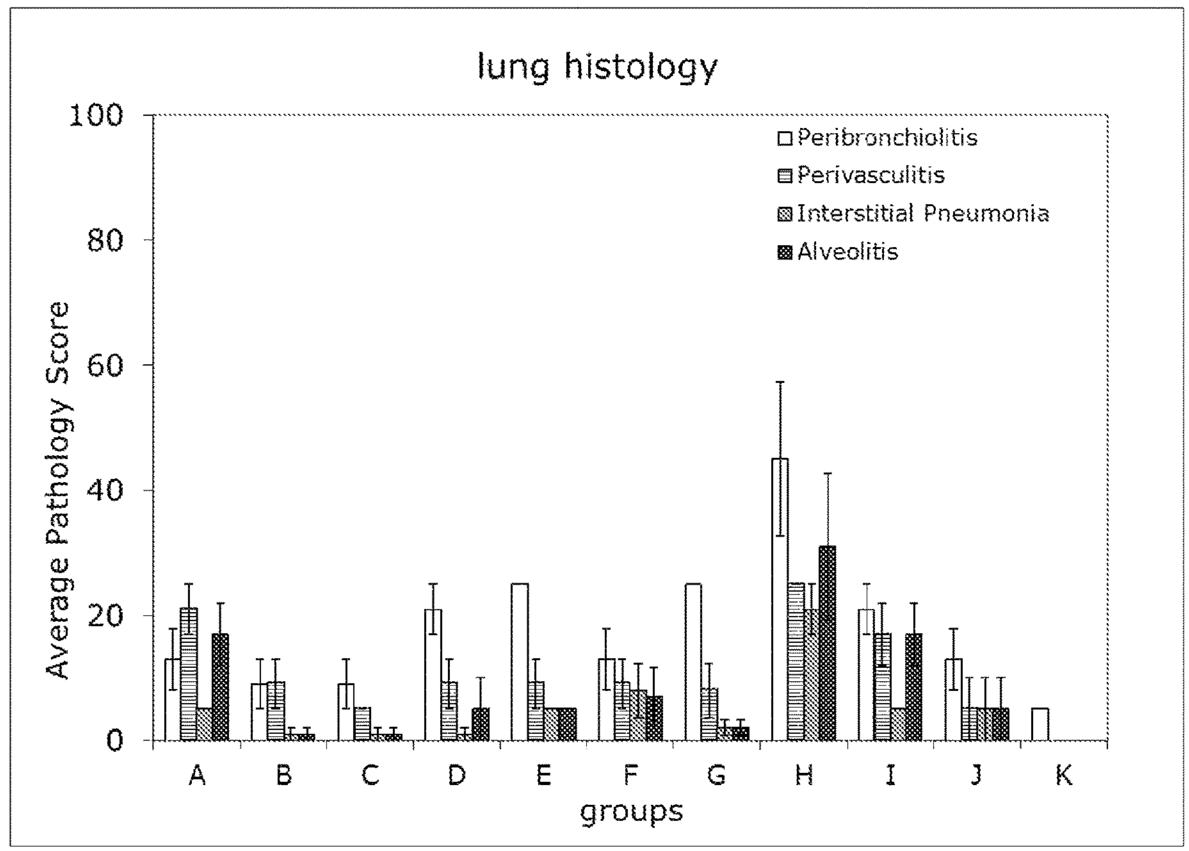

FIG. 15: shows the results of the lung histopathology analysis from the RSV cotton rat challenge study described in Example 6.

FIGS. 16A-D: show the results of the quantitative reverse transcription polymerase chain reaction (RT-PCR) of viral genome copy numbers (by measuring copy numbers of the RSV NS-1 gene) or expressed cytokines from lung tissue of the RSV infected animals (or controls) of the RSV cotton rat challenge study described in Example 6.

FIGS. 17A-B: show that RSV-F mRNA vaccines (RSV-F=R2510; RSV F* (RSV-Fdel554-574 mutant)=R2821) reduce lung titers in cotton rats challenged with RSV virus.

The experiment was performed as described in Example 7.

(A) Lung titers on day 5 after RSV challenge infection. All animal groups vaccinated intradermally with mRNA vaccines showed reduced virus titers compared to the buffer control group demonstrating protection of vaccinated cotton rats in terms of viral lung titers. Already one single dose of RSV-F mRNA vaccines efficiently reduced viral titers in the lung.

(B) Lung titers on day 5 after RSV challenge infection. The viral titer in the lung was also strongly reduced in groups intramuscularly vaccinated with mRNA.

EXAMPLES

The examples shown in the following are merely illustrative and shall describe the present invention in a further way. These examples shall not be construed to limit the present invention thereto.

Example 1: Preparation of the mRNA Vaccine

1. Preparation of DNA and mRNA Constructs

For the present examples DNA sequences, encoding the RSV-F protein (R1691 and R2510), the RSV-F del554-574 (R2821) mutant protein, the RSV N-protein (R2831) and the RSV M2-1 protein (R2833) of the RSV long strain were prepared and used for subsequent in vitro transcription reactions. The RSV-Fdel554-574 mutant protein has been described previously (Oomens et al. 2006. J. Virol. 80(21): 10465-77).

According to a first preparation, the DNA sequences coding for the above mentioned mRNAs were prepared. The construct R1691 was prepared by modifying the wild type coding sequence by introducing a GC-optimized sequence for stabilization, followed by a stabilizing sequence derived from the alpha-globin-3'-UTR (muag (mutated alpha-globin-3'-UTR) according to SEQ ID No. 29), a stretch of 64 adenosines (poly(A)-sequence), a stretch of 30 cytosines (poly(C)-sequence), and a histone stem loop according to SEQ ID No. 30. In SEQ ID NO: 31 (see FIG. 1) the sequence of the corresponding mRNA is shown. The constructs R2510, R2821, R2831 and R2833 were prepared by introducing a 5'-TOP-UTR derived from the ribosomal protein 32L according to SEQ ID No. 23, modifying the wild type coding sequence by introducing a GC-optimized sequence for stabilization, followed by a stabilizing sequence derived from the albumin-3'-UTR (albumin7 according to SEQ ID No. 25), a stretch of 64 adenosines (poly(A)-sequence), a stretch of 30 cytosines (poly(C)-sequence), and a histone stem loop according to SEQ ID No. 30. In SEQ ID NOs: 32-35 (see FIG. 2-5) the sequences of the corresponding mRNAs are shown.

TABLE 1

| mRNA constructs | | | |
|---|---|---|---|
| RNA | Antigen | Figure | SEQ ID NO. |
| R1691 | RSV F | 1 | SEQ ID NO. 31 |
| R2510 | RSV F | 2 | SEQ ID NO. 32 |
| R2821 | RSV Fdel554-574 | 3 | SEQ ID NO. 33 |
| R2831 | RSV N | 4 | SEQ ID NO. 34 |
| R2833 | RSV $M_{2-1}$ | 5 | SEQ ID NO. 35 |

2. In Vitro Transcription

The respective DNA plasmids prepared according to paragraph 1 were transcribed in vitro using T7 polymerase in the presence of a CAP analog ($m^7$GpppG). Subsequently the mRNA was purified using PureMessenger® (CureVac, Tubingen, Germany; WO2008/077592A1).

3. Reagents

Complexation Reagent: protamine

4. Preparation of the Vaccine

The mRNA was complexed with protamine by addition of protamine to the mRNA in the ratio (1:2) (w/w) (adjuvant component). After incubation for 10 minutes, the same amount of free mRNA used as antigen-providing RNA was added.

For example: RSV-F long vaccine (R1691): comprising an adjuvant component consisting of mRNA coding for RSV F protein long (R1691) according to SEQ ID NO. 31 complexed with protamine in a ratio of 2:1 (w/w) and the antigen-providing free mRNA coding for RSV F protein long (R1691) according to SEQ ID NO. 31 (ratio 1:1; complexed RNA:free RNA).

Example 2: Induction of a Humoral Immune Response by the RSV-F Long mRNA Vaccine in Mice Immunization On day zero, BALB/c mice were intradermally (i.d.) injected with the RSV-F long mRNA vaccine (R1691 according to Example 1; 25 μg/mouse/vaccination day) or Ringer-lactate (RiLa) as buffer control as shown in Table 2. A control group was intramuscularly (i.m.) injected with 10 μg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 μg/μL was achieved. All animals received boost injections on day 14 and day 28. Blood samples were collected on day 42 for the determination of anti-RSV F antibody titers.

TABLE 2

| Animal groups | | | | | |
|---|---|---|---|---|---|
| Group | Strain sex | No. mice | Route volume | Vaccine dose | Vaccination schedule |
| 1 | BALB/c Female | 5 | i.d. 2 × 50 μl | R1691 2 μg | d0: prime, d14: boost, d28: boost, d42: blood collection |
| 2 | BALB/c Female | 5 | i.m. 2 × 25 μl | Inactivated RSV long 10 μg | d0: prime, d14: boost, d28: boost, d42: blood collection |
| 3 | BALB/c Female | 5 | i.d. 2 × 50 μl | 80% Ringer Lactate (RiLa) buffer | d0: prime, d14: boost, d28: boost, d42: blood collection |

Determination of Anti-RSV F Protein Antibodies by ELISA

ELISA plates are coated with recombinant human RSV fusion glycoprotein (rec.hu F-protein, final conc.: 5 μg/mL) (Sino Biological Inc.). Coated plates are incubated using given serum dilutions and binding of specific antibodies to the F protein is detected using biotinylated isotype specific anti-mouse antibodies in combination with streptavidin-HRP (horse radish peroxidase) with ABTS substrate.

Results

Figure 6C:
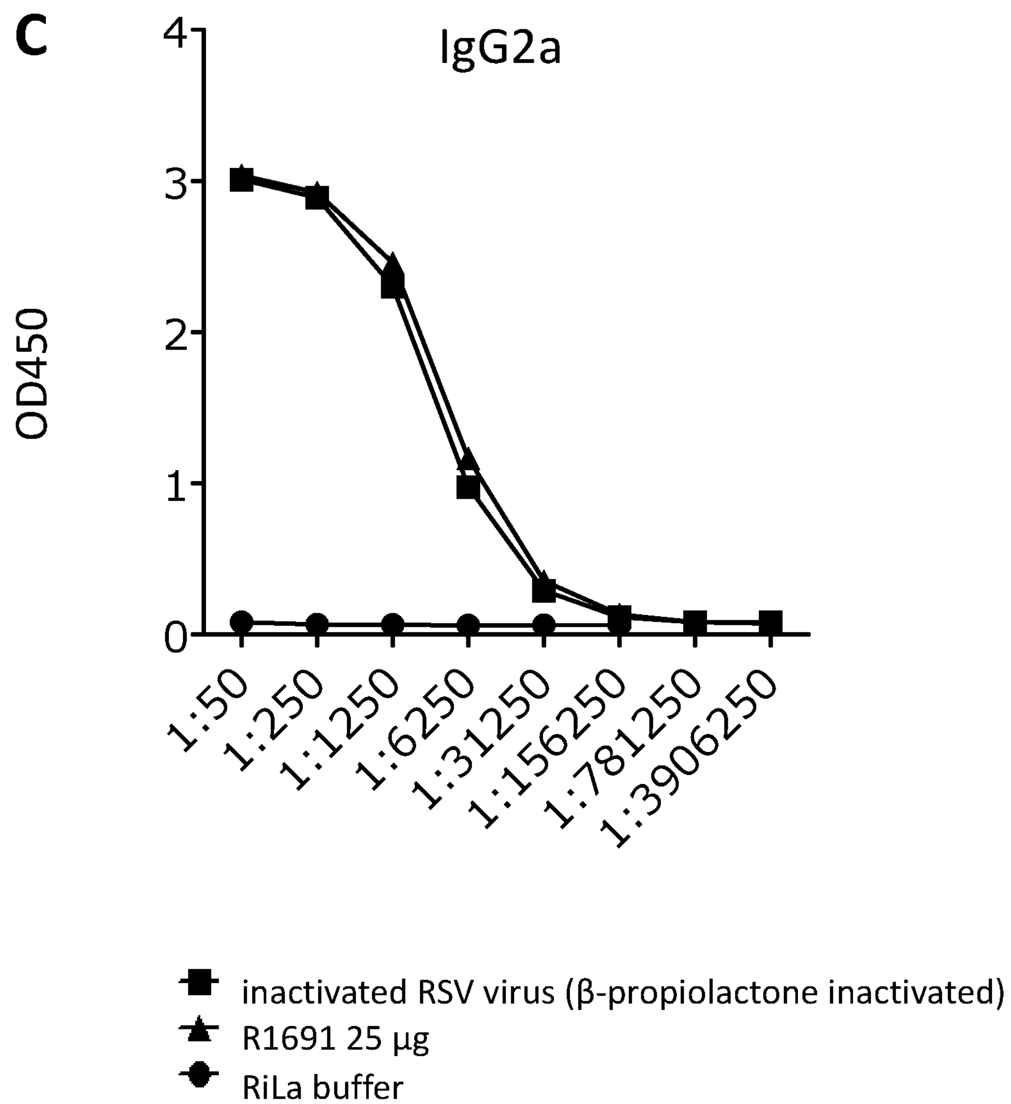

As can be seen in FIG. 6, the RSV-F long mRNA vaccine induces antibody titers (total IgG, IgG1 and IgG2a) against the RSV F protein comparable to those against inactivated RSV.

Example 3: Induction of a Long-Lived Humoral Immune Response by the RSV-F Long mRNA Vaccine in Mice Immunization BALB/c mice were intradermally (i.d.) injected with 20 μg of the RSV-F long mRNA vaccine (R1691) or Ringer Lactate (RiLa) buffer according to the vaccination schedule shown in Table 3. Blood was collected 2 weeks, 4 months and 11 months after the last immunization.

TABLE 3

| Animal groups | | | | | |
|---|---|---|---|---|---|
| Group | Strain sex | Number of mice | Route volume | Vaccine dose | Vaccination schedule (day) |
| 1 | BALB/c Female | 5 | i.d. 100 μl | R1691 20 μg | d0, d14, d28 |
| 4 | BALB/c Female | 5 | i.d. 100 μl | 80% RiLa buffer | d0, d14, d28 |

Results

As can be seen in FIG. 7, the RSV-F long mRNA vaccine induced a long-lived immune response as demonstrated by stable antibody titers for at least 11 months after the last boost vaccination.

Example 4: Induction of a Cellular Immune Response by the RSV-F Long mRNA Vaccine in Mice Immunization On day zero, BALB/c mice were intradermally (i.d.) injected with the RSV-F long mRNA vaccine R1691 (20 μg/mouse/vaccination day) or Ringer-lactate (RiLa) as buffer control as shown in Table 4. A control group was intramuscularly (i.m.) injected with 10 μg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 μg/μL was achieved.

All animals received boost injections on days 14 and 28. Spleens were collected on day 34 for the analysis of antigen-specific T cells.

TABLE 4

| Animal groups | | | | | |
|---|---|---|---|---|---|
| Group | Strain sex | Number of mice | Route volume | Vaccine dose | Vaccination schedule |
| 1 | BALB/c Female | 5 | i.d. 2 × 50 μl | R1691 20 μg | d0: prime, d14: boost, d28: boost, d34: spleen collection |
| 2 | BALB/c Female | 5 | i.m. 2 × 25 μl | Inactivated RSV long 10 μg | d0: prime, d14: boost, d28: boost, d34: spleen collection |
| 3 | BALB/c Female | 5 | i.d. 2 × 50 μl | Ringer Lactate (RiLa) buffer | d0: prime, d14: boost, d28: boost, d34: spleen collection |

Intracellular Cytokine Staining

Splenocytes from vaccinated and control mice were isolated according to a standard protocol. Briefly, isolated spleens were grinded through a cell strainer and washed in PBS/1% FBS followed by red blood cell lysis. After an extensive washing step with PBS/1% FBS splenocytes were seeded into 96-well plates ($2\times10^6$ cells/well). The next day cells were stimulated with a RSV-F peptide (KYKNAVTEL; 5 μg/ml; H-2kd-restructed T-cell epitope) or an irrelevant control peptide derived from the influenza HA protein (IYSTVASSL; 5 μg/ml; purchased from EMC Microcollections) and 2.5 μg/ml of an anti-CD28 antibody (BD Biosciences) for 6 hours at 37° C. in the presence of the mixture of GolgiPlug™/GolgiStop™ (Protein transport inhibitors containing Brefeldin A and Monensin, respectively; BD Biosciences). After stimulation cells were washed and stained for intracellular cytokines using the Cytofix/Cytoperm reagent (BD Biosciences) according to the manufacturer's instructions. The following antibodies were used for staining: CD8-PECy7 (1:200), CD3-FITC (1:200), IL2-PerCP-Cy5.5 (1:100), TNFα-PE (1:100), IFNγ-APC (1:100) (eBioscience), CD4-BD Horizon V450 (1:200) (BD Biosciences) and incubated with Fcγ-block diluted 1:100. Aqua Dye was used to distinguish live/dead cells (Invitrogen). Cells were collected using a Canto II flow cytometer (Beckton Dickinson). Flow cytometry data were analysed using FlowJo software (Tree Star, Inc.). Statistical analysis was performed using GraphPad Prism software, Version 5.01. Statistical differences between groups were assessed by the Mann Whitney test.

Results

As can be seen from FIG. 8, the RSV-F long mRNA vaccine (R1691) induced IFNγ positive, TNFα positive and IFNγ/TNFα double-positive multifunctional $CD8^+$ T cells directed against RSV F protein. Surprisingly the vaccine based on inactivated RSV virus was not able to induce antigen-specific $CD8^+$ T cells.

Example 5: Induction of Cellular Immune Responses by the RSV-N and RSV-M2-1 mRNA Vaccines in Mice Immunization On day zero, BALB/c mice were intradermally (i.d.) injected with different doses of the RSV-N mRNA vaccine R2831, the RSV-$M_{2-1}$ mRNA vaccine R2833 or Ringer-lactate (RiLa) as buffer control as shown in Table 5. A control group was intramuscularly (i.m.) injected with 10 μg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 μg/μL was achieved. All animals received boost injections on days 7 and 21. Spleens were collected on day 27 for the analysis of antigen-specific T cells.

TABLE 5

| Animal groups | | | | | |
|---|---|---|---|---|---|
| Group | Strain sex | No. mice | Route volume | Vaccine dose | Vaccination schedule |
| 1 | BALB/c Female | 5 | i.d. 1 × 50 μl | R2831 RSV-N 40 μg | d0: prime, d7: boost, d21: boost, d27: spleen collection |
| 2 | BALB/c Female | 5 | i.d. 1 × 25 μl | R2831 RSV-N 20 μg | d0: prime, d7: boost, d21: boost, d27: spleen collection |
| 3 | BALB/c Female | 5 | i.d. 1 × 12.5 μl | R2831 RSV-N 10 μg | d0: prime, d7: boost, d21: boost, d27: spleen collection |
| 4 | BALB/c Female | 5 | i.d. 1 × 50 μl | R2833 RSV-$M_{2-1}$ 40 μg | d0: prime, d7: boost, d21: boost, d27: spleen collection |
| 5 | BALB/c Female | 5 | i.d. 1 × 25 μl | R2833 RSV-$M_{2-1}$ 20 μg | d0: prime, d7: boost, d21: boost, d27: spleen collection |
| 6 | BALB/c Female | 5 | i.d. 1 × 12.5 μl | R2833 RSV-$M_{2-1}$ 10 μg | d0: prime, d7: boost, d21: boost, d27: spleen collection |
| 7 | BALB/c Female | 5 | i.m. 2 × 25 μl | Inactiv. RSV long 10 μg | d0: prime, d7: boost, d21: boost, d27: spleen collection |
| 8 | BALB/c Female | 5 | i.d. 1 × 50 μl | 100% RiLa buffer | d0: prime, d7: boost, d21: boost, d27: spleen collection |

Intracellular cytokine staining was performed as described in Example 4 except that cells were treated with the following stimulators at:

M2-1 peptide (5 μg/ml) group 4 to 8; (SYIGSINNI from Prolmmune); ProMix N (1 μg/ml) 1-3, group 7 and 8; (PX39 from Proimmune); control: medium+DMSO+anti-CD28, group 1-8 as descripted above.

Results

As can be seen from FIG. 9, the RSV-N mRNA vaccine (R2831) induced IFNγ positive, TNFα positive and IFNγ/TNFα double-positive multifunctional $CD8^+$ T cells directed against RSV N protein in mice.

Surprisingly the vaccine based on inactivated RSV virus was not able to induce antigen-specific $CD8^+$ T cells.

As can be seen from FIG. 10, the RSV-N mRNA vaccine (R2831) induced IFNγ positive, TNFα positive and IFNγ/TNFα double-positive multifunctional $CD4^+$ T cells directed against RSV N protein in mice.

Surprisingly the vaccine based on inactivated RSV virus was not able to induce antigen-specific $CD4^+$ T cells.

As can be seen from FIG. 11, the RSV-$M_{2-1}$ mRNA vaccine (R2833) induced IFNγ positive, TNFα positive and IFNγ/TNFα double-positive multifunctional $CD8^+$ T cells directed against RSV $M_{2-1}$ protein in mice.

Surprisingly the vaccine based on inactivated RSV virus was not able to induce antigen-specific $CD8^+$ T cells.

Example 6: RSV Cotton Rat Challenge Study I

For the development of RSV vaccines the cotton rat is an accepted animal model, especially for the challenge infection. Cotton rats respond to formalin-inactivated RSV virus vaccine preparations with enhanced lung pathology. This allows the evaluation of the safety of a vaccination in terms of enhanced disease phenomenon.

To broaden and optimize the RSV-specific immune response, mRNA vaccines encoding different RSV proteins (RSV F, mutant RSV-Fdel554-574, N and $M_{2-1}$) were prepared according to Example 1. In order to assess the effect of single or combined vaccines, these vaccines were administered either alone or in combination (cocktail vaccine) as shown in Table 5. Vaccine volumes of 2×50 μl were injected intradermally (i.d.) into the back skin of cotton rats. Additional groups were immunized intramuscularly (i.m.) with β-propiolactone inactivated RSV (INSTITUT VIRION/SERION GmbH-SERION IMMUNDIAGNOSTICA GmbH), formalin-inactivated RSV (Sigmovir) or live RSV/A2 (Sigmovir) ($10^5$ plaque forming units, pfu) to compare their immunogenicity to mRNA vaccines. Another group received i.m. injections of the monoclonal anti-RSV antibody SYNAGIS® (Palivizumab) as passive immunization. SYNAGIS® was administered with a dose of 15 mg/kg on the day prior to RSV challenge infection. Therefore the animals were weighed and the appropriate amount of SYNAGIS® was calculated according to the animals' weight. The maximal volume for i.m. injection was 200 μl per 100 g rat. After immunization the cotton rats were challenged by intranasal (i.n.) infection with RSV/A2 virus ($10^5$ PFU in 100 μl; Sigmovir).

TABLE 5

| Animal groups | | | | | | | | |
|---|---|---|---|---|---|---|---|---|
| Groups | Vaccine dose | Volume | Antigen | Route | # of administrations | N per group | Vaccination (day) | Bleed (day) |
| A | β-propiolactone inactivated RSV 20 μg | 100 μl | — | IM | 3 | 5 | 0, 14, 28 | 14, 28, 49 |
| B | R2510 80 μg | 2 × 50 μl | RSV F | ID | 3 | 5 | 0, 14, 28 | 14, 28, 49 |
| C | R2821 80 μg | 2 × 50 μl | RSV F mutant | ID | 3 | 5 | 0, 14, 28 | 14, 28, 49 |
| D | R2510 + R2831 "cocktail I" each 40 μg | 2 × 50 μl | RSV F + RSV N | ID | 3 | 5 | 0, 14, 28 | 14, 28, 49 |

TABLE 5-continued

| Animal groups | | | | | | | | |
|---|---|---|---|---|---|---|---|---|
| Groups | Vaccine dose | Volume | Antigen | Route | # of administrations | N per group | Vaccination (day) | Bleed (day) |
| E | R2510 + R2833 "cocktail II" each 40 μg | 2 × 50 μl | RSV F+ RSV $M_{2-1}$ | ID | 3 | 5 | 0, 14, 28 | 14, 28, 49 |
| F | R2510 + R2831 + R2833 "cocktail III" each 26.666 μg | 2 × 50 μl | RSV F + RSV $M_{2-1}$ + RSV N | ID | 3 | 5 | 0, 14, 28 | 14, 28, 49 |
| G | RiLa | 2 × 50 μl | — | ID | 3 | 5 | 0, 14, 28 | 14, 28, 49 |
| H | FI-RSV Lot#100 (diluted 1:100 in PBS) | 100 μl | — | IM | 2 | 5 | 0, 28 | 28, 49 |
| I | Live RSV/A2 $10^5$ pfu | 100 μl | — | IM | 1 | 5 | 0 | 49 |
| J | SYNAGIS ® (15 mg/kg) | | — | IM | 1 | 5 | 48 | 49 |
| K | Neg. control | | — | N/A | N/A | 5 | — | — |

The following assays were performed to analyze the immune responses: RSV F-protein serum IgG ELISA, RSV virus neutralizing antibody titers (VNT), RSV viral titrations and pulmonary histopathology.

RSV F-Protein Serum IgG ELISA

The induction of anti-RSV F protein antibodies were determined by ELISA according to Example 2.

RSV Virus Neutralizing Antibody Titers (VNT)

Sera were analysed by the virus neutralization test (VNT). Briefly, sera samples were diluted 1:10 with EMEM, heat inactivated and serially diluted further 1:4. Diluted sera samples were incubated with RSV (25-50 PFU) for 1 hour at room temperature and inoculated in duplicates onto confluent HEp-2 monolayers in 24 well plates. After one hour incubation at 37° C. in a 5% $CO_2$ incubator, the wells were overlayed with 0.75% Methylcellulose medium. After 4 days of incubation, the overlay was removed and the cells were fixed with 0.1% crystal violet stain for one hour and then rinsed and air dried. The corresponding reciprocal neutralizing antibody titers were determined at the 60% reduction end-point of the virus control.

RSV Viral Titrations and Pulmonary Histopathology

On day 54 nasal tissue was harvested and homogenized for viral titrations. The lung was harvested en bloc and tri-sected for viral titration (left section), histopathology (right section), and PCR analysis (lingular lobe). In addition, RSV viral genome copy numbers (by measuring copy numbers of the RSV NS-1 gene) and cytokine mRNA levels were determined by quantitative reverse transcription polymerase chain reaction (qRT-PCR).

Results

As can be seen from FIG. 12, the RSV-F mRNA vaccines either alone (RSV-F=R2510; RSV-Fdel554-574 mutant=R2821) or in combination with mRNAs encoding other RSV proteins (RSV-N=R2831; RSV-M2-1=R2833), induce RSV F specific humoral immune responses in cotton rats as shown by total IgG antibody titers on day 49.

As can be seen from FIG. 13, the RSV-F mRNA vaccines either alone (RSV-F=R2510; RSV-Fdel554-574 mutant=R2821) or in combination with mRNAs encoding other RSV proteins (RSV-N, R2831=RSV-M2-1=R2833), induce the formation of RSV specific functional antibodies in cotton rats as shown by virus neutralizing antibody titers.

As can be seen from FIG. 14, the RSV-F mRNA vaccines either alone (RSV-F=R2510; RSV-Fdel554-574 mutant=R2821) or in combination with mRNAs encoding other RSV proteins (RSV-N=R2831; RSV-M2-1=R2833), reduce lung and nasal viral titers in cotton rats challenged with RSV virus.

As can be seen in FIG. 14A, all animal groups vaccinated with mRNA vaccines showed virus titers below the level of detection of the performed virus titration demonstrating protection of vaccinated cotton rats in terms of viral lung titers. By contrast, the Formalin-inactivated virus vaccine reduced only minimally the lung virus titer compared to the RiLa buffer control group. The effect of the β-propiolactone inactivated RSV vaccine was more pronounced but did not reduce the virus lung titer below the detection level in all animals of this group. As can be seen in FIG. 14B, the viral titer in the nasal tissue was also strongly reduced in groups vaccinated with mRNA. Nasal viral titers of the Formalin-inactivated virus were comparable to the viral titer in the RiLa vaccinated group. The β-propiolactone inactivated virus vaccine was more effective (at least for two of five animals). In contrast thereto, all mRNA vaccinated groups had reduced nasal virus titer compared to RiLa vaccinated group.

As can be seen from FIG. 15, the lung histopathology analysis from the RSV cotton rat challenge study reveals different pathology scores for the various animal groups. From the histopathology it can be concluded that none of the mRNA vaccinated groups displayed enhanced lung pathology as it is the case for the group that was vaccinated using the Formalin-inactivated RSV vaccine. The average pathology scores for peribronchiolitis (PB), perivasculitis (PV), insterstitial pneumonia (IP) and alveolitis (A) are much lower for all groups vaccinated with mRNA compared to group H (Formalin-inactivated RSV). In addition the groups being vaccinated with R2510 (group B; RSV F) or R2821 (group C; RSV F mutant) seem to exhibit reduced lung pathology compared to the RiLa buffer vaccinated and subsequently RSV infected group (G).

As can be seen in FIG. 16, the quantitative RT-PCR reveals different expression patterns for the various animal groups. The quantification of RSV genome copies by measuring the RSV NS-1 gene is displayed in A. Genome copy numbers are reduced by vaccination using mRNA vaccines compared to the RiLa buffer control (group G). This is not the case for the group that was vaccinated using formalin-inactivated-RSV (group H). As it is shown in B, the vaccination using the formalin-inactivated-RSV vaccine (group H) induces enhanced expression of the TH2 cytokine IL-4 compared to the control group that was vaccinated with RiLa buffer (group G). By contrast, the vaccination with mRNA R2821 encoding the RSV-F mutant significantly reduced IL-4 mRNA expression compared to the RiLa control group in the lung after RSV challenge infection. C. Expression of INF-γ□mRNA. D. Expression of IL-5 mRNA. The expression of IL-5 is significant reduced in groups vaccinated using R2510 or R2821 compared to RiLa buffer vaccinated animals. The expression of the viral NS-1 RNA or cytokine mRNAs, which were isolated from lung tissue, is measured on day 5 post-challenge. The statistical analysis was performed with the student T-test (*p<0.05 when compared to group G (RiLa control)).

Example 7: RSV Cotton Rat Challenge Study II mRNA vaccines encoding RSV F protein (F) or mutant RSV-F protein (F*) (RSV F del554-574) were prepared according to Example 1. In order to assess the effect of single or several vaccinations (prime and boost vaccinations), these vaccines were administered once, twice or 3 times (as shown in Table 6). Vaccine volumes of 2×50 μl were injected intradermally (i.d.) into the back skin of cotton rats. Additional groups were immunized intramuscularly (i.m.) with vaccine volumes of 1×100 μl into the right hind leg. As a control, one group was injected intradermally with Ringer-Lactate buffer (buffer). After immunization, the cotton rats were challenged by intranasal (i.n.) infection with RSV/A2 virus ($10^5$ PFU in 100 μl; Sigmovir). As a control, one group was not treated and remained unchallenged with virus (untreated).

TABLE 5

| Animal groups | | | | | | | | |
|---|---|---|---|---|---|---|---|---|
| Groups | Vaccine dose | Volume | Antigen | Route | # of administrations | N per group | Vaccination (day) | Challenge (day) |
| F* i.d. 3x | R2821 80 μg | 2 × 50 μl | RSV F mutant | ID | 3 | 5 | 0, 14, 28 | 49 |
| F* i.d. 2x | R2821 80 μg | 2 × 50 μl | RSV F mutant | ID | 2 | 5 | 0, 14 | 49 |
| F* i.d. 1x | R2821 80 μg | 2 × 50 μl | RSV F mutant | ID | 1 | 5 | 0 | 49 |
| F i.d. 3x | R2510 80 μg | 2 × 50 μl | RSV F | ID | 3 | 5 | 0, 14, 28 | 49 |
| F i.d. 2x | R2510 80 μg | 2 × 50 μl | RSV F | ID | 2 | 5 | 0, 14 | 49 |
| F i.d. 1x | R2510 80 μg | 2 × 50 μl | RSV F | ID | 1 | 5 | 0 | 49 |
| F* i.m. | R2821 80 μg | 1 × 100 μl | RSV F mutant | IM | 2 | 5 | 0, 14 | 49 |
| F i.m. | R2510 80 μg | 1 × 100 μl | RSV F | IM | 2 | 5 | 0, 14 | 49 |
| Buffer | — | 2 × 50 μl | | ID | 3 | 5 | 0, 14, 28 | 49 |
| untreated | — | | — | N/A | N/A | 5 | — | — |

RSV Viral Titrations

The determination of RSV viral titers was conducted as described in Example 6.

Results

As shown in FIG. 17A, already one single intradermal vaccination with mRNA vaccines coding for RSV F protein (F) or mutant RSV-F protein (F*) (RSV F del554-574) was highly efficient in reducing the viral titer in the lung compared to the buffer control group. A second and third vaccination ("boost vaccinations) reduced the viral titers below detection level.

As shown in FIG. 17B, already two intramuscular vaccinations with mRNA vaccines coding for RSV F protein (F) or mutant RSV-F protein (F*) (RSV F del554-574) strongly reduced the viral titer in the lung compared to the buffer control group.

The invention claimed is:

1. A method of stimulating an immune response to Respiratory syncytial virus (RSV) in a subject comprising administering to the subject a pharmaceutical composition comprising an mRNA molecule having a coding sequence encoding a fusion (F) protein of RSV with a deleted C-terminus (F-del) lacking amino acids 554-574 of native RSV-F, said coding sequence being at least 80% identical to the protein coding portion of the sequence of SEQ ID NO: 33, wherein the mRNA comprises from 5' to 3': (i) a 5'-cap structure; (ii) a 5' untranslated region (UTR); (iii) the coding sequence encoding the F protein; (iv) a 3' UTR; and (v) a poly(A) sequence, wherein the mRNA molecule is complexed with a cationic or polycationic compound.

2. The method of claim 1, wherein the mRNA further comprises a poly(C) sequence.

3. The method of claim 1, wherein the 5'-cap structure is m7GpppN.

4. The method of claim 1, wherein the poly(A) sequence comprises a sequence of 25 to 400 adenosine nucleotides.

5. The method of claim 1, wherein the mRNA further comprises at least one histone stem-loop.

6. The method of claim 1, wherein the mRNA sequence comprises a stabilizing sequence from the alpha globin 3' UTR, positioned 3' relative to the coding sequence of the mRNA sequence.

7. The method of claim 3, wherein the poly(A) sequence comprises 60 to 250 adenosine nucleotides.

8. The method of claim 1, wherein the mRNA further comprises at least one histone stem-loop.

9. The method of claim 7, wherein the cationic or polycationic compound comprises a cationic lipid.

10. The method of claim 1, wherein the composition comprises at least a second different mRNA encoding the second antigenic polypeptide from RSV.

11. The method of claim 1, wherein the at least second different mRNA encodes an antigen from a different virus or an antigenic fragment thereof.

12. The method of claim 7, wherein the 5'-cap structure is a Cap1 structure.

13. The method of claim 1, wherein the poly(A) sequence is at the 3' end of the mRNA molecule.

14. The method of claim 1, wherein the pharmaceutical composition is administered by intradermal or intramuscular injection.

15. The method of claim 14, wherein the pharmaceutical composition is administered by intramuscular injection.

* * * * *

SEQUENCE LISTING

<160> NUMBER OF SEQ ID NOS: 37

<210> SEQ ID NO 1
<211> LENGTH: 574
<212> TYPE: PRT
<213> ORGANISM: respiratory syncytial virus

<400> SEQUENCE: 1

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Asn
65                  70                  75                  80

Gln Glu Leu Asp Lys Tyr Lys Asn Ala Val Thr Glu Leu Gln Leu Leu
                85                  90                  95

Met Gln Ser Thr Thr Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His His Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 2
<211> LENGTH: 298
<212> TYPE: PRT
<213> ORGANISM: respiratory syncytial virus

<400> SEQUENCE: 2

Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Thr Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175
```

```
Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295


<210> SEQ ID NO 3
<211> LENGTH: 64
<212> TYPE: PRT
<213> ORGANISM: respiratory syncytial virus

<400> SEQUENCE: 3

Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Leu Ile
            20                  25                  30

Ile Ile Ser Ile Met Thr Ala Ile Leu Asn Lys Leu Cys Glu Tyr Asn
        35                  40                  45

Val Phe His Asn Lys Thr Phe Glu Leu Pro Arg Ala Arg Val Asn Thr
    50                  55                  60


<210> SEQ ID NO 4
<211> LENGTH: 256
<212> TYPE: PRT
<213> ORGANISM: respiratory syncytial virus

<400> SEQUENCE: 4

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Leu
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140
```

```
Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255


<210> SEQ ID NO 5
<211> LENGTH: 391
<212> TYPE: PRT
<213> ORGANISM: respiratory syncytial virus

<400> SEQUENCE: 5

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys His Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
```

```
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu
385                 390


<210> SEQ ID NO 6
<211> LENGTH: 2165
<212> TYPE: PRT
<213> ORGANISM: respiratory syncytial virus

<400> SEQUENCE: 6

Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Leu Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Ile Leu Ile Asp Asn Gln Thr Leu Ser
225                 230                 235                 240
```

```
Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Val Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
```

```
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750

Ile Arg Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Val Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910

Gln Glu Leu Glu Tyr Arg Gly Glu Ser Leu Leu Cys Ser Leu Ile Phe
        915                 920                 925

Arg Asn Val Trp Leu Tyr Asn Gln Ile Ala Leu Gln Leu Lys Asn His
    930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
            980                 985                 990

Leu Tyr Arg Ser Phe Tyr Arg Arg  Thr Pro Asp Phe Leu  Thr Glu Ala
        995                 1000                 1005

Ile Val  His Ser Val Phe Ile  Leu Ser Tyr Tyr Thr  Asn His Asp
    1010                 1015                 1020

Leu Lys  Asp Lys Leu Gln Asp  Leu Ser Asp Asp Arg  Leu Asn Lys
    1025                 1030                 1035

Phe Leu  Thr Cys Ile Ile Thr  Phe Asp Lys Asn Pro  Asn Ala Glu
    1040                 1045                 1050

Phe Val  Thr Leu Met Arg Asp  Pro Gln Ala Leu Gly  Ser Glu Arg
    1055                 1060                 1065

Gln Ala  Lys Ile Thr Ser Glu  Ile Asn Arg Leu Ala  Val Thr Glu
    1070                 1075                 1080
```

```
Val Leu  Ser Thr Ala Pro Asn  Lys Ile Phe Ser Lys  Ser Ala Gln
    1085                 1090                 1095

His Tyr  Thr Thr Thr Glu Ile  Asp Leu Asn Asp Ile  Met Gln Asn
    1100                 1105                 1110

Ile Glu  Pro Thr Tyr Pro His  Gly Leu Arg Val Val  Tyr Glu Ser
    1115                 1120                 1125

Leu Pro  Phe Tyr Lys Ala Glu  Lys Ile Val Asn Leu  Ile Ser Gly
    1130                 1135                 1140

Thr Lys  Ser Ile Thr Asn Ile  Leu Glu Lys Thr Ser  Ala Ile Asp
    1145                 1150                 1155

Leu Thr  Asp Ile Asp Arg Ala  Thr Glu Met Met Arg  Lys Asn Ile
    1160                 1165                 1170

Thr Leu  Leu Ile Arg Ile Leu  Pro Leu Asp Cys Asn  Arg Asp Lys
    1175                 1180                 1185

Arg Glu  Ile Leu Ser Met Glu  Asn Leu Ser Ile Thr  Glu Leu Ser
    1190                 1195                 1200

Lys Tyr  Val Arg Glu Arg Ser  Trp Ser Leu Ser Asn  Ile Val Gly
    1205                 1210                 1215

Val Thr  Ser Pro Ser Ile Met  Tyr Thr Met Asp Ile  Lys Tyr Thr
    1220                 1225                 1230

Thr Ser  Thr Ile Ala Ser Gly  Ile Ile Ile Glu Lys  Tyr Asn Val
    1235                 1240                 1245

Asn Ser  Leu Thr Arg Gly Glu  Arg Gly Pro Thr Lys  Pro Trp Val
    1250                 1255                 1260

Gly Ser  Ser Thr Gln Glu Lys  Lys Thr Met Pro Val  Tyr Asn Arg
    1265                 1270                 1275

Gln Val  Leu Thr Lys Lys Gln  Arg Asp Gln Ile Asp  Leu Leu Ala
    1280                 1285                 1290

Lys Leu  Asp Trp Val Tyr Ala  Ser Ile Asp Asn Lys  Asp Glu Phe
    1295                 1300                 1305

Met Glu  Glu Leu Ser Ile Gly  Thr Leu Gly Leu Thr  Tyr Glu Lys
    1310                 1315                 1320

Ala Lys  Lys Leu Phe Pro Gln  Tyr Leu Ser Val Asn  Tyr Leu His
    1325                 1330                 1335

Arg Leu  Thr Val Ser Ser Arg  Pro Cys Glu Phe Pro  Ala Ser Ile
    1340                 1345                 1350

Pro Ala  Tyr Arg Thr Thr Asn  Tyr His Phe Asp Thr  Ser Pro Ile
    1355                 1360                 1365

Asn Arg  Ile Leu Thr Glu Lys  Tyr Gly Asp Glu Asp  Ile Asp Ile
    1370                 1375                 1380

Val Phe  Gln Asn Cys Ile Ser  Phe Gly Leu Ser Leu  Met Ser Val
    1385                 1390                 1395

Val Glu  Gln Phe Thr Asn Val  Cys Pro Asn Arg Ile  Ile Leu Ile
    1400                 1405                 1410

Pro Lys  Leu Asn Glu Ile His  Leu Met Lys Pro Pro  Ile Phe Thr
    1415                 1420                 1425

Gly Asp  Val Asp Ile His Lys  Leu Lys Gln Val Ile  Gln Lys Gln
    1430                 1435                 1440

His Met  Phe Leu Pro Asp Lys  Ile Ser Leu Thr Gln  Tyr Val Glu
    1445                 1450                 1455

Leu Phe  Leu Ser Asn Lys Thr  Leu Lys Ser Gly Ser  His Val Asn
    1460                 1465                 1470
```

```
Ser Asn  Leu Ile Leu Ala His  Lys Ile Ser Asp Tyr  Phe His Asn
    1475                 1480                 1485

Thr Tyr  Ile Leu Ser Thr Asn  Leu Ala Gly His Trp  Ile Leu Ile
    1490                 1495                 1500

Ile Gln  Leu Met Lys Asp Ser  Lys Gly Ile Phe Glu  Lys Asp Trp
    1505                 1510                 1515

Gly Glu  Gly Tyr Ile Thr Asp  His Met Phe Ile Asn  Leu Lys Val
    1520                 1525                 1530

Phe Phe  Asn Ala Tyr Lys Thr  Tyr Leu Leu Cys Phe  His Lys Gly
    1535                 1540                 1545

Tyr Gly  Lys Ala Lys Leu Glu  Cys Asp Met Asn Thr  Ser Asp Leu
    1550                 1555                 1560

Leu Cys  Val Leu Glu Leu Ile  Asp Ser Ser Tyr Trp  Lys Ser Met
    1565                 1570                 1575

Ser Lys  Val Phe Leu Glu Gln  Lys Val Ile Lys Tyr  Ile Leu Ser
    1580                 1585                 1590

Gln Asp  Ala Ser Leu His Arg  Val Lys Gly Cys His  Ser Phe Lys
    1595                 1600                 1605

Leu Trp  Phe Leu Lys Arg Leu  Asn Val Ala Glu Phe  Thr Val Cys
    1610                 1615                 1620

Pro Trp  Val Val Asn Ile Asp  Tyr His Pro Thr His  Met Lys Ala
    1625                 1630                 1635

Ile Leu  Thr Tyr Ile Asp Leu  Val Arg Met Gly Leu  Ile Asn Ile
    1640                 1645                 1650

Asp Arg  Ile His Ile Lys Asn  Lys His Lys Phe Asn  Asp Glu Phe
    1655                 1660                 1665

Tyr Thr  Ser Asn Leu Phe Tyr  Ile Asn Tyr Asn Phe  Ser Asp Asn
    1670                 1675                 1680

Thr His  Leu Leu Thr Lys His  Ile Arg Ile Ala Asn  Ser Glu Leu
    1685                 1690                 1695

Glu Asn  Asn Tyr Asn Lys Leu  Tyr His Pro Thr Pro  Glu Thr Leu
    1700                 1705                 1710

Glu Asn  Ile Leu Ala Asn Pro  Ile Lys Ser Asn Asp  Lys Lys Thr
    1715                 1720                 1725

Leu Asn  Asp Tyr Cys Ile Gly  Lys Asn Val Asp Ser  Ile Met Leu
    1730                 1735                 1740

Pro Leu  Leu Ser Asn Lys Lys  Leu Val Lys Ser Ser  Ala Met Ile
    1745                 1750                 1755

Arg Thr  Asn Tyr Ser Lys Gln  Asp Leu Tyr Asn Leu  Phe Pro Thr
    1760                 1765                 1770

Val Val  Ile Asp Arg Ile Ile  Asp His Ser Gly Asn  Thr Ala Lys
    1775                 1780                 1785

Ser Asn  Gln Leu Tyr Thr Thr  Thr Ser His Gln Ile  Ser Leu Val
    1790                 1795                 1800

His Asn  Ser Thr Ser Leu Tyr  Cys Met Leu Pro Trp  His His Ile
    1805                 1810                 1815

Asn Arg  Phe Asn Phe Val Phe  Ser Ser Thr Gly Cys  Lys Ile Ser
    1820                 1825                 1830

Ile Glu  Tyr Ile Leu Lys Asp  Leu Lys Ile Lys Asp  Pro Asn Cys
    1835                 1840                 1845

Ile Ala  Phe Ile Gly Glu Gly  Ala Gly Asn Leu Leu  Leu Arg Thr
    1850                 1855                 1860

Val Val  Glu Leu His Pro Asp  Ile Arg Tyr Ile Tyr  Arg Ser Leu
```

```
    1865                1870                1875

Lys Asp  Cys Asn Asp His Ser  Leu Pro Ile Glu Phe  Leu Arg Leu
    1880                1885                1890

Tyr Asn  Gly His Ile Asn Ile  Asp Tyr Gly Glu Asn  Leu Thr Ile
    1895                1900                1905

Pro Ala  Thr Asp Ala Thr Asn  Asn Ile His Trp Ser  Tyr Leu His
    1910                1915                1920

Ile Lys  Phe Ala Glu Pro Ile  Ser Leu Phe Val Cys  Asp Ala Glu
    1925                1930                1935

Leu Pro  Val Thr Val Asn Trp  Ser Lys Ile Ile Ile  Glu Trp Ser
    1940                1945                1950

Lys His  Val Arg Lys Cys Lys  Tyr Cys Ser Ser Val  Asn Lys Cys
    1955                1960                1965

Thr Leu  Ile Val Lys Tyr His  Ala Gln Asp Asp Ile  Asp Phe Lys
    1970                1975                1980

Leu Asp  Asn Ile Thr Ile Leu  Lys Thr Tyr Val Cys  Leu Gly Ser
    1985                1990                1995

Lys Leu  Lys Gly Ser Glu Val  Tyr Leu Val Leu Thr  Ile Gly Pro
    2000                2005                2010

Ala Asn  Ile Phe Pro Val Phe  Asn Val Val Gln Asn  Ala Lys Leu
    2015                2020                2025

Ile Leu  Ser Arg Thr Lys Asn  Phe Ile Met Pro Lys  Lys Ala Asp
    2030                2035                2040

Lys Glu  Ser Ile Asp Ala Asn  Ile Lys Ser Leu Ile  Pro Phe Leu
    2045                2050                2055

Cys Tyr  Pro Ile Thr Lys Lys  Gly Ile Asn Thr Ala  Leu Ser Lys
    2060                2065                2070

Leu Lys  Ser Val Val Ser Gly  Asp Ile Leu Ser Tyr  Ser Ile Ala
    2075                2080                2085

Gly Arg  Asn Glu Val Phe Ser  Asn Lys Leu Ile Asn  His Lys His
    2090                2095                2100

Met Asn  Ile Leu Lys Trp Phe  Asn His Val Leu Asn  Phe Arg Ser
    2105                2110                2115

Thr Glu  Leu Asn Tyr Asn His  Leu Tyr Met Val Glu  Ser Thr Tyr
    2120                2125                2130

Pro Tyr  Leu Ser Glu Leu Leu  Asn Ser Leu Thr Thr  Asn Glu Leu
    2135                2140                2145

Lys Lys  Leu Ile Lys Ile Thr  Gly Ser Leu Leu Tyr  Asn Phe His
    2150                2155                2160

Asn Glu
    2165


<210> SEQ ID NO 7
<211> LENGTH: 194
<212> TYPE: PRT
<213> ORGANISM: respiratory syncytial virus

<400> SEQUENCE: 7

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45
```

```
Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Leu Thr Val Ser Asp Thr Asn Asp His Ala Lys Asn Asn Asp
            180                 185                 190

Thr Thr


<210> SEQ ID NO 8
<211> LENGTH: 90
<212> TYPE: PRT
<213> ORGANISM: respiratory syncytial virus

<400> SEQUENCE: 8

Met Thr Met Pro Lys Ile Met Ile Leu Pro Asp Lys Tyr Pro Cys Ser
1               5                   10                  15

Ile Thr Ser Ile Leu Ile Thr Ser Arg Cys Arg Val Thr Met Tyr Asn
            20                  25                  30

Arg Lys Asn Thr Leu Tyr Phe Asn Gln Asn Asn Pro Asn Asn His Met
        35                  40                  45

Tyr Ser Pro Asn Gln Thr Phe Asn Glu Ile His Trp Thr Ser Gln Asp
    50                  55                  60

Leu Ile Asp Thr Ile Gln Asn Phe Leu Gln His Leu Gly Val Ile Glu
65                  70                  75                  80

Asp Ile Tyr Thr Ile Tyr Ile Leu Val Ser
                85                  90


<210> SEQ ID NO 9
<211> LENGTH: 241
<212> TYPE: PRT
<213> ORGANISM: respiratory syncytial virus

<400> SEQUENCE: 9

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Asn Ala Gly Asn Lys Pro Asn Tyr Gln
65                  70                  75                  80

Arg Lys Pro Leu Val Ser Phe Lys Glu Asp Pro Ile Pro Ser Asp Asn
```

```
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Ser Leu Asn Pro Thr Ser Glu Lys Leu Asn
    210                 215                 220

Asn Leu Leu Glu Gly Asn Asp Ser Asp Asn Asp Leu Ser Leu Glu Asp
225                 230                 235                 240

Phe


<210> SEQ ID NO 10
<211> LENGTH: 139
<212> TYPE: PRT
<213> ORGANISM: respiratory syncytial virus

<400> SEQUENCE: 10

Met Gly Ser Asn Ser Leu Ser Met Ile Lys Val Arg Leu Gln Asn Leu
1               5                   10                  15

Phe Asp Asn Asp Glu Val Ala Leu Leu Lys Ile Thr Cys Tyr Thr Asp
            20                  25                  30

Lys Leu Ile His Leu Thr Asn Ala Leu Ala Lys Ala Val Ile His Thr
        35                  40                  45

Ile Lys Leu Asn Gly Ile Val Phe Val His Val Ile Thr Ser Ser Asp
    50                  55                  60

Ile Cys Pro Asn Asn Asn Ile Val Val Lys Ser Asn Phe Thr Thr Met
65                  70                  75                  80

Pro Val Leu Gln Asn Gly Gly Tyr Ile Trp Glu Met Met Glu Leu Thr
                85                  90                  95

His Cys Ser Gln Pro Asn Gly Leu Ile Asp Asp Asn Cys Glu Ile Lys
            100                 105                 110

Phe Ser Lys Lys Leu Ser Asp Ser Thr Met Thr Asn Tyr Met Asn Gln
        115                 120                 125

Leu Ser Glu Leu Leu Gly Phe Asp Leu Asn Pro
    130                 135


<210> SEQ ID NO 11
<211> LENGTH: 124
<212> TYPE: PRT
<213> ORGANISM: respiratory syncytial virus

<400> SEQUENCE: 11

Met Asp Thr Thr His Asn Asp Thr Thr Pro Gln Arg Leu Met Ile Thr
1               5                   10                  15

Asp Met Arg Pro Leu Ser Leu Glu Thr Thr Ile Thr Ser Leu Thr Arg
            20                  25                  30
```

```
Asp Ile Ile Thr His Arg Phe Ile Tyr Leu Ile Asn His Glu Cys Ile
        35                  40                  45

Val Arg Lys Leu Asp Glu Arg Gln Ala Thr Phe Thr Phe Leu Val Asn
    50                  55                  60

Tyr Glu Met Lys Leu Leu His Lys Val Gly Ser Thr Lys Tyr Lys Lys
65                  70                  75                  80

Tyr Thr Glu Tyr Asn Thr Lys Tyr Gly Thr Phe Pro Met Pro Ile Phe
                85                  90                  95

Ile Asn His Asp Gly Phe Leu Glu Cys Ile Gly Ile Lys Pro Thr Lys
            100                 105                 110

His Thr Pro Ile Ile Tyr Lys Tyr Asp Leu Asn Pro
        115                 120


<210> SEQ ID NO 12
<211> LENGTH: 1725
<212> TYPE: RNA
<213> ORGANISM: respiratory syncytial virus

<400> SEQUENCE: 12

auggaguugc caauccucaa agcaaaugca auuaccacaa uccucgcugc agucacauuu      60

ugcuuugcuu cuagucaaaa caucacugaa gaauuuuauc aaucaacaug cagugcaguu     120

agcaaaggcu aucuuagugc ucuaagaacu gguugguaua cuaguguuau aacuauagaa     180

uuaaguaaua ucaaggaaaa uaaguguaau ggaacagaug cuaagguaaa auugauaaac     240

caagaauuag auaaauauaa aaaugcugua acagaauugc aguugcucau gcaaagcaca     300

acagcagcaa acaaucgagc cagaagagaa cuaccaaggu uuaugaauua uacacucaac     360

aauaccaaaa aaaccaaugu aacauuaagc aagaaaagga aaagaagauu ucuugguuuu     420

uuguuaggug uuggaucugc aaucgccagu ggcauugcug uaucuaaggu ccugcacuua     480

gaaggagaag ugaacaagau caaaagugcu cuacuaucca caaacaaggc cguagucagc     540

uuaucaaaug gaguuagugu cuuaaccagc aaaguguuag accucaaaaa cuauauagau     600

aaacaauugu uaccuauugu gaauaagcaa agcugcagaa uaucaaauau agaaacugug     660

auagaguucc aacaaaagaa caacagacua cuagagauua ccagggaauu uaguguuaau     720

gcaggaguaa cuacaccugu aagcacuuac auguuaacua auagugaauu auugucauua     780

aucaaugaua ugccuauaac aaaugaucag aaaaaguuaa uguccaacaa uguucaaaua     840

guuagacagc aaaguuacuc uaucaugucc auaauaaaag aggaagucuu agcauaugua     900

guacaauuac cacuauaugg ugugauagau acaccuuguu ggaaauuaca cacauccccu     960

cuauguacaa ccaacacaaa agaaggguca aacaucuguu uaacaagaac ugacagagga    1020

ugguacugug acaaugcagg aucaguaucu uucuucccac aagcugaaac auguaaaguu    1080

caaucgaauc gaguauuuug ugacacaaug aacaguuuaa cauuaccaag ugaaguaaau    1140

cucugcaaug uugacauauu caaucccaaa uaugauugua aaauuaugac uucaaaaaca    1200

gauguaagca gcuccguuau cacaucucua ggagccauug ugucaugcua uggcaaaacu    1260

aaauguacag cauccaauaa aaaucgugga aucauaaaga cauuuucuaa cgggugugau    1320

uauguaucaa auaaaggggu ggacacugug ucuguaggua acacauuaua uuauguaaau    1380

aagcaagaag gcaaaagucu cuauguaaaa ggugaaccaa uaauaaauuu cuaugaccca    1440

uuaguauucc ccucugauga auuugaugca ucaauaucuc aagucaauga gaagauuaac    1500

cagaguuuag cauuuauucg uaaauccgau gaauuauuac aucauguaaa ugcugguaaa    1560
```

```
ucaaccacaa auaucaugau aacuacuaua auuauaguga uuauaguaau auuguuauca   1620

uuaauugcug uuggacugcu ccuauacugu aaggccagaa gcacaccagu cacacuaagc   1680

aaggaucaac ugagugguau aaauaauauu gcauuuagua acuga                   1725


<210> SEQ ID NO 13
<211> LENGTH: 897
<212> TYPE: RNA
<213> ORGANISM: respiratory syncytial virus

<400> SEQUENCE: 13

auguccaaaa acaaggacca acgcaccgcu aagacacuag aaaagaccug ggacacucuc     60

aaucauuuau uauucauauc aucgggcuua uauaaguuaa aucuuaaauc uauagcacaa    120

aucacauuau ccauucuggc aaugauaauc ucaacuucac uuauaauuac agccaucaua    180

uucauagccu cggcaaacca caaagucaca cuaacaacug caaucauaca agaugcaaca    240

agccagauca agaacacaac cccaacauac cucacucagg auccucagcu uggaaucagc    300

uucuccaauc ugucugaaau uacaucacaa accaccacca uacuagcuuc aacaacacca    360

ggagucaagu caaaccugca acccacaaca gucaagacua aaaacacaac aacaacccaa    420

acacaaccca gcaagcccac uacaaaacaa cgccaaaaca aaccaccaaa caaacccaau    480

aaugauuuuc acuucgaagu guuuaacuuu guacccugca gcauaugcag caacaaucca    540

accugcuggg cuaucugcaa aagaauacca aacaaaaaac caggaaagaa aaccaccacc    600

aagccuacaa aaaaaccaac cuucaagaca accaaaaaag aucucaaacc ucaaaccacu    660

aaaccaaagg aaguacccac caccaagccc acagaagagc caaccaucaa caccaccaaa    720

acaaacauca caacuacacu gcucaccaac aacaccacag gaaauccaaa acucacaagu    780

caaauggaaa ccuuccacuc aaccuccucc gaaggcaauc uaagcccuuc ucaagucucc    840

acaacauccg agcacccauc acaacccuca ucuccaccca acacaacacg ccaguag       897


<210> SEQ ID NO 14
<211> LENGTH: 195
<212> TYPE: RNA
<213> ORGANISM: respiratory syncytial virus

<400> SEQUENCE: 14

auggaaaaua cauccauaac aauagaauuc ucaagcaaau ucuggccuua cuuuacacua     60

auacacauga ucacaacaau aaucucuuug cuaaucauaa ucuccaucau gacugcaaua    120

cuaaacaaac uuugugaaua uaacguauuc cauaacaaaa ccuuugaguu accaagagcu    180

cgagucaaca cauag                                                     195


<210> SEQ ID NO 15
<211> LENGTH: 771
<212> TYPE: RNA
<213> ORGANISM: respiratory syncytial virus

<400> SEQUENCE: 15

auggaaacau acgugaacaa gcuucacgaa ggcuccacau acacagcugc uguucaauac     60

aauguccuag aaaaagacga ugacccugca ucacuuacaa uaugggugcc cauguuccaa    120

ucaucuaugc cagcagauuu acuuauaaaa gaacuagcua augucaacau acuagugaaa    180

caaauaucca cacccaaggg accuucacua agagucauga uaaacucaag aagugcauug    240

cuagcacaaa ugcccagcaa auuuaccaua ugugcuaaug uguccuugga ugaaagaagc    300

aaacuggcau augauguaac cacacccugu gaaaucaagg cauguagucu aacaugccua    360
```

```
aaaucaaaaa auauguuaac uacaguuaaa gaucucacua ugaagacacu caaccccaca    420

caugauauua uugcuuuaug ugaauuugaa aacauaguaa caucaaaaaa agucauaaua    480

ccaacauacc uaagauccau cagugucaga aauaaagauc ugaacacacu ugaaaauaua    540

acaaccacug aauucaaaaa ugccaucaca aaugcaaaaa ucaucccuua cucaggauua    600

cuauuaguca ucacagugac ugacaacaaa ggagcauuca aauacauaaa gccgcaaagu    660

caauucauag uagaucuugg agcuuaccua gaaaaagaaa guauauauua uguuaccaca    720

aauuggaagc acacagcuac acgauuugca aucaaaccca uggaagauua a             771
```

<210> SEQ ID NO 16
<211> LENGTH: 1176
<212> TYPE: RNA
<213> ORGANISM: respiratory syncytial virus

<400> SEQUENCE: 16

```
auggcucuua gcaaagucaa guugaaugau acacucaaca aagaucaacu ucugucaucu     60

agcaaauaca ccauccaacg gagcacagga gauaguauug auacuccuaa uuaugaugug    120

cagaaacaca ucaauaaguu auguggcaug uuauuaauca cagaagaugc uaaucauaaa    180

uucacugggu uaauagguau guuauaugcu augucuaggu uaggaagaga agacaccaua    240

aaaauacuca gagaugcggg auaucaugua aaagcaaaug gaguagaugu aacaacacau    300

cgucaagaca ucaaugggaa agaaaugaaa uuugaagugu uaacauuggc aagcuuaaca    360

acugaaauuc aaaucaacau ugagauagaa ucuagaaaau ccuacaaaaa aaugcuaaaa    420

gaaaugggag agguagcucc agaauacagg caugauucuc cugauugugg gaugauaaua    480

uuauguauag cagcauuagu aauaaccaaa uuggcagcag gggauagauc uggucuuaca    540

gccgugauua ggagagcuaa uaauguccua aaaaaugaaa ugaaacguua caaaggcuua    600

cuacccaagg auauagccaa cagcuucuau gaaguguuug aaaaacaucc ccacuuuaua    660

gauguuuuug uucauuuugg uauagcacaa ucuuccacca gagguggcag uagaguugaa    720

gggauuuuug caggauuguu uaugaaugcc uauggugcag ggcaaguaau gcuacggugg    780

ggagucuuag caaaaucagu uaaaaauauu auguuaggac augcuagugu gcaagcagaa    840

auggaacaag uuguugaggu uuaugaauau gcccaaaaau ugggguggaga agcaggauuc    900

uaccauauau ugaacaaccc aaaagcauca uuauuaucuu ugacucaauu uccucacuuu    960

uccaguguag uauuaggcaa ugcugcuggc cuaggcauaa ugggagagua cagagguaca   1020

ccgaggaauc aagaucuaua ugaugcagca aaggcauaug cugaacaacu caaagaaaau   1080

ggugugauua acuacagugu auuagacuug acagcagaag aacuagaggc uaucaaacau   1140

cagcuuaauc caaaagauaa ugauguagag cuuuga                             1176
```

<210> SEQ ID NO 17
<211> LENGTH: 6498
<212> TYPE: RNA
<213> ORGANISM: respiratory syncytial virus

<400> SEQUENCE: 17

```
auggauccca uuauuaaugg aaauucugcu aauguuuauc uaaccgauag uuauuuaaaa     60

gguguuaucu cuuucucaga guguaaugcu uuaggaaguu acauauucaa ugguccuuau    120

cucaaaaaug auuauaccaa cuuaauuagu agacaaaauc cauuaauaga acacaugaau    180

cuaaagaaac uaaauauaac acaguccuua auaucuaagu aucauaaagg ugaaauaaaa    240
```

-continued

```
uuagaagagc cuacuuauuu ucagucauua cuuaugacau acaagaguau gaccucguug    300
gaacagauug cuaccacuaa uuuacuuaaa aagauaauaa gaagagcuau agaaauaagu    360
gaugucaaag ucuaugcuau auugaauaaa cuagggcuua aagaaaagga caagauuaaa    420
uccaacaaug gacaggauga agacaacuca guuauuacga ccauaaucaa agaugauaua    480
cuuucagcug uuaaggauaa ucaaucucau cuuaaagcag acaaaaauca cucuacaaaa    540
caaaaagaca caaucaaaac aacacucuug aagaaauuaa uguguucaau gcagcauccu    600
ccaucauggu uaauacauug guuuaauuua uacacaaaau uaaacaacau auuaacacag    660
uaucgaucaa augagguuaa aaaccauggg uuuauauuga uagauaauca aacucuuagu    720
ggauuucaau uuauuuugaa ucaauauggu uguauaguuu aucauaagga acucaaaaga    780
auuacuguga caaccuauaa ucaauucuug acauggaaag auauuagccu uaguagauua    840
aauguuuguu uaauuacaug gauuaguaac ugcuugaaca cauuaaauaa aagcuuaggc    900
uuaagaugcg gauucaauaa uguuaucuug acacaacuau uccuuuaugg ugauuguaua    960
cuaaagcuau uucacaauga gggguucuac auaauaaaag agguagaggg auuuauuaug   1020
ucucuaauuu uaaauauaac agaagaagau caauucagaa aacgauuuua uaauaguaug   1080
cucaacaaca ucacagaugc ugcuaauaaa gcucagaaaa aucugcuauc aagaguaugu   1140
cauacauuau uagauaagac aguauccgau aauauaauaa auggcagaug gauaauucua   1200
uuaaguaagu uccuuaaauu aauuaagcuu gcaggugaca auaaccuuaa caaucugagu   1260
gaacuauauu uuuuguucag aauauuugga cacccaaugg uagaugaaag acaagccaug   1320
gaugcuguua aaguuaauug caaugagacc aaauuuuacu uguuaagcag uuugaguaug   1380
uuaagaggug ccuuuauaua uagaauuaua aaaggguuug uaaauaauua caacagaugg   1440
ccuacuuuaa gaaaugcuau uguuuuaccc uuaagauggu uaacuuacua uaaacuaaac   1500
acuuauccuu cuuuguugga acuuacagaa agagauuuga uuguguuauc aggacuacgu   1560
uucuaucgug aguuucgguu gccuaaaaaa guggaucuug aaaugauuau aaaugauaaa   1620
gcuauaucac ccccuaaaaa uuugauaugg acuaguuucc cuagaaauua uaugccguca   1680
cacauacaaa acuauauaga acaugaaaaa uuaaaauuuu ccgagaguga uaaaucaaga   1740
agaguauuag aguauuauuu aagagauaac aaauucaaug aaugugauuu auacaacugu   1800
guaguuaauc aaaguuaucu caacaacccu aaucaugugg uaucauugac aggcaaagaa   1860
agagaacuca guguaggugag aauguuugca augcaaccgg gaauguucag acagguucaa   1920
auauuggcag agaaaaugau agcugaaaac auuuuacaau ucuuuccuga aagucuuaca   1980
agauauggug aucuagaacu acaaaaaaua uuagaauuga aagcaggaau aaguaacaaa   2040
ucaaaucgcu acaaugauaa uuacaacaau uacauuagua agugcucuau caucacagau   2100
cucagcaaau ucaaucaagc auuucgauau gaaacgucau guauuuguag ugaugugcug   2160
gaugaacugc augguguaca aucucuauuu uccugguuac auuuaacuau uccucauguc   2220
acaauaauau gcacauauag gcaugcaccc cccuauauaa gagaucauau uguagaucuu   2280
aacaauguag augaacaaag uggauuauau agauaucaca uggguggaau ugaagggugg   2340
ugucaaaaac uauggaccau agaagcuaua ucacuauugg aucuaauauc ucucaaaggg   2400
aaauucucaa uuacugcuuu aauuaauggu gacaaucaau caauagauau aagcaaacca   2460
gucagacuca uggaagguca aacucaugcu caagcagauu auuugcuagc auuaaauagc   2520
cuuaaauuac uguauaaaga guaugcaggc auaggucaca aauuaaaagg aacugagacu   2580
uauauaucac gagauaugca auuuaugagu aaaacaauuc aacauaacgg uguauauuac   2640
```

```
ccugcuagua uaaagaaagu ccuaagagug ggaccgugga uaaacacuau acuugaugau   2700
uucaaaguga gucuagaauc uauagguagu uugacacaag aauuagaaua uagaggugaa   2760
agucuauuau gcaguuuaau auuuagaaau guaugguuau auaaucaaau ugcucuacaa   2820
uuaaaaaauc augcguuaug uaacaauaaa uuauauuugg acauauuaaa gguucugaaa   2880
cacuuaaaaa ccuuuuuuaa ucuugauaau auugauacag cauuaacauu guauaugaau   2940
uuacccaugu uauuuggugg uggugauccc aacuuguuau aucgaaguuu cuauagaaga   3000
acuccugauu uccucacaga ggcuauaguu cacucugugu ucauacuuag uuauuauaca   3060
aaccaugacu uaaaagauaa acuucaagau uugucagaug auagauugaa uaaguucuua   3120
acaugcauaa ucacguuuga caaaaacccu aaugcugaau ucguaacauu gaugagagau   3180
ccucaagcuu uagggucuga gagacaagcu aaaauuacua gugaaaucaa uagacuggca   3240
guuacagagg uuuugaguac agcuccaaac aaaauauucu ccaaaagugc acaacauuau   3300
accacuacag agauagaucu aaaugauauu augcaaaaua uagaaccuac auauccucac   3360
gggcuaagag uuguuuauga aaguuuaccc uuuuauaaag cagagaaaau aguaaaucuu   3420
auaucaggua caaaaucuau aacuaacaua cuggaaaaga cuucugccau agacuuaaca   3480
gauauugaua gagccacuga gaugaugagg aaaaacauaa cuuugcuuau aaggauacuu   3540
ccauuggauu guaacagaga uaaaagagaa auauugagua uggaaaaccu aaguauuacu   3600
gaauuaagca aauauguuag ggaaagaucu uggucuuuau ccaauauagu ugguguuaca   3660
ucacccagua ucauguauac aauggacauc aaauauacaa caagcacuau agcuaguggc   3720
auaauuauag agaaauauaa uguuaacagu uuaacacgug gugagagagg accaacuaaa   3780
ccauggguug guucaucuac acaagagaaa aaaacaaugc caguuuauaa uagacaaguu   3840
uuaaccaaaa aacaaagaga ucaaauagau cuauuagcaa aauuggauug gguguaugca   3900
ucuauagaua acaaggauga auucauggaa gaacucagca uaggaacccu uggguuaaca   3960
uaugaaaagg ccaaaaaauu auuuccacaa uauuuaagug ucaacuauuu gcaucgccuu   4020
acagucagua guagaccaug ugaauucccu gcaucaauac cagcuuauag aacaacaaau   4080
uaucacuuug acacuagccc uauuaaucgc auauuaacag aaaaguaugg ugaugaagau   4140
auugacauag uauuccaaaa cuguauaagc uuuggccuua gcuuaauguc aguaguagaa   4200
caauuuacua auguaugucc uaacagaauu auucucauac cuaagcuuaa ugagauacau   4260
uugaugaaac cucccauauu cacaggugau guugauauuc acaaguuaaa acaagugaua   4320
caaaaacagc auauguuuuu accagacaaa auaaguuuga cucaauaugu ggaauuauuc   4380
uuaaguaaca aaacacucaa aucuggaucu cauguuaauu cuaauuuaau auuggcacau   4440
aaaauaucug acuauuuuca uaauacuuac auuuuaagua cuaauuuagc uggacauugg   4500
auucuaauua uacaacuuau gaaagauucu aaagguauuu uugaaaaaga uuggggagag   4560
ggauauauaa cugaucauau guuuauuaau uugaaaguuu ucuucaaugc uuauaagacc   4620
uaucucuugu guuuucauaa agguuauggc aaagcaaaac uggaguguga uaugaacacu   4680
ucagaucuuc uauguguauu ggaauuaaua gacaguaguu auuggaaguc uaugucuaag   4740
guauuuuuag aacaaaaagu uaucaaauac auucuuagcc aagaugcaag uuuacauaga   4800
guaaaaggau gucauagcuu caaauuaugg uuucuuaaac gucuuaaugu agcagaauuu   4860
acaguuugcc cuuggguugu uaacauagau uaucauccaa cacauaugaa agcaauauua   4920
acuuauauag aucuuguuag aaugggauug auaaauauag auagaauaca cauuaaaaau   4980
```

```
aaacacaaau ucaaugauga auuuuauacu ucuaaucucu uuuacauuaa uuauaacuuc   5040

ucagauaaua cucaucuauu aacuaaacau auaaggauug cuaauucaga auuagaaaau   5100

aauuacaaca aauuauauca uccuacacca gaaacccuag agaauauacu agccaauccg   5160

auuaaaagua augacaaaaa gacacugaac gacuauugua uagguaaaaa uguugacuca   5220

auaauguuac cauuguuauc uaauaagaag cuuguuaaau cgucugcaau gauuagaacc   5280

aauuacagca aacaagaccu guacaaucua uucccuacgg uugugaucga uagaauuaua   5340

gaucauucag guaauacagc caaauccaac caacuuuaca cuacuacuuc ccaucaaaua   5400

ucuuuagugc acaauagcac aucacuuuau ugcaugcuuc cuuggcauca uauuaauaga   5460

uucaauuuug uauuuaguuc uacagguugu aaaauuagua uagaguauau uuuaaaagac   5520

cuuaaaauua aagauccuaa uuguauagca uucauaggug aaggagcagg gaauuuauua   5580

uugcguacag ugguggaacu ucauccugac auaagauaua uuuacagaag ucugaaagau   5640

ugcaaugauc auaguuuacc uauugaguuu uuaaggcuau acaauggaca uaucaacauu   5700

gauuauggug aaaauuugac cauuccugcu acagaugcaa ccaacaacau ucauugguc u   5760

uauuuacaua uaaaguuugc ugaaccuauc agucuuuuug uaugugaugc cgaauugccu   5820

guaacaguca acuggaguaa aauuauaaua gaauggagca agcauguaag aaaaugcaag   5880

uacuguuccu caguuaauaa auguacguua auaguaaaau aucaugcuca agaugauauu   5940

gauuucaaau uagacaauau aacuauauua aaaacuuaug uaugcuuagg caguaaguua   6000

aagggaucgg agguuuacuu aguccuuaca auagguccug caaauauauu uccaguauuu   6060

aauguaguac aaaaugcuaa auugauacua ucaagaacca aaaauuucau caugccuaag   6120

aaagcugaua aagagucuau ugaugcaaau auuaaaaguu ugauacccuu ucuuuguuac   6180

ccuauaacaa aaaaaggaau uaauacugca uugucaaaac uaaagagugu uguuagugga   6240

gauauacuau cauauucuau agcuggacgg aaugaaguuu ucagcaauaa acuuauaaau   6300

cauaagcaua ugaacaucuu aaagugguuc aaucauguuu uaaauuucag aucaacagaa   6360

cuaaacuaua accauuuaua uaugguagaa ucuacauauc cuuaccuaag ugaauuguua   6420

aacagcuuga caacuaauga acuuaaaaaa cugauuaaaa ucacagguag ucuguuauac   6480

aacuuucaua augaauaa                                                 6498
```

<210> SEQ ID NO 18
<211> LENGTH: 585
<212> TYPE: RNA
<213> ORGANISM: respiratory syncytial virus

<400> SEQUENCE: 18

```
augucacgaa ggaauccuug caaauuugaa auucgagguc auugcuugaa ugguaagaga     60

ugucauuuua gucauaauua uuuugaaugg ccaccccaug cacugcucgu aagacaaaac    120

uuuauguuaa acagaauacu uaagucuaug gauaaaagua uagauaccuu aucagaaaua    180

aguggagcug cagaguugga cagaacagaa gaguaugcuc uuggugugagu uggagugcua    240

gagaguuaua uaggaucaau aaauaauaua acuaaacaau cagcaugugu ugccaugagc    300

aaacuccuca cugaacucaa uagugaugau aucaaaaaac ugagagacaa ugaagagcua    360

aauucaccca agauaagagu guacaauacu gucauaucau auauugaaag caacaggaaa    420

aacaauaaac aaacuaucca ucuguuaaaa agauugccag cagacguauu gaagaaaacc    480

aucaaaaaca cauuggauau ccacaagagc auaaccauca acaacccaaa agaauuaacu    540

guuagugaua caaaugacca ugccaaaaau aaugauacua ccuga                    585
```

<210> SEQ ID NO 19
<211> LENGTH: 273
<212> TYPE: RNA
<213> ORGANISM: respiratory syncytial virus

<400> SEQUENCE: 19

```
augaccaugc caaaaauaau gauacuaccu gacaaauauc cuuguaguau aacuuccaua     60

cuaauaacaa guagauguag agucacuaug uauaaucgaa agaacacacu auauuucaau    120

caaaacaacc caaauaacca uauguacuca ccgaaucaaa cauucaauga aauccauugg    180

accucacaag acuugauuga cacaauucaa aauuuucuac agcaucuagg uguuauugag    240

gauauauaua caauauauau auuaguguca uaa                                 273
```

<210> SEQ ID NO 20
<211> LENGTH: 726
<212> TYPE: RNA
<213> ORGANISM: respiratory syncytial virus

<400> SEQUENCE: 20

```
auggaaaagu uugcuccuga auuccaugga gaagaugcaa acaacagggc uacuaaauuc     60

cuagaaucaa uaaagggcaa auucacauca ccuaaagauc ccaagaaaaa agauaguauc    120

auaucuguca acucaauaga uauagaagua accaaagaaa gcccuauaac aucaaauuca    180

accauuauua acccaacaaa ugagacagau gauaaugcag ggaacaagcc caauuaucaa    240

agaaaaccuc uaguaaguuu caaagaagac ccuauaccaa gugauaaucc cuuuucaaaa    300

cuauacaaag aaaccauaga gacauuugau aacaaugaag aagaaucuag cuauucauau    360

gaagaaauaa augaucagac gaacgauaau auaacugcaa gauuagauag gauugaugaa    420

aaauuaagug aaauacuagg aaugcuucac acauuaguag uagcaagugc aggaccuaca    480

ucugcuaggg augguauaag agaugccaug guugguuuaa gagaagaaau gauagaaaaa    540

aucagaacug aagcauuaau gaccaaugac agauuagaag cuauggcaag acucaggaau    600

gaggaaagug aaaagauggc aaaagacaca ucagaugaag ugucucucaa uccaacauca    660

gagaaauuga acaaccuguu ggaagggaau gauagugaca augaucuauc acuugaagau    720

uucuga                                                               726
```

<210> SEQ ID NO 21
<211> LENGTH: 420
<212> TYPE: RNA
<213> ORGANISM: respiratory syncytial virus

<400> SEQUENCE: 21

```
augggcagca auucguugag uaugauaaaa guuagauuac aaaauuuguu ugacaaugau     60

gaaguagcau uguuaaaaau aacaugcuau acugacaaau uaauacauuu aacuaaugcu    120

uuggcuaagg cagugauaca uacaaucaaa uugaauggca uuguguuugu gcauguuauu    180

acaaguagug auauuugccc uaauaauaau auuguaguaa aauccaauuu cacaacaaug    240

ccagugcuac aaaauggagg uuauauaugg gaaaugaugg aauuaacaca uugcucucaa    300

ccuaauggucuaauagauga caauugugaa auuaaauucu ccaaaaaacu aagugauuca    360

acaaugacca auuauaugaa ucaauuaucu gaauuacuug gauuugaucu uaauccauaa    420
```

<210> SEQ ID NO 22
<211> LENGTH: 375
<212> TYPE: RNA

<213> ORGANISM: respiratory syncytial virus

<400> SEQUENCE: 22
auggacacaa cccacaauga uaccacacca caaagacuga ugaucacaga caugagaccg 60
uugucacuug agacuacaau aacaucacua accagagaca ucauaacaca cagauuuaua 120
uacuuaauaa aucaugaaug cauagugaga aaacuugaug aaagacaggc cacauuuaca 180
uuccugguca acuaugaaau gaaacuauug cacaaaguag gaagcacuaa auauaaaaaa 240
uauacugaau acaacacaaa auauggcacu uucccuaugc cgauauucau caaucaugau 300
ggguucuuag aaugcauugg cauuaagccu acaaagcaua cucccauaau auacaaguau 360
gaucucaauc cauag 375

<210> SEQ ID NO 23
<211> LENGTH: 42
<212> TYPE: DNA
<213> ORGANISM: Homo sapiens

<400> SEQUENCE: 23
ggcgctgcct acggaggtgg cagccatctc cttctcggca tc 42

<210> SEQ ID NO 24
<211> LENGTH: 186
<212> TYPE: DNA
<213> ORGANISM: Homo sapiens

<400> SEQUENCE: 24
catcacattt aaaagcatct cagcctacca tgagaataag agaaagaaaa tgaagatcaa 60
aagcttattc atctgttttt ctttttcgtt ggtgtaaagc caacaccctg tctaaaaaac 120
ataaatttct ttaatcattt tgcctctttt ctctgtgctt caattaataa aaaatggaaa 180
gaatct 186

<210> SEQ ID NO 25
<211> LENGTH: 186
<212> TYPE: DNA
<213> ORGANISM: Homo sapiens

<400> SEQUENCE: 25
catcacattt aaaagcatct cagcctacca tgagaataag agaaagaaaa tgaagatcaa 60
tagcttattc atctcttttt ctttttcgtt ggtgtaaagc caacaccctg tctaaaaaac 120
ataaatttct ttaatcattt tgcctctttt ctctgtgctt caattaataa aaaatggaaa 180
gaacct 186

<210> SEQ ID NO 26
<211> LENGTH: 110
<212> TYPE: DNA
<213> ORGANISM: Homo sapiens

<400> SEQUENCE: 26
gctggagcct cggtggccat gcttcttgcc ccttgggcct ccccccagcc cctcctcccc 60
ttcctgcacc cgtacccccg tggtctttga ataaagtctg agtgggcggc 110

<210> SEQ ID NO 27
<211> LENGTH: 108
<212> TYPE: DNA
<213> ORGANISM: Homo sapiens

<400> SEQUENCE: 27
gctggagcct cggtagccgt tcctcctgcc cgctgggcct cccaacgggc cctcctcccc 60
tccttgcacc ggcccttcct ggtctttgaa taaagtctga gtgggcag 108

<210> SEQ ID NO 28
<211> LENGTH: 132
<212> TYPE: DNA
<213> ORGANISM: Homo sapiens

<400> SEQUENCE: 28
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt gc 132

<210> SEQ ID NO 29
<211> LENGTH: 44
<212> TYPE: DNA
<213> ORGANISM: Artificial Sequence
<220> FEATURE:
<223> OTHER INFORMATION: Center, alpha-complex-binding portion of the 3'UTR of an alpha-globin gene (muag)

<400> SEQUENCE: 29
gcccgatggg cctcccaacg ggccctcctc ccctccttgc accg 44

<210> SEQ ID NO 30
<211> LENGTH: 24
<212> TYPE: DNA
<213> ORGANISM: Artificial Sequence
<220> FEATURE:
<223> OTHER INFORMATION: particular preferred histone stem-loop sequence

<400> SEQUENCE: 30
caaaggctct tttcagagcc acca 24

<210> SEQ ID NO 31
<211> LENGTH: 1942
<212> TYPE: RNA
<213> ORGANISM: Artificial Sequence
<220> FEATURE:
<223> OTHER INFORMATION: RSV-F long (GC) R1691

<400> SEQUENCE: 31
gggagaaagc uuaccaugga gcugcccauc cucaaggcca acgccaucac caccauccug 60
gcggccguga cguucugcuu cgccagcucc cagaacauca ccgaggaguu cuaccagagc 120
accugcuccg ccgucagcaa gggcuaccug uccgcccucc ggaccgggug guacacgagc 180
gugaucacca ucgagcuguc caacaucaag gagaacaagu gcaacggcac cgacgcgaag 240
gugaagcuga ucaaccagga gcucgacaag uacaagaacg ccgucaccga gcugcagcug 300
cucaugcaga gcacgaccgc cgccaacaac cgcgcgcggc gcgagcugcc gcgguucaug 360
aacuacaccc ugaacaacac caagaagacg aacgugaccc ucuccaagaa gcgcaagcgg 420
cgcuuccugg gguuccugcu cggcgugggg agcgccaucg ccuccggcau cgccgucagc 480
aaggugcugc accuggaggg cgaggugaac aagaucaagu ccgcccuccu gagcaccaac 540
aaggcggucg ugucccugag caacggggug uccguccuca ccagcaaggu gcuggaccug 600
aagaacuaca ucgacaagca gcuccugccc aucgugaaca agcaguccug ccggaucagc 660
aacaucgaga cggucaucga guuccagcag aagaacaacc gccugcucga gaucacccgg 720
gaguucagcg ugaacgccgg cgugaccacc cccgucucca cguacaugcu gaccaacagc 780

```
gagcugcucu cccugaucaa cgacaugccc aucaccaacg accagaagaa gcugaugagc    840

aacaacgugc agaucgugcg ccagcagucc uacagcauca uguccaucau caaggaggag    900

guccucgccu acguggugca gcugccgcug uacgggguca ucgacacccc cugcuggaag    960

cuccacacga gccccugug caccaccaac accaaggagg gcuccaacau cugccugacg   1020

cggaccgacc gcggguggua cugcgacaac gccggcagcg uguccuucuu cccccaggcc   1080

gagaccugca agguccagag caaccgggug uucugcgaca ccaugaacuc ccucacgcug   1140

ccgagcgagg ugaaccugug caacgucgac aucuucaacc ccaaguacga cugcaagauc   1200

augaccucca agaccgacgu gagcuccagc gugaucaccu cccucggcgc gaucgucagc   1260

ugcuacggga agacgaagug caccgccagc aacaagaacc gcggcaucau caagaccuuc   1320

uccaacgggu gcgacuacgu gagcaacaag ggcguggaca ccgucuccgu gggcaacacc   1380

cuguacuacg ugaacaagca ggaggggaag agccuguacg ucaagggcga gcccaucauc   1440

aacuucuacg acccccucgu guucccgucc gacgaguucg acgccagcau cucccaggug   1500

aacgagaaga ucaaccagag ccuggccuuc auccggaagu ccgacgagcu gcugcaccac   1560

gucaacgccg ggaagagcac gaccaacauc augaucacca ccaucaucau cgugaucauc   1620

gugauccucc ugucccugau cgcggucggc cuccugcugu acugcaaggc ccgcagcacg   1680

cccgugaccc ucuccaagga ccagcugagc gggaucaaca acaucgccuu cuccaacuga   1740

ggacuaguua uaagacugac uagcccgaug ggccucccaa cgggcccucc uccccuccuu   1800

gcaccgagau uaauaaaaaa aaaaaaaaaa aaaaaaaaaa aaaaaaaaaa aaaaaaaaaa   1860

aaaaaaaaaa aaaaaaaaug caucccccc cccccccccc cccccccccc ccccaaaggc   1920

ucuuuucaga gccaccagaa uu                                            1942
```

<210> SEQ ID NO 32
<211> LENGTH: 2107
<212> TYPE: RNA
<213> ORGANISM: Artificial Sequence
<220> FEATURE:
<223> OTHER INFORMATION: RSV-F long (GC) R2510

<400> SEQUENCE: 32

```
ggggcgcugc cuacggaggu ggcagccauc uccuucucgg caucaagcuu accauggagc     60

ugcccauccu caaggccaac gccaucacca ccauccuggc ggccgugacg uucugcuucg    120

ccagcuccca gaacaucacc gaggaguucu accagagcac cugcuccgcc gucagcaagg    180

gcuaccuguc cgcccuccgg accgggugu acacgagcgu gaucaccauc gagcugucca    240

acaucaagga gaacaagugc aacggcaccg acgcgaaggu gaagcugauc aaccaggagc    300

ucgacaagua caagaacgcc gucaccgagc ugcagcugcu caugcagagc acgaccgccg    360

ccaacaaccg cgcgcggcgc gagcugccgc gguucaugaa cuacacccug aacaacacca    420

agaagacgaa cgugacccuc uccaagaagc gcaagcggcg cuuccugggg uuccugcucg    480

gcguggggag cgccaucgcc uccggcaucg ccgucagcaa ggugcugcac cuggagggcg    540

aggugaacaa gaucaagucc gcccuccuga gcaccaacaa ggcggucgug ucccugagca    600

acggggugc cguccucacc agcaaggugc uggaccugaa gaacuacauc gacaagcagc    660

uccugcccau cgugaacaag caguccugcc ggaucagcaa caucgagacg gucaucgagu    720

uccagcagaa gaacaaccgc cugcucgaga ucacccggga guucagcgug aacgccggcg    780

ugaccacccc cgucuccacg uacaugcuga ccaacagcga gcugcucucc cugaucaacg    840
```

```
acaugcccau caccaacgac cagaagaagc ugaugagcaa caacgugcag aucgugcgcc    900
agcaguccua cagcaucaug uccaucauca aggaggaggu ccucgccuac guggugcagc    960
ugccgcugua cggggucauc gacacccccu gcuggaagcu ccacacgagc cccugugca    1020
ccaccaacac caaggagggc uccaacaucu gccugacgcg gaccgaccgc ggguggua cu  1080
gcgacaacgc cggcagcgug uccuucuucc cccaggccga gaccugcaag guccagagca   1140
accgggguguu cugcgacacc augaacuccc ucacgcugcc gagcgaggug aaccugugca  1200
acgucgacau cuucaacccc aaguacgacu gcaagaucau gaccuccaag accgacguga   1260
gcuccagcgu gaucaccucc cucggcgcga ucgucagcug cuacgggaag acgaagugca   1320
ccgccagcaa caagaaccgc ggcaucauca agaccuucuc caacgggugc gacuacguga   1380
gcaacaaggg cguggacacc gucuccgugg gcaacacccu guacuacgug aacaagcagg   1440
aggggaagag ccuguacguc aagggcgagc ccaucaucaa cuucuacgac cccucgugu   1500
ucccguccga cgaguucgac gccagcaucu cccaggugaa cgagaagauc aaccagagcc   1560
uggccuucau ccggaagucc gacgagcugc ugcaccacgu caacgccggg aagagcacga   1620
ccaacaucau gaucaccacc aucaucaucg ugaucaucgu gauccuccug ucccugaucg   1680
cggucggccu ccugcuguac ugcaaggccc gcagcacgcc cgugacccuc uccaaggacc   1740
agcugagcgg gaucaacaac aucgccuucu ccaacugagg acuagugcau cacauuuaaa   1800
agcaucucag ccuaccauga gaauaagaga aagaaaauga agaucaauag cuuauucauc   1860
ucuuuuucuu uuucguuggu guaaagccaa cacccugucu aaaaaacaua aauuucuuua   1920
aucauuuugc cucuuuucuc ugugcuucaa uuaauaaaaa auggaaagaa ccuagaucua   1980
aaaaaaaaaa aaaaaaaaaa aaaaaaaaaa aaaaaaaaaa aaaaaaaaaa aaaaaaaaaa   2040
aaaugcaucc cccccccccc cccccccccc cccccccca aaggcucuuu ucagagccac   2100
cagaauu                                                             2107
```

<210> SEQ ID NO 33
<211> LENGTH: 2044
<212> TYPE: RNA
<213> ORGANISM: Artificial Sequence
<220> FEATURE:
<223> OTHER INFORMATION: RSV-Fdel554-574 long (GC) R2821

<400> SEQUENCE: 33

```
ggggcgcugc cuacggaggu ggcagccauc uccuucucgg caucaagcuu accauggagc     60
ugcccauccu caaggccaac gccaucacca ccauccuggc ggccgugacg uucugcuucg    120
ccagcuccca gaacaucacc gaggaguucu accagagcac cugcuccgcc gucagcaagg    180
gcuaccuguc cgcccuccgg accgggguggu acacgagcgu gaucaccauc gagcugucca   240
acaucaagga gaacaagugc aacggcaccg acgcgaaggu gaagcugauc aaccaggagc    300
ucgacaagua caagaacgcc gucaccgagc ugcagcugcu caugcagagc acgaccgccg    360
ccaacaaccg cgcgcggcgc gagcugccgc gguucaugaa cuacacccug aacaacacca    420
agaagacgaa cgugacccuc uccaagaagc gcaagcggcg cuuccugggg uuccugcucg    480
gcguggggag cgccaucgcc uccggcaucg ccgucagcaa ggugcugcac cuggagggcg    540
aggugaacaa gaucaagucc gcccuccuga gcaccaacaa ggcggucgug ucccugagca    600
acggggguguc cguccucacc agcaaggugc uggaccugaa gaacuacauc gacaagcagc   660
uccugcccau cgugaacaag caguccugcc ggaucagcaa caucgagacg gucaucgagu    720
uccagcagaa gaacaaccgc cugcucgaga ucacccggga guucagcgug aacgccggcg    780
```

```
ugaccacccc cgucuccacg uacaugcuga ccaacagcga gcugcucucc cugaucaacg    840
acaugcccau caccaacgac cagaagaagc ugaugagcaa caacgugcag aucgugcgcc    900
agcaguccua cagcaucaug uccaucauca aggaggaggu ccucgccuac gugguguagc    960
ugccgcugua cggggucauc gacacccccu gcuggaagcu ccacacgagc cccugugca    1020
ccaccaacac caaggagggc uccaacaucu gccugacgcg gaccgaccgc ggguguguacu    1080
gcgacaacgc cggcagcgug uccuucuucc cccaggccga gaccugcaag guccagagca   1140
accggguguu cugcgacacc augaacuccc ucacgcugcc gagcgaggug aaccugugca   1200
acgucgacau cuucaacccc aaguacgacu gcaagaucau gaccuccaag accgacguga   1260
gcuccagcgu gaucaccucc cucggcgcga ucgucagcug cuacgggaag acgaagugca   1320
ccgccagcaa caagaaccgc ggcaucauca agaccuucuc caacgggugc gacuacguga   1380
gcaacaaggg cguggacacc gucuccgugg gcaacacccu guacuacgug aacaagcagg   1440
aggggaagag ccuguacguc aagggcgagc ccaucaucaa cuucuacgac ccccucgugu   1500
ucccguccga cgaguucgac gccagcaucu cccaggugaa cgagaagauc aaccagagcc   1560
uggccuucau ccggaagucc gacgagcugc ugcaccacgu caacgccggg aagagcacga   1620
ccaacaucau gaucaccacc aucaucaucg ugaucaucgu gauccuccug ucccugaucg   1680
cggucggccu ccugcuguac ugcaaggccc gcugaggacu agugcaucac auuuaaaagc   1740
aucucagccu accaugagaa uaagagaaag aaaaugaaga ucaauagcuu auucaucucu   1800
uuuucuuuuu cguuggugua aagccaacac ccugucuaaa aaacauaaau uucuuuaauc   1860
auuuugccuc uuuucucugu gcuucaauua auaaaaaaug gaaagaaccu agaucuaaaa   1920
aaaaaaaaaa aaaaaaaaaa aaaaaaaaaa aaaaaaaaaa aaaaaaaaaa aaaaaaaaaa   1980
ugcauccccc cccccccccc cccccccccc ccccccaaag gcucuuuuca gagccaccag   2040
aauu                                                                 2044
```

<210> SEQ ID NO 34
<211> LENGTH: 1558
<212> TYPE: RNA
<213> ORGANISM: Artificial Sequence
<220> FEATURE:
<223> OTHER INFORMATION: RSV-N (GC) R2831

<400> SEQUENCE: 34

```
ggggcgcugc cuacggaggu ggcagccauc uccuucucgg caucaagcuu accauggccc     60
ugagcaaggu gaagcucaac gacacccuga acaaggacca gcugcucucc agcuccaagu    120
acaccaucca gcgcagcacg ggcgacucca ucgacacccc caacuacgac guccagaagc    180
acaucaacaa gcugugcggg augcugcuca ucaccgagga cgccaaccac aaguucaccg    240
gccugaucgg gaugcuguac gcgaugagcc ggcucggccg cgaggacacg aucaagaucc    300
ugcgggacgc cggguaccac gugaaggcca acggcgugga cgucaccacc caccgccagg    360
acaucaacgg caaggagaug aaguucgagg ugcugacccu cgccucccug acgaccgaga    420
uccagaucaa caucgagauc gagagccgga aguccuacaa gaagaugcug aaggagaugg    480
gggagguggc cccggaguac cgccacgaca gccccgacug cggcaugauc auccucugca    540
ucgcggcccu ggucaucacc aagcuggccg ccggggaccg guccggccuc accgcggugga    600
uccgccgggc caacaacgug cugaagaacg agaugaagcg cuacaagggg cugcucccca    660
aggacaucgc caacagcuuc uacgaggucu ucgagaagca cccccacuuc aucgacgugu    720
```

```
ucgugcacuu cggcaucgcc caguccagca cgcggggcgg gucccgcguc gagggcaucu     780

ucgccgggcu guucaugaac gcguacggcg ccggccaggu gaugcugcgg uggggcgugc     840

ucgccaagag cgucaagaac aucaugcugg ggcacgccuc cgugcaggcc gagauggagc     900

agguggucga gguguacgag uacgcgcaga agcugggcgg cgaggccggg uucuaccaca     960

uccucaacaa cccgaaggcc agccugcugu cccucaccca guucccgcac uucagcagcg    1020

ugguccuggg gaacgccgcc ggccugggga ucaugggcga guaccgcggg accccgcgga    1080

accaggaccu cuacgacgcg gccaaggccu acgccgagca gcugaaggag aacggcguga    1140

ucaacuacuc cgugcuggac cucaccgccg aggagcugga ggcgaucaag caccagcuga    1200

accccaagga caacgacguc gagcucugag gacuagugca ucacauuuaa aagcaucuca    1260

gccuaccaug agaauaagag aaagaaaaug aagaucaaua gcuuauucau cucuuuuucu    1320

uuuucguugg uguaaagcca acacccuguc uaaaaaacau aaauuucuuu aaucauuuug    1380

ccucuuuucu cugugcuuca auuaauaaaa aauggaaaga accuagaucu aaaaaaaaaa    1440

aaaaaaaaaa aaaaaaaaaa aaaaaaaaaa aaaaaaaaaa aaaaaaaaaa aaaaugcauc    1500

cccccccccc cccccccccc cccccccccc aaaggcucuu uucagagcca ccagaauu      1558
```

<210> SEQ ID NO 35
<211> LENGTH: 967
<212> TYPE: RNA
<213> ORGANISM: Artificial Sequence
<220> FEATURE:
<223> OTHER INFORMATION: RSV-M2-1 (GC) R2833

<400> SEQUENCE: 35

```
ggggcgcugc cuacggaggu ggcagccauc uccuucucgg caucaagcuu accaugagcc      60

gccggaaccc cugcaaguuc gagauccgcg gccacugccu gaacgggaag cggugccacu     120

ucucccacaa cuacuucgag uggccgcccc acgcccuccu ggugcgccag aacuucaugc     180

ugaaccggau ccucaagagc auggacaagu ccaucgacac ccugagcgag aucuccggcg     240

ccgcggagcu ggaccgcacc gaggaguacg cccucggggu cgugggcgug cuggagagcu     300

acaucggguc caucaacaac aucacgaagc agagcgccug cgucgccaug uccaagcugc     360

ucaccgagcu gaacagcgac gacaucaaga agcugcggga caacgaggag cucaacuccc     420

ccaagauccg cguguacaac accgugauca gcuacaucga guccaaccgg aagaacaaca     480

agcagaccau ccaccugcug aagcgccucc ccgccgacgu ccugaagaag acgaucaaga     540

acacccugga cauccacaag agcaucacca ucaacaaccc gaaggagcuc accguguccg     600

acacgaacga ccacgcgaag aacaacgaca ccaccugagg acuagugcau cacauuuaaa     660

agcaucucag ccuaccauga gaauaagaga aagaaaauga agaucaauag cuuauucauc     720

ucuuuuucuu uuucguuggu guaaagccaa cacccugucu aaaaaacaua aauuucuuua     780

aucauuuugc cucuuuucuc ugugcuucaa uuaauaaaaa auggaaagaa ccuagaucua     840

aaaaaaaaaa aaaaaaaaaa aaaaaaaaaa aaaaaaaaaa aaaaaaaaaa aaaaaaaaaa     900

aaaugcaucc cccccccccc cccccccccc cccccccccca aaggcucuuu ucagagccac     960

cagaauu                                                               967
```

<210> SEQ ID NO 36
<211> LENGTH: 75
<212> TYPE: DNA
<213> ORGANISM: Homo sapiens

<400> SEQUENCE: 36

-continued

```
gcggctcggc cattttgtcc cagtcagtcc ggaggctgcg gctgcagaag taccgcctgc     60

ggagtaactg caaag                                                      75


<210> SEQ ID NO 37
<211> LENGTH: 24
<212> TYPE: RNA
<213> ORGANISM: Artificial Sequence
<220> FEATURE:
<223> OTHER INFORMATION: histone stem-loop sequence

<400> SEQUENCE: 37

caaaggcucu uuucagagcc acca                                            24
```